US009551721B2

(12) United States Patent
Moola et al.

(10) Patent No.: US 9,551,721 B2
(45) Date of Patent: Jan. 24, 2017

(54) IDENTIFICATION OF SMALL MOLECULES RECOGNIZED BY ANTIBODIES IN SUBJECTS WITH NEURODEGENERATIVE DISEASES

(75) Inventors: Muralidhar Reddy Moola, Jupiter, FL (US); Dwight German, Dallas, TX (US); Steven Connell, McKinney, TX (US); Rosemary Wilson, Jupiter, FL (US); Johnnie Wilson, Jupiter, FL (US); Thomas Kodadek, Jupiter, FL (US)

(73) Assignees: The Board of Regents of the University of Texas System, Austin, TX (US); OPKO Health, Inc., Miami, FL (US)

( * ) Notice: Subject to any disclaimer, the term of this patent is extended or adjusted under 35 U.S.C. 154(b) by 672 days.

(21) Appl. No.: 12/791,389

(22) Filed: Jun. 1, 2010

(65) Prior Publication Data
US 2010/0303805 A1 Dec. 2, 2010

Related U.S. Application Data

(60) Provisional application No. 61/183,260, filed on Jun. 2, 2009, provisional application No. 61/318,655, filed on Mar. 29, 2010.

(51) Int. Cl.
| | | |
|---|---|---|
| *A61K 39/395* | (2006.01) | |
| *C07K 16/44* | (2006.01) | |
| *C07C 237/20* | (2006.01) | |
| *C07D 317/58* | (2006.01) | |
| *A61P 25/28* | (2006.01) | |
| *G01N 33/53* | (2006.01) | |
| *C40B 30/04* | (2006.01) | |
| *G01N 33/68* | (2006.01) | |
| *G01N 33/564* | (2006.01) | |

(52) U.S. Cl.
CPC ........ *G01N 33/6896* (2013.01); *G01N 33/564* (2013.01); *G01N 33/6845* (2013.01); *G01N 2800/2821* (2013.01); *G01N 2800/2835* (2013.01)

(58) Field of Classification Search
CPC .............. G01N 33/564; G01N 33/6845; G01N 33/6896; G01N 2800/2835; G01N 2800/2821
See application file for complete search history.

(56) References Cited

U.S. PATENT DOCUMENTS

| | | | |
|---|---|---|---|
| 4,789,628 A | 12/1988 | Nayak | 435/7 |
| 5,011,771 A | 4/1991 | Bellet et al. | 435/7.94 |
| 5,149,626 A | 9/1992 | Fleming | 435/7.9 |
| 5,510,540 A | 4/1996 | Hozumi et al. | 568/640 |
| 5,617,060 A | 4/1997 | Wilson et al. | 330/129 |
| 5,705,614 A | 1/1998 | Ring | 530/387.3 |
| 5,719,060 A | 2/1998 | Hutchens et al. | 436/174 |
| 6,153,596 A | 11/2000 | Liotta et al. | 514/44 A |
| 6,197,599 B1 | 3/2001 | Chin et al. | 436/518 |
| 6,225,047 B1 | 5/2001 | Hutchens et al. | 435/5 |
| 6,297,059 B1 | 10/2001 | Song | 436/501 |
| 6,306,643 B1 | 10/2001 | Gentalen | 435/287.2 |
| 6,329,209 B1 | 12/2001 | Wagner et al. | 436/518 |
| 6,344,330 B1 | 2/2002 | Ellman | 435/7.1 |
| 6,344,334 B1 | 2/2002 | Ellman | 435/7.1 |
| 6,365,347 B1 | 4/2002 | Murray et al. | 435/6 |
| 6,365,418 B1 | 4/2002 | Wagner et al. | 436/518 |
| 6,406,921 B1 | 6/2002 | Wagner et al. | 436/518 |
| 6,461,515 B1 | 10/2002 | Safir et al. | 210/656 |
| 6,465,183 B2 | 10/2002 | Wolber | 435/6 |
| 6,465,430 B1 | 10/2002 | Dower et al. | 514/13 |
| 6,475,391 B2 | 11/2002 | Safir et al. | 210/656 |
| 6,800,728 B2 | 10/2004 | Schwartz | 530/345 |
| 7,091,046 B2 | 8/2006 | Monforte | 436/173 |
| 7,504,364 B2 | 3/2009 | Carlson | 506/30 |
| 7,504,365 B2 | 3/2009 | Carlson | 506/30 |
| 2002/0006620 A1 | 1/2002 | Short | 435/6 |
| 2002/0018749 A1 | 2/2002 | Hudson et al. | 424/1.49 |
| 2002/0022227 A1 | 2/2002 | Short | 435/6 |
| 2002/0055125 A1 | 5/2002 | Charych et al. | 435/7.5 |
| 2002/0055186 A1 | 5/2002 | Barry et al. | 436/518 |
| 2002/0098493 A1 | 7/2002 | Nathan | 435/6 |
| 2002/0137106 A1 | 9/2002 | Leung | 435/7.9 |
| 2002/0168699 A1 | 11/2002 | Thompson et al. | 435/7.92 |
| 2002/0192690 A1 | 12/2002 | Dower et al. | 435/6 |
| 2003/0003516 A1 | 1/2003 | Robinson et al. | 435/7.9 |
| 2003/0017508 A1 | 1/2003 | Charych et al. | 435/7.9 |
| 2003/0092009 A1 | 5/2003 | Palm | 435/6 |
| 2003/0153014 A1 | 8/2003 | Shen et al. | 435/7.9 |
| 2003/0207467 A1 | 11/2003 | Snyder et al. | 436/518 |

(Continued)

FOREIGN PATENT DOCUMENTS

| | | |
|---|---|---|
| CN | 1436192 | 8/2003 |
| CN | 101119715 | 2/2008 |

(Continued)

OTHER PUBLICATIONS

Wagner et al Amino Acids Angew Chem Int Ed Engl 1983 p. 816.*
Gocke et al., "Supplemental Data—Isolation of antagonists of antigen-specific autoimmune T cell proliferation." *Chemistry & Biology*, 16:1133-1139, 2009.
Lindstrom and Robinson. "Fishing for biomarkers with antigen mimics," *Cell*, 144:13-15, 2011.
Reddy et al., "Identification of candidate IgG biomarkers for Alzheimer's disease via combinatorial library screening." *Cell*, 144:132-142, 2011.

(Continued)

*Primary Examiner* — David J Blanchard
*Assistant Examiner* — Thurman Wheeler
(74) *Attorney, Agent, or Firm* — Parker Highlander PLLC

(57) ABSTRACT

The present invention provides for the identification of individuals having neurodegenerative diseases (ND). Peptoids recognized by Parkinson's Disease- and Alzheimer's Disease-specific antibodies are identified, allowing one to diagnose or predict ND in subjects.

10 Claims, 18 Drawing Sheets

(56) References Cited

U.S. PATENT DOCUMENTS

| | | |
|---|---|---|
| 2004/0161748 A1 | 8/2004 | He et al. ............................ 435/6 |
| 2004/0161798 A1 | 8/2004 | Kodadek ........................ 435/7.1 |
| 2004/0171068 A1 | 9/2004 | Wehland et al. .............. 435/7.1 |
| 2004/0241751 A1 | 12/2004 | Wagner et al. ................ 435/7.1 |
| 2005/0048566 A1 | 3/2005 | Delisi et al. ................... 435/7.1 |
| 2005/0048580 A1 | 3/2005 | Labaer et al. ................. 435/7.1 |

FOREIGN PATENT DOCUMENTS

| | | |
|---|---|---|
| EP | 0268296 | 5/1988 |
| EP | 0317804 | 5/1989 |
| EP | 0491362 | 6/1992 |
| EP | 0586618 | 7/1997 |
| EP | 0818467 | 1/1998 |
| EP | 1319954 | 6/2003 |
| GB | 2404734 | 2/2005 |
| JP | 2003-513283 | 8/2003 |
| JP | 2009-507833 | 2/2009 |
| WO | WO 98/59360 | 12/1998 |
| WO | WO 99/51773 | 10/1999 |
| WO | WO 00/56934 | 9/2000 |
| WO | WO 01/57530 | 8/2001 |
| WO | WO 01/69258 | 9/2001 |
| WO | WO 01/88538 | 11/2001 |
| WO | WO 01/98534 | 12/2001 |
| WO | WO 02/18648 | 3/2002 |
| WO | WO 02/31510 | 4/2002 |
| WO | WO 02/46757 | 6/2002 |
| WO | WO 02/063299 | 8/2002 |
| WO | WO 02/073209 | 9/2002 |
| WO | WO 03/050544 | 6/2003 |
| WO | WO 03/072827 | 9/2003 |
| WO | WO 03/074722 | 9/2003 |
| WO | WO 03/074990 | 9/2003 |
| WO | WO 2004/005319 | 1/2004 |
| WO | WO 2004/005477 | 1/2004 |
| WO | WO 2005/007677 | 1/2005 |
| WO | WO 2006/124644 | 11/2006 |
| WO | WO 2007/030804 | 3/2007 |
| WO | WO 2008/048970 | 4/2008 |
| WO | WO 2010/138797 | 12/2010 |

OTHER PUBLICATIONS

"Biomarker Discovery: Expression difference mapping™ applications," www.ciphergen.com/techapps/pc/apps/biomarker/edm.asp, Sep. 28, 2004.

"Biomarker Discovery: Interaction discovery mapping™ application," www.ciphergen.com/techapps/pc/apps/biomarker/idm.asp, Sep. 28, 2004.

"Leading the way in biomarker research: Accelerating biomarker discovery assays," Ciphergen® The ProteingChip® Company, Product Information Sheet, 2004.

"ProteinChip® Technology: Array technology," www.ciphergen.com/techapps/pc/tech/arrays.asp, Sep. 28, 2004.

"Unraveling biological pathways using the Interaction Discovery Mapping™ platform," Ciphergen® The ProteingChip® Company, Product Information Sheet, 2004.

Alluri et al., "Isolation of protein ligands from large peptoid libraries," J. Am. Chem. Soc., 125:13995-14004, 2003.

Alluri, et al., "Isolation and characterization of coactivator-binding peptoids from a combinatorial library," Mol. BioSystems, 2:568-79, 2006.

Astle et al., "A VEGFR2 antagonist and other peptoids evade immune recognition," Int J Pept Res Ther, 14:223-227, 2008.

Bachhawat-Sikder and Kodadek, "Mixed-element capture agents: a simple strategy for the construction of synthetic, high-affinity protein capture ligands," J. Am. Chem. Soc., 125:9550-9551, 2003.

Baldini et al., "Pattern-based detection of different proteins using an array of fluorescent protein surface receptors," J. Am. Chem. Soc., 126:5656-5657, 2004.

Borman, "Combinatorial chemistry," Chem. &Eng. News, 75: 43-62,1997.

Brenner et al., "Gene expression analysis by massively parallel signature sequencing (MPSS) on microbead arrays," Nature Biotechnology, 18:630-634, 2000.

Brocchini et al., "A Combinatorial Approach for Polymer Design," J. Am. Chem. Soc., 119:4553-4554, 1997.

Burger and Still, "Simple structural requirements for sequence-selective peptide receptors? Tripeptide binding by a podand ionophore," J. Org, Chem., 62:4785-4790, 1997.

Burkoth et al., "Toward the synthesis of artificial proteins: the discovery of an amphiphilic helical peptoid assembly," Chem. Biol., 9:647-654, 2002.

Burton, "Phage display," Immunotechnology 1:87-94,1995.

Caputo et al., "Methods for on-chip protein analysis," Analytical Biochemistry, 321:116-124, 2003.

Carins et al., "A novel bacterial vector system for monitoring protein-protein interactions in the cAMP-dependent protein kinase complex," Gene, 185:5-9, 1997.

Cekaite et al., "Analysis of the humoral immune response to immunoselected phage-displayed peptides by a microarray-based method," Proteomics, 4:2572-2582, 2004.

Chen et al., "Fluorescent, sequence-selective peptide detection by synthetic small molecules," Science, 279:851-853, 1998.

Cheng et al., "Sequence-selective peptide binding with peptido-A. B-trans-steroidal receptor selected from an encoded combinatorial receptor library," J. Amer. Chem. Soc., 118:1813-1814, 1996.

Cho et al., "Cyclic and linear oligocarbamate ligands for human thrombin," Bioorg Med Chem 7, 1171-1179, 1999.

Conrads et al., "Cancer diagnosis using proteomic patterns," Expert. Rev. Mol.Diagn., 3:411-420, 2003.

Conrads et al., "High-resolution serum proteomic features for ovarian cancer detection," Endocrine-Related Cancer, 11:163-178, 2004.

Conrads et al., "Proteomic patterns as a diagnostic tool for early-stage cancer: a review of its progress to a clinically relevant tool," Mol. Diagn. 8:77-85, 2004.

Cox et al., "Integrating gene and protein expression data: pattern analysis and profile mining," Methods, 35:303-314, 2005.

Cussac et al., "A Sos-derived peptidimer blocks the Ras signaling pathway by binding both Grb2 SH3 domains and displays antiproliferative activity," FASEB J., 13:31-38, 1999.

Davies and Riechmann, "Single antibody domains as small recognition units: design and in vitro antigen selection of camelized, human VH domains with improved protein stability," Protein Engineering, 9(6):531-537, 1996.

Deinhofer et al., "Microarrayed allergens for IgE profiling," Methods, 32:249-254, 2004.

Demir et al., "Proteome analysis of human mesothelial cells during epithelial to mesenchymal transitions induced by shed menstrual effluent," Proteomics, 4:2608-2623, 2004.

Dinarello, "Interleukin-1 beta, interleukin-18, and the interleukin-1 beta converting enzyme," Ann. N.Y. Acad. Sci., 856:1-11, 1998.

Dong et al., "Molecular forceps from combinatoral libraries prevent the farnesylation of Ras by binding to its carboxyl terminus," Chem. & Biol., 6:133-144, 1999.

Dostmann et al., "Delineation of selective cyclic GMP-dependent protein kinase Ialpha substrate and inhibitor peptides based on combinatorial peptide libraries on paper," Pharmacol. Ther., 82:373-387, 1999.

Dove et al., "Conversion of the w subunit of Escherichia coli RNA polymerase into a transcriptional activator or activation target," Gene and Development, 12:745-754, 1998.

Eichler et al., "Peptide, peptidomimetic, and organic synthetic combinatorial libraries," Med Res Rev., 15(6):481-96, 1995.

Elgersma et al., "Transformation of the amyloidogenic peptide amylin into its corresponding peptoid and retropeptoid: Access to both an amyloid inhibitor and templae for self-assembled supramolecular tapes," Bioorganic and Medicinal Chemistry Letters, 17:1837-1842, 2007.

Fairbrother et al. "Novel peptides selected to bind vascular endothelial growth factor target the receptor-binding site," Biochemistry, 37:17754-17764, 1998.

(56) References Cited

OTHER PUBLICATIONS

Fancy and Kodadek, "Chemistry for the analysis of protein-protein interactions: rapid and efficient cross-linking triggered by long wavelength light," *Proc. Natl. Acad. Sci., USA*, 96:6020-6024, 1999.
Figliozzi et al., "Synthesis of N-substituted glycine peptoid libraries,"*Methods Enzymol.*, 267:437-447, 1996.
Fodor et al., "Light-directed, spatially addressable parallel chemical synthesis," *Science*, 251:767-773, 1991.
Forterre et al., "Protein profiling of urine from dogs with renal disease using ProteinChip analysis," *J. Vet. Diagn. Invest.*, 16:271-277, 2004.
Gallop et al., "Applications of combinatorial technologies to drug discovery. 1. Background and peptide combinatorial libraries," *J. Med. Chem.*, 37(9):1233-1251, 1994.
Gocke et al., "Isolation of antagonists of antigen-specific autoimmune T cell proliferation," *Chem. and Biol.*, 16(11):1133-1139, 2009.
Gordon et al., "Applications of combinatorial technologies to drug discovery. 2. Combinatorial organic synthesis, library screening strategies, and future directions," *J. Med. Chem.*, 37(10):1385-401, 1994.
Griffiths and Duncan, "Strategies for selection of antibodies by phage," *Curr. Opin. Biotechnol.*, 9:102-108, 1998.
Grow et al., "New biochip technology for label-free detection of pathogens and their toxins," *J. Microbiological Methods*, 53:221-233, 2003.
Gruden et al., "Differential neuroimmune markers to the onset of Alzheimer's disease neurodegeneration and dementia: Autoantibodies to A$\beta_{(25\text{-}35)}$ oligomers, S100b and neurotransmitters,"*Journal of Neuroimmunology*, 186:181-192, 2007.
Grumwald et al., "In situ assembly of macromolecular complexes triggered by light," *PNAS*, 107(14):6146-6151, 2010.
Hajduk et al., "Discovery of potent nonpeptide inhibitors of stromelysin using SAR by NMR," *J. Amer. Chem. Soc.*, 119:5818-5827, 1997.
Han and Kodadek, "Peptides selected to bind the Ga180 repressor are potent transcriptional activation domains in yeast," *J. Biol. Chem.*, 275(20):14979-14984, 2000.
Harland and Weintraub, "Translation of mRNA injected into *Xenopus* oocytes is specifically inhibited by antisense RNA,"*J. Cell Biol.* 101:1094-1099, 1985.
He et al.,"Transformation of wheat (*Triticum aestivum* L.) through electroporation of protoplasts," *Plant Cell Reports*, 14:192-196, 1994.
Heine et al., "Synthesis and screening of peptoid arrays on cellulose membranes," *Tetrahedron*, 59:9919-9930, 2003.
Hiemstra et al., "Antigen arrays in T cell immunology," *Current Opinion in Immunology*, 12:80-84, 2000.
Hoffmann et al., "Transformation of a biologically active peptide into peptoid analogs while retaining biological activity," *Protein & Peptide Letters*, 13:829-833, 2006.
Horn, et al., "Incorporation of chemoselective functionalities into peptoids via solid-phase submonomer synthesis," *Bioconj. Chem.*, 15:428-35, 2004.
Hossain and Schneider, "Sequence-selective evaluation of peptide side-chain interaction. New artificial receptors for selective recognition in water", *J. Amer. Chem. Soc.*, 120:11208-11209, 1998.
Howard et al., "Identification of collagen-binding proteins in *Lactobacillus* spp. with surface-enhanced laser desorption/ionization-time of flight ProteinChip technology," *Applied and Environmental Microbiology*, 66:4396-4400, 2000.
Hu et al, "Sequence requirements for coiled-colis: Analysis with lambda Repressor-GCN4 leucine zipper fusions," *Science*, 250:1400-1403, 1990.
Hu, "Repressor fusions as a tool to study protein-protein interactions," *Structure* 3:431-433, 1995.
Huang et al., "Enhanced protein profiling arrays with ELISA-based amplification for high-throughput molecular changes of tumor patients' plasma," *Clinical Cancer Research*, 10:598-609, 2004.
Huang et al., "High-Throughput Genomic and Proteomic Analysis Using Microarray Technology," *Clinical Chemistry*, 47:1912-1916, 2001.
Huber et al., "Comparison of Proteomic and Genomic Analyses of the Human Breast Cancer Cell Line T47D and the Antiestrogen-resistant Derivative T47D-r*," *Molecular & Cellular Proteomics 3.1*, 3:43-55, 2004.
Hudelist et al., "Use of high-throughput protein array for profiling of differentially expressed proteins in normal and malignant breast tissue," *Breast Cancer Research and Treatment*, 86:281-291, 2004.
Hueber et al., "Autoantibody profiling for the study and treatment of autoimmune disease," *Arthritis Res.*, 4(5): 290-295, 2002.
International Search Report and Written Opinion issued in PCT/US2010/036827, dated Aug. 30, 2010.
Ivanov et al., "Antibodies Immobilized as Arrays to Profile Protein Post-translation Modifications in Mammalian Cells," *Molecular & Cellular Proteomics 3.8*, 3:788-795, 2004.
Jappelli and Brenne, "Interaction between cAMP-dependent protein kinase catalytic subunit and peptide inhibitors analyzed with λ Repressor fusions," *J. Mol. Bio.,.* 259:575-578, 1996.
Jenkins and Pennington, "Arrays of protein expresion profiling: Towards a viable alternative to two-dimensional gel electrophoresis?" *Proteomics*, 1:13-29, 2001.
Kanemitsu and Kanie, "Recent developments in oligosaccharide synthesis: tactics, solid-phase synthesis and library synthesis," *Comb Chem High Throughput Screen*, 5(5):339-360, 2002.
Kaplan et al., "A new mechanism for immunologic initiation of asthma," *PNAS*, 102(5):1267-1268, 2005.
Kiessling et al., "Synthetic multivalent ligands in the exploration of cell-surface interactions," *Curr. Opin. Chem. Biol.*, 4:696-703, 2000.
Kim et al., "Photo-induced protein cross-linking mediated by palladium porphyrins," *J. Amer. Chem. Soc.*, 121:11896-11897, 1999.
Kirshenbaum et al., "Sequence-specific polypeptoids: a diverse family of heteropolymers with stable secondary structure," *Proc. Natl. Acad. Sci., USA*, 95:4303-4308, 1998.
Kitov et al., "Shiga-like toxins are neutralized by tailored multivalent carbohydrate ligands," *Nature*, 403:669-672, 2000.
Kodadek, "Development of protein-detecting microarrays and related devices," *Trends Biochem. Sci.*, 27(6):295-300, 2002.
Kodadek, "Protein microarrays: prospects and problems," *Chem. Biol.*, 8:105-115, 2001.
Koehler et al., "Discovery of an inhibitor of a transcription factor using small molecule microarrays and diversity-oriented synthesis," *J. Amer. Chem. Soc.*, 125:8420-8421, 2003.
Kuruvilla et al., "Dissecting glucose signaling with diversity-oriented synthesis and small-molecule microarrays," *Nature*, 416:653-657, 2002.
Kwon and Kodadek, "Encoded combinatorial libraries for the construction of cyclic peptoid microarrays," *Chem. Commun.*, pp. 5704-5706, 2008.
Kwon and Kodadek, "Encoded combinatorial libraries for the construction of cyclic peptoid microarrays," *Chem. Comm.*, 44:S1-S21, 2008.
Ladbury et al., "Measurement of the binding of tyrosyl phosphopeptides to SH2 domains: a reappraisal.," *Proc. Natl. Acad. Sci., USA*, 92:3199-3203, 1995.
Le Bihan et al., "Evaluation of an integrated strategy for proteomic profiling of skeletal muscle," *Proteomics*, 4:2739-2753, 2004.
Leak et al., "Proteomic analysis of lymph," *Proteomics*, 4:753-765, 2004.
Lee et al., "Protein patterning on silicon-based surface using background hydrophobic thin film," *Biosensors and Bioelectronics*, 18:437-444, 2003.
LePlae et al., "Tolerence of Acyclic Residues in the beta-Peptide 12-Helix: Access to Diverse Side-Chain Arrays for Biological Applications," *J. Amer. Chem. Soc.*, 124:6820-6821, 2002.
Li et al., "Photolithographic synthesis of cyclic peptide arrays using a differential deprotection strategy," *Chem. Commun.*, 581-583, 2005.
Li et al., "Photolithographic Synthesis of Peptoids," *J. Am. Chem. Soc.*, 126:4088-4089, 2004.

(56) References Cited

OTHER PUBLICATIONS

Ligler et al., "Array biosensor for detection of toxins," *Anal. Bioanal. Chem.*, 377:469-477, 2003.
Lin et al., "Profiling of cytokine expression by biotin-labeled-based protein arrays," *Proteomics*, 3:1750-1757, 2003.
Liu et al., "Analysis of Prostate Cancer by Proteomics using Tissue Specimens," *J. Urology*, 173:73-78, 2005.
Lopez et al., "Serum Autoantibodies in Patients with Alzheimer's Disease and Vascular Dementia and Nondemented Control Subjects," *Stroke*, 23:1078-1083,1992.
MacBeath, et al., "Printing small molecules as microarrays and detecting protein-ligand interactions en masse," *J. Am. Chem. Soc.*, 121:7967-8, 1999.
Maly et al., "Combinatorial target-guided ligand assembly: identification of potent subtype-selective c-Src inhibitors," *Proc. Natl. Acad. Sci., USA*, 97:2419-2424, 2000.
Martin, "Preorganization in biological systems: Are conformational constraints worth the energy?" *Pure Appl. Chem.*, 79:193-200, 2007.
Melcher and Xu, "Gal80-Gal80 interaction on adjacent Gal4p binding sites is required for complete GAL gene repression," *EMBO J.* 20:841-851, 2001.
Melle et al., "A technical triade for proteomic identification and characterization of cancer biomarkers," *Cancer Research*, 64:4099-4104, 2004.
Meloen et al., "Mimotopes: realization of an unlikely concept," *J. Mol. Recognition*, 13:352-359, 2000.
Merritt et al., "Characterization and crystal structure of a high-affinity pentavalent receptor-binding inhibitor for cholera toxin and *E. coli* heat-labile enterotoxin," *J. Amer. Chem. Soc.*, 124:8818-8824, 2002.
Mezzasoma et al., "Antigen Microarrays for Serodiagnosis of Infectious Diseases," *Clinical Chemistry*, 48:121-130, 2002.
Mikolajczyk et al., "High yield, site-specific coupling of N-terminally modified beta-lactamase to a proteolytically-derived single-sulfhydryl murine Fab," *Biooconj. Chem.*, 5:636-646, 1994.
Motoori et al., "Prediction of recurrence in advanced gastric cancer patients after curative resection by gene expression profiling," *Int. J. Cancer*, 114:963-968, 2005.
Neuman de Vegvar and Robinson, "Microarray profiling of antiviral antibodies for the development of diagnostics, vaccines, and therapeutics," *Clinical Immunology*, 111:196-201, 2004.
O et al., "Peptides mimicking sialyl-Lewis A isolated from a random peptide library and peptide array," *Ann N Y Acad Sci*, 886:276-279, 1999.
O'Brien-Simpson et al., "Polymerization of unprotected peptides: A view towards synthetic peptide vaccines," *J. Amer. Chem. Soc.*, 119:1183-1188, 1997.
Olejniczak et al., "Stromelysin inhibitors designed from weakly bound fragments: effects of linking and cooperativity," *J. Amer. Chem. Soc.*, 119:5828-5832, 1997.
Oliver et al., "Multiplexed Analysis of Human Cytokines by Use of the FlowMetrix System," *Clinical Chemistry*, 44:2057-2060, 1998.
Ornstein et al., "Serum Proteomic Profiling can Discriminate Prostate Cancer From Benign Prostates in Men with Total Prostate Specific Antigen Levels Between 2.5 and 15.0 NG/ML," *J. Urology*, 172:1302-1305, 2004.
Ostergaard and Holm, "Peptomers: A versatile approach for the preparation of diverse combinatorial peptidomimetic bead libraries," *Mol. Divers.*, 3:17-27, 1997.
Park and Raines "Genetic selection for dissociative inhibitors of designated protein-protein interactions," *Nature Biotechnol.*, 18, 847-851, 2000.
Phizicky and Fields, "Protein-protein interactions: methods for detection and analysis," *Microbiological Reviews*, 59(1):94-123, 1995.
Quintana et al., "Functional immunomics: microarray analysis of IgG autoantibody repertoires predicts the future response of mice to induced diabetes," *Proc. Nat. Acad. Sci. USA*, 101:14615-14621, 2004.

Rader and Barbas, "Phage display of combinatorial antibody libraries," *Curr. Opin. Biotechnol.*, 8:503-508, 1997.
Radulovic et al., "Informatics Platform for Global Proteomic Profiling and Biomarker Discovery Using Liquid Chromatography-Tandem Mass Spectrometry," *Molecular & Cellular Proteomics 3.10*, 3:984-997, 2004.
Reddy and Kodadek, "Protein "fingerprinting" in complex mixtures with peptoid microarrays," *Proc. Nat. Acad. Sci. USA* 102, 12672-12677, 2005.
Reddy et al., "Transformation of low-affinity lead compounds into high-affinity protein capture agents," *Chem. Biol.*, 11:1127-1137, 2004.
Reineke et al., "Identification of distinct antibody epitopes and mimotopes from a peptide array of 5520 randomly generated sequences," *J. Immunol. Methods*, 267:37-51, 2002.
Robinson et al., "Autoantigen microarrays for multiplex characterization of autoantibody responsesm," *Nature Medicine*, 8:295-301, 2002.
Robinson et al., "Protein and Peptide Array Analysis of Autoimmune Disease," *BioTechniques*, 33:S66-S69, 2002.
Robinson et al., "Protein microarrays guide tolerizing DNA vaccine treatment of autoimmune encephalomyelitis," *Nature Biotechnology*, 21:1033-1039, 2003.
Rose et al., "Natural peptides as building blocks for the synthesis of large protein-like molecules with hydrazone and oxime linkages," *Bioconj. Chem.* 7:552-556, 1996.
Sasaki et al., "A new application of a peptide library to identify selective interaction between small peptides in an attempt to develop recognition molecules toward protein surfaces," *Tetrahedron Letters*, 37:85-88, 1996.
Schneider et al., "Scaffold-hopping: by topological pharmacophore search: a contribution to virtual screening," *Angew Chem Int Ed Engl.*, 38:2894-2896, 1999.
Schreiber, "Target-oriented and diversity-oriented organic synthesis in drug discovery," *Science*, 287(5460), 1964-1969, 2000.
Scott, et al., "Production of cyclic peptides and proteins in vivo," *Proc. Natl. Acad. Sci. USA*, 96:13638-13643, 1999.
Shao et al, "Sequence-selective receptors of peptides. A simple molecular design for construction of large combinatorial libraries of receptors," *J. Org. Chem.*, 61:6086-6087, 1996.
Shepard et al., "Array-based binary analysis for bacterial typing," *Anal. Chem.*, 77:319-326, 2005.
Shuker et al., "Discovering high-affinity ligands for proteins: SAR by NMR," *Science*, 274:1531-1534, 1996.
Simon, et al., "Peptoids: a modular approach to drug discovery," *Proc. Natl. Acad. Sci. USA*, 89:9367-71, 1992.
Staub et al., "Systematic identification of immunoreceptor tyrosine-based inhibitory motifs in the human proteome," *Cellular Signalling*, 16:435-456, 2004.
Still, "Discovery of sequence-selective peptide binding by synthetic receptors using encoded combinatorial libraries," *Acc. Chem. Res.*, 29:155-163, 1996.
Stoll et al., "Chalcone derivatives antagonize interactions between the human oncoprotein MDM2 and p53," *Biochemistry*, 40:336-344, 2001.
Sydor and Nock, "Protein expression profiling arrays: tools for the multiplexed high-throughput analysis of proteins," *Proteome Science*, 1:1-7, 2003.
Tannapfel et al., "Identification of novel proteins associated with hepatocellular carcinomas using protein microarrays," *J. of Pathology*, 238-249, 2003.
Terryberry et al., "Autoantibodies in Neurogdegenerative Diseases: Antigen-Specific Frequencies and Intrathecal Analysis," *Neurobiology of Aging*, 19:205-216, Jan. 1998.
Terskikh et al., "'Peptabody': a new type of high avidity binding protein," *Proc. Natl. Acad. Sci., USA*, 94:1663-1668, 1997.
Thoma et al., "Nanomolar E-selectin inhibitors: 700-fold potentiation of affinity by multivalent ligand presentation," *J. Amer. Chem. Soc.*, 123:10113-10114, 2001.
Thompson and Ellman, "Synthesis and Applications of Small Molecule Libraries," *Chem. Rev.*, 96(1):555-600, 1996.

(56) References Cited

OTHER PUBLICATIONS

Udugamasooriya et al., "The pharmacore of a peptoid VEGF receptor 2 antagonist includes both side chain and main chain residues," *Bioorganic & Medicinal Chemistry Letters*, 18:5892-5894, 2008.

Udugamasooriya, et al., "A peptoid "antibody surrogate" that antagonizes VEGF receptor 2 activity," *J. Amer. Chem. Soc.*, 130:5744-5752, 2008.

Usui et al., "Peptide Arrays with Designed Secondary Structures for Protein Characterization Using Fluorescent Fingerprint Patterns," *Biopolymers (Peptide Science)*, 76:129-139, 2004.

Valafar, "Pattern recognition techniques in microarray data analysis: a survey," *Ann. N.Y. Acad. Sci.*, 980:41-64, 2002.

Veenstra and Conrads, "Serum protein fingerprinting," *Curr. Opin. Mol. Therapeutics*, I5:584-593, 2003.

Veenstra et al., "Proteomic patterns for early cancer detection," *DDT*, 9:889-897, 2004.

Venkatesh, et al., "Prevention of passively transferred experimental autoimmune myasthenia gravis by a phage library-derived cyclic peptide," *Proc. Natl. Acad. Sci. USA*, 97:761-6, 2000.

Vignali, "Multiplexed particle-based flow cytometric assays," *J. of Immunol. Methods*, 243:243-255, 2000.

Wang et al., "Autoantibody Signatures in Prostate Cancer," *New Eng. J. Med.*, 353:1224-1235, 2005.

Weinberger et al., "Surface-enhanced laser desorption-ionization retentate chromatography mass spectrometry (SELDI-RC-MS): a new method for rapid development of process chromatography conditions," *J. Chromatography B*, 782:307-316, 2002.

Winssinger et al., "Profiling protein function with small molecule microarrays," *PNAS*, 99:11139-11144, 2002.

Wong et al., "Protein profiling of cervical cancer by protein-biochips: proteomic scoring to discriminate cervical cancer from normal cervix," *Cancer Letters*, 211:227-234, 2004.

Woodbury and Vinton., "Methods of screening combinatorial libraries using immobilized or restrained receptors," *J. Chromatogr B Biomed. Sci. Appl.*, 725:113-137, 1999.

Xiao et al., "A preliminary analysis of non-small cell lung cancer biomarkers in serum," *Biomedical and Environmental Sciences*, 16:140-148, 2003.

Xiao et al., "Discovery of laryngeal carcinoma by serum proteomic pattern analysis," *Science in China Ser. C Life Sciences*, 47:219-223, 2004.

Xie et al., "Biochemical characterization of the TATA-binding Gal4 activation domain complex," *JBC*, 275:31914-31920, 2000.

Xu et al., "Increased incidence of anti-β-amyloid autoantibodies secreted by Epstein-Barr virus transformed B cell lines from patients with Alzheimer's disease," *Mechanisms of Ageing and Development*, 94:213-222, 1997.

Yang et al., "Novel Turns and Helices in Peptides of Chiral alpha-Aminoxy Acids," *J. Amer. Chem. Soc.*, 121:589-590, 1999.

Yang et al., "Protein-peptide interactions analyzed with the two-hybrid system," *Nucl. Acids Res.*, 23:1152-1156, 1995.

Yoo et al., Peptoid architectures elaboration, actuation, and application,: *Curr Opinion Chem Biol*, 12:714-721, 2008.

Zhang et al., "An inhibitor of sequence specific proteolysis that targets the substrate rather than the enzyme," *Chem. Biol.*, 8:391-397, 2001.

Zhang et al., "Genetic selection of short peptides that support protein oligomerization in vivo," *Current Biol.*, 9:417-420, 1999.

Zhang et al., "Selection and practical applications of peptide-binding peptides," *Nature Biotechnol.*, 18:71-74, 2000.

Zhu et al., "A Cdc6-binding peptide selected using a bacterial two-hybrid-like system is a cell cycle inhibitor," *J. Biol. Chem.*, 275:32098-32105, 2000.

Zuckermann, et al., "Discovery of nanomolar ligands for 7-transmembrane G-protein-coupled receptors from a diverse N-(substituted)glycine peptoid library," *J. Med. Chem.*, 37:2678-85, 1994.

Banerjee, et al., "Efficacy of selected natural products as therapeutic agents against cancer," *J. Natural Prod.*, 71:492-6, 2008.

Chhabra et al., "An appraisal of new variants of Dde amine protecting group for solid phase peptide synthesis," *Tetrahedron Lett.*, 39:1603-6, 1998.

Fields and Song, "A novel genetic system to detect protein-protein interactions," *Nature*, 340:245-246, 1989.

Fouladi, "Histone deacetylase inhibitors in cancer therapy," *Cancer Invest.*, 24:521-7, 2006.

Hamada and Shioiri, "Recent progress of the synthetic studies of biologically active marine cyclic peptides and depsipeptides," *Chem. Rev.*, 105:4441-82, 2005.

Ho, et al., "The mechanism of action of cyclosporin A and FK506," *Clin. Immunol. Immunopathol.*, 80:S40-5, 1996.

Joo, et al., "High-throughput sequence determination of cyclic peptide library members by partial Edman degradation/mass spectrometry," *J. Amer. Chem. Soc.*, 128:13000-9, 2006.

Lech-Maranda, et al., "Depsipeptide (FK228) as a novel histone deacetylase inhibitor: mechanism of action and anticancer activity," *Mini Rev. Med. Chem.*, 7:1062-9, 2007.

Lim, et al., "Identification of a peptoid inhibitor of the proteasome 19S regulatory particle," *J. Amer. Chem. Soc.*, 129:7750-1, 2007.

Liu, et al., "A novel peptide-based encoding system for "one-bead one-compound" peptidomimetic and small molecule combinatorial libraries," *J. Amer. Chem. Soc.*, 124:7678-80, 2002.

Rezai, et al., "Conformational flexibility, internal hydrogen bonding, and passive membrane permeability: successful in silico prediction of the relative permeabilities of cyclic peptides," *J. Amer. Chem. Soc.*, 128:14073-80, 2006.

Rezai, et al., "Testing the conformational hypothesis of passive membrane permeability using synthetic cyclic peptide diastereomers," *J. Amer. Chem. Soc.*, 128:2510-1, 2006.

Satoh, et al., "Synthetic peptides derived from the fourth domain of CD4 antagonize off function and inhibit T cell activation," *Biochem. Biophys. Res. Commun.*, 224:438-43, 1996.

Shin, et al., "Cyclic peptoids," *J. Amer. Chem. Soc.*, 129:3218-25, 2007.

Udugamasooriya and Spaller, "Conformational constraint in protein ligand design and the inconsistency of binding entropy," *Biopolymers*, 89:653-67, 2008.

Uttamchandani, et al., "Small molecule microarrays: recent advances and applications," *Curr. Opin. Chem. Biol.*, 9:4-13, 2005.

Xiao, et al., "Design and synthesis of a cell-permeable synthetic transcription factor mimic," *J. Comb. Chem.*, 9:592-600, 2007.

Zuckerman et al., "Efficient method for the preparation of peptoids [oligo(N-substituted glycines)] by submonomer solid-phase synthesis," *J. Am. Chem. Soc.* 114:10646-10647, 1992.

Office Action issued in Japanese Application No. 2012-514031, mailed Nov. 11, 2013.

Office Action issued in Chinese Application No. 201080023987.9, issued Nov. 8, 2013, and English language translation thereof.

Office Action issued in Chilean Application No. 2973-2011, mailed Aug. 28, 2014.

Decision to Grant a Patent issued in Japanese Application No. 2012-514031, mailed Sep. 28, 2015.

\* cited by examiner

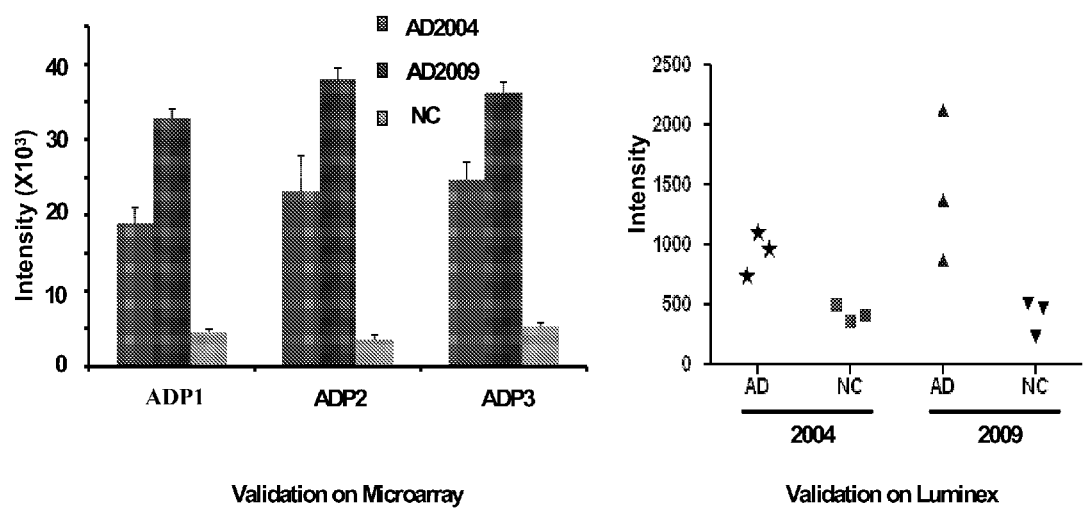
FIG. 7
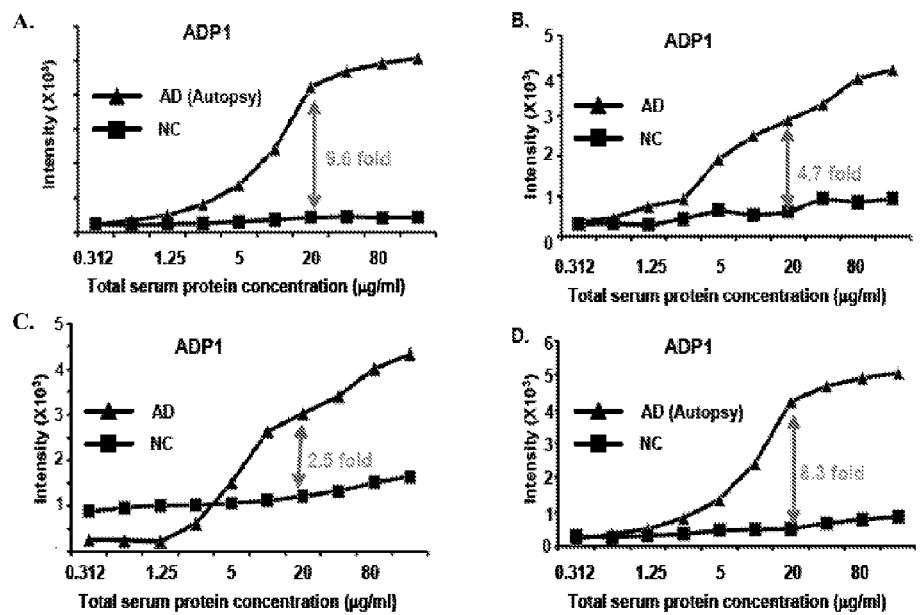
FIG. 8A-D

IDENTIFICATION OF SMALL MOLECULES RECOGNIZED BY ANTIBODIES IN SUBJECTS WITH NEURODEGENERATIVE DISEASES

This application claims priority to U.S. Provisional Application Ser. Nos. 61/183,260, filed Jun. 2, 2009 and 61/318,655 filed Mar. 29, 2010, the entire contents of which are hereby incorporated by reference.

This invention was made with government support under grant no. NO1-HV28185 from the National Heart, Lung and Blood Institute, and grant no. DP1OD00066301 from the National Institutes of Health. The government has certain rights in the invention.

BACKGROUND OF THE INVENTION

I. Field of the Invention

The present invention relates generally to the fields of molecular biology, immunology and neurobiology. More particularly, it concerns the identification of peptoids that are recognized by neurodegenerative disease (ND)-specific antibodies. These peptoids can be used to identify subjects suffering from or at risk of NDs.

II. Description of Related Art

Alzheimer's Disease (AD) is a progressive and fatal brain disease that affects as many as 5.3 million Americans. AD destroys brain cells, causing problems with memory, thinking and behavior. These symptoms get worse over time, and ultimately the disease is fatal. Today, it is the sixth-leading cause of death in the United States and is the most common form of dementia, accounting for 50-70% of all dementia cases. Sadly, while treatments for symptoms exist, there is no cure.

Diagnosing Alzheimer's Disease is an empirical process that involves several types of evaluations and may take many days to weeks to complete. Evaluations include taking a detailed medical history and physical examination. In addition, standard laboratory tests including blood, urine and CSF tests are mainly designed to help eliminate other possible conditions. Neuropsychological testing, using a variety of tools to assess memory, problem-solving, attention, vision-motor coordination and abstract thinking, are also performed. Tests for depression should also be included. Finally, brain-imaging scans are recommended to rule out brain tumors or blood clots in the brain as the reason for symptoms. In sum, there is currently no single test that accurately diagnoses Alzheimer's Disease, with a definitive diagnosis of Alzheimer's possible only by examining brain tissue after death.

Parkinson's Disease (PD) is another degenerative disease of the brain (central nervous system) that often impairs motor skills, speech, and other functions. It affects movement (motor symptoms), but other typical symptoms include disorders of mood, behavior, thinking, and sensation (non-motor symptoms). Patient's individual symptoms may be quite dissimilar and progression of the disease is also distinctly individual. The symptoms of PD result from the loss (idiopathic or genetic, toxic or traumatic) of pigmented dopamine-secreting (dopaminergic) cells in the pars compacta region of the substantia nigra (literally "black substance"). These neurons project to the striatum and their loss leads to alterations in the activity of the neural circuits within the basal ganglia that regulate movement, in essence an inhibition of the direct pathway and excitation of the indirect pathway.

Diagnosis of PD presents similar if somewhat distinct challenges. When performing a neurologic examination to evaluate a patient with any movement disorder, the doctor should take a medical history and perform a physical examination. In addition, a neurologic exam is conducted to make a thorough evaluation of the nervous system, including observing aspects of the patient's movement, coordination and balance. Laboratory testing of the blood of patients with the symptoms typical of Parkinson's only rarely uncovers any abnormality. Electroencephalograms (EEG's) record some aspects of brain electrical activity, but they are not effective in spotting PD. The MRI and CAT scans of the brain produce remarkable and exquisite anatomic pictures, but the brains of people with PD disease appear normal even under this scrutiny because the changes associated with PD are microscopic and are not revealed by these scans. With no definitive diagnostic tests to provide specific answers, physicians must base their diagnosis of PD on judgment.

Thus, there remains a need for diagnostic procedures for both of these diseases and other neurological diseases that are (i) accurate and objective, (ii) simple and reproducible, and (iii) useful in both early and late stage case.

SUMMARY OF THE INVENTION

In accordance with the present invention, there is provided compositions comprising peptoid(s) that bind antibodies indicative of a neurodegenerative disease and methods of detecting antibodies in an antibody-containing sample comprising contacting an antibody-containing sample with a support having affixed thereto a peptoid. Peptoids of the invention have the formulas:

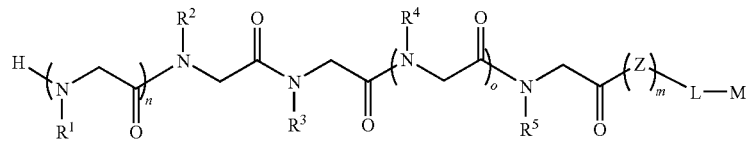

1A wherein $R^1$ and $R^4$ are independently selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl—including one or more chemical group described in Table 1 and 2 below. $R^2$, $R^3$ and $R^5$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2 below.

Or

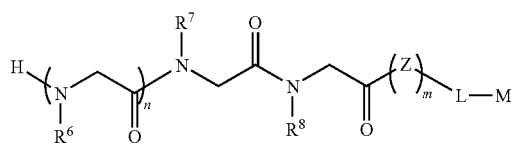

1B wherein $R_6$ is selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl; and hydroxyl group—including one or more chemical group described in Table 1 and 2 below. $R^7$ and $R^8$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2 below.

Or butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl; and hydroxyl group—including one or more chemical group described in Table 1 and 2 below. $R^{10}$, $R^{12}$ and $R^{14}$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2 below.

Or

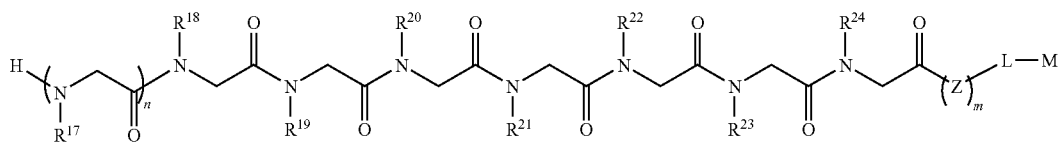

1D

Wherein, in one embodiment, $R^{17}$-$R^{20}$ and $R^{23}$ of formula 1D are independently selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline; cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl; and hydroxyl group—including one or more chemical group described in Table 1 and 2 below. $R^{21}$, $R^{22}$ and $R^{24}$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2 below.

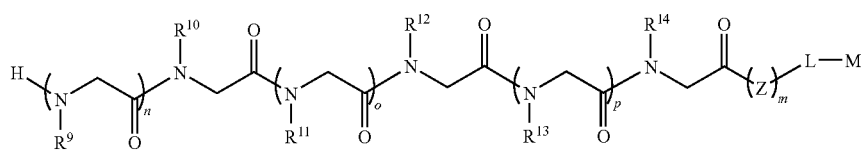

1C

Wherein $R^9$, $R^{11}$, and $R^{13}$ are independently selected from the group consisting of hydrogen; alkyl; allyl; methyl; ethyl; n-propyl; isopropyl; n-butyl; isobutyl; n-butylamine; sec- In another embodiment, $R^{17}$-$R^{20}$, $R^{23}$, and $R^{24}$ of formula 1D are independently selected from the group consisting of hydrogen; alkyl; allyl; methyl; ethyl; n-propyl; isopropyl;

n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl; and hydroxyl group—including one or more chemical group described in Table 1 and 2 below. $R^{21}$ and $R^{22}$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2 below.

In still a further embodiment, $R^{17}$, $R^{19}$, $R^{20}$, and $R^{23}$ of formula 1D are independently selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl; and hydroxyl group—including one or more chemical group described in Table 1 and 2 below. $R^{18}$, $R^{21}$ and $R^{24}$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2 below.

In formula 1A—R2, R3, R4, and R5 may additionally selected from those groups shown in Tables 1 and 2 for the equivalent letter designations that are provided for the particular peptoid monomer location in the oligomers ADP1-3 and PDP1-3. For example, in formula 1A, the R variables selected from R2, R3 and R5 may independently be selected from those side chains or monomers shown in Tables 1 and/or 2 for the specific peptoid ADP-1 as A, B or C; and so on for ADP2 (D, E, or F) and ADP3 (G, H, or I).

In formula 1B—R7 and R8 may additionally be selected from those groups shown in Tables 1 and 2 for the equivalent letter designations that are provided for the particular peptoid monomer location in the oligomer ADP1-3. For example, in formula 1B, the R variables selected from R7 and R8 may independently be selected from those side chains or monomers shown in Tables 1 and/or 2 for the specific peptoid ADP-1 as C; and so on for ADP2 (E, or F) and ADP3 (I).

In formula 1C—R10, R11, R12, and R14 may additionally be selected from those groups shown in Tables 1 and 2 for the equivalent letter designations that are provided for the particular peptoid monomer location in the oligomer ADP1-3. For example, in formula 1C, the R variables selected from R7 and R8 may independently be selected from those side chains or monomers shown in Tables 1 and/or 2 for the specific peptoid ADP-1 as A, B or C; and so on for ADP2 (D, E, or F) and ADP3 (G, H, or I).

In formula 1D, R21, R22, R23, and R24, may additionally be selected from those groups shown in Tables 1 and 2 for the equivalent letter designations that are provided for the particular peptoid monomer location in the oligomer ADP1-3. For example, in formula 1D, the R variables selected from R7 and R8 may independently be selected from those side chains or monomers shown in Tables 1 and/or 2 for the specific peptoid ADP-1 as A, B or C; and so on for ADP2 (D, E, or F) and ADP3 (G, H, or I).

In the formulas described herein Z is a coupling group that can include one or more amino acids or functional groups; L is an optional linker moiety, M is a substrate or support or label; and m, n, o, and/or p is 0-6.

Methods also can include (b) detecting antibodies bound to said peptoid.

In certain aspects, a peptoid as described herein can comprise a terminal functional group, at either the carboxy or amino terminus; the functional group will be capable of being coupled to a support, a linker moiety, a label, or other moieties. In certain aspect a terminal cysteine residue is coupled to the peptoid and can provide a sulfhydryl group for further coupling the peptoid to a substrate. In other aspects, the carboxy terminus can comprise an $NH_2$, OH, or other chemical group that can be further reacted with a substrate (directly or indirectly) or a linker or other moiety.

A wide variety of linkers can be used. The linker component in its simplest form is a bond between the peptoid and a second moiety, such as a substrate or other molecular entity. More generally, the linker will provide a mono- or multi-molecular skeleton covalenty or non-covalently linking one or more peptoid to one or more substrates or molecular moieties. Thus, linking of a peptoid described herein to a desired substrate or moiety can be achieved by covalent or non-covalent means, usually involving interaction with one or more functional groups located on the peptoid and/or substrate or second molecular entity. Examples of chemically reactive functional groups which may be employed for this purpose include amino, hydroxyl, sulfhydroxyl, carboxyl and carbonyl groups, as well as carbohydrate groups, vicinal diols, thioethers, 2-aminoalcohols, 2-aminothiols, guanidinyl, imidazolyl and phenolic groups.

The methods may further comprise obtaining a sample from a subject. The method may also further comprise making a diagnosis of Alzheimer's Disease for a subject from which said sample was obtained if antibody binding to said peptoid is greater than that observed for control non-diseased patients. In still a further aspect, the methods can further comprising prescribing a particular drug or therapy for a subject.

In certain embodiments, a peptoid may be selected from the group consisting of AD1 (APD1), AD2 (APD2) and AD3 (APD3), wherein Z is as described above. The sample may be contacted with more than one peptoid of formulas 1A-1D, for example, such as three structurally distinct peptoids (e.g., AD1, AD2 and AD3).

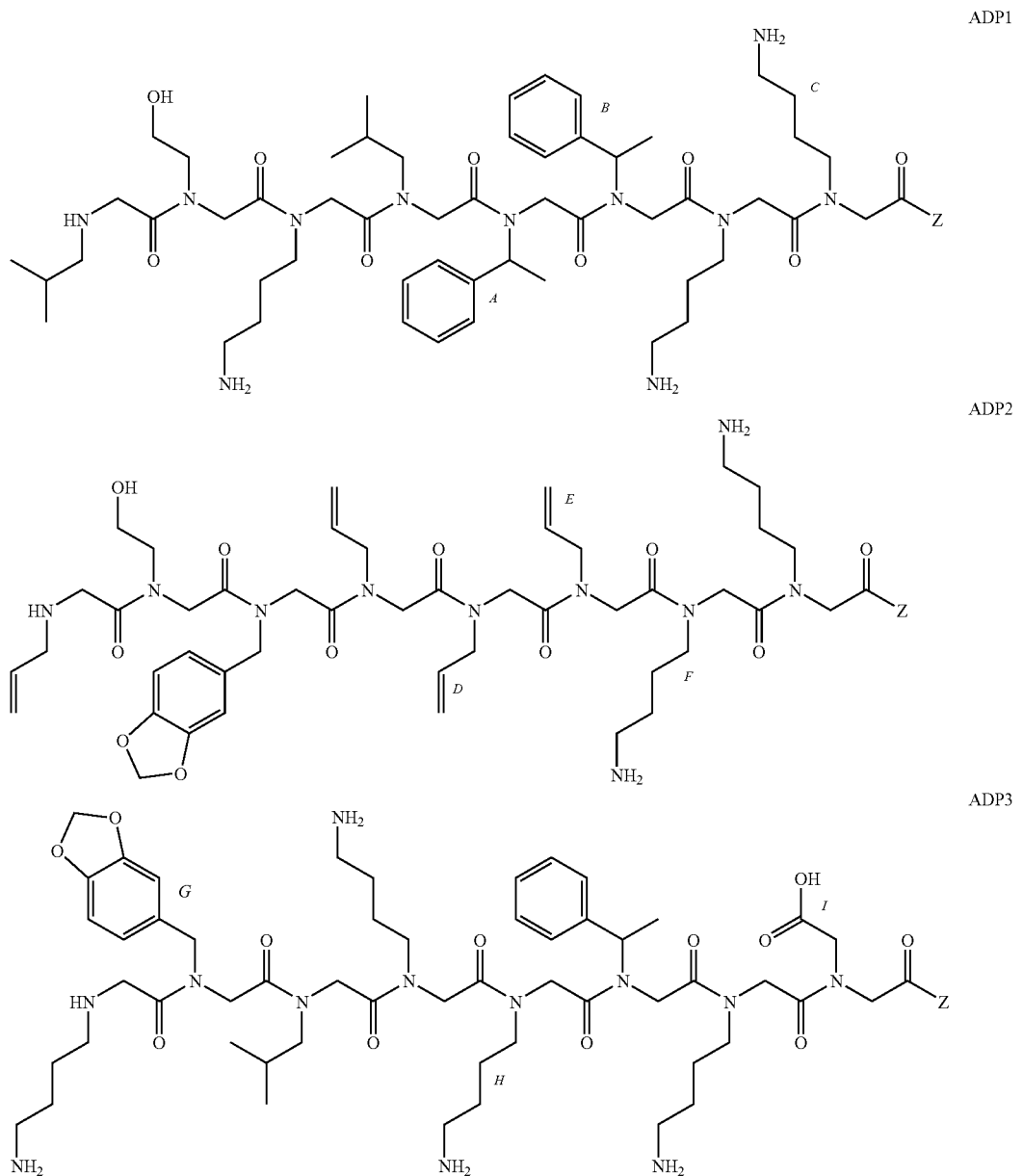

In certain aspects, the support may be a bead, a plate, a dipstick, a filter, a membrane a pin, or a well. The sample may be blood, serum, saliva or CSF. The detecting step may comprise RIA, FIA, ELISA, Western blot, flow cytometry, FRET, or surface plasmon resonance.

In certain aspects, a peptoid of the invention can comprise one of the following formulas:
(i) $(X)_{0-4}$(methylbenzyl)(methylbenzyl)(n-butylamine)(n-butylamine)
(ii) $(X)_{0-4}$(allyl)(allyl)(n-butylamine)(X), or
(iii) $(X)$(piperonyl)$(X)_{0-2}$(n-butylamine)$(X)_{0-2}$(glycine);
wherein X can be hydrogen; alkyl; allyl; methyl; ethyl; n-propyl; isopropyl; n-butyl; isobutyl; n-butylamine; sec-butyl; tert-butyl; pentyl; hexyl; isopentyl; or hydroxyl group.

Embodiments include peptoids of 2, 3, 4, 5, 6, 7, 8 or more monomer units. In certain aspects a peptoid can comprise a peptoid sequence from position 1, 2, 3, 4, 5, 6 to position 8 or from position 8, 7, 6, 5, 4, 3, 2 to position 1, or any 2, 3, 4, 5, 6, 7 monomer peptoid there between.

The monomers can comprise various combinations of R groups, for example hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_1$-$C_6$ alkyl unsubstituted or substituted with $NH_2$, OH, or SH; $C_2$-$C_6$ alkynyl unsubstituted or substituted with $NH_2$, OH, or SH; lysyl; carboxyl; or hydroxyl group—including one or more chemical group described in Table 1 and 2 below. In a preferred embodiment, the monomeric amines or amino acids are selected from glycine, cysteine, allylamine, ethanolamine, isobutylamine, diaminobutane, methylbenzylamine, piperonylamine, 4(2-aminoethyl)benzenesulfonamide, furfurylamine, benzylamine, 3-methoxypropylamine (MPOA), 2-methoxyethylamine and cyclohexylamine amine. Such monomers may be used in any combination to form oligomers of 3-12 mer length.

In certain aspects certain monomer units of the ADP1, ADP2, and/or ADP3 formula can be selected groups and at specific positions as provided in Tables 1-3. The most preferred embodiments are those specific compounds shown as ADP1, ADP2, ADP3 and further include those active compounds identified in the sarcosine scan which identified specific monomers designated at positions A-I on the structures shown above for ADP1-3. Tables 1 and 2 below provide these letter designations in the left hand column for specific positions on ADP1-3 which can additionally have the side chains shown in Table 1 (using the amines with said side chains) or the replacement amines shown in Table 2 and at such specific preferred positions. Residues A through I in structures APD1, APD2, and APD3 can also be substituted with groups independently selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{1-6}$ alkyl unsubstituted or substituted with $NH_2$, OH, or SH; $C_{2-6}$ alkynyl unsubstituted or substituted with $NH_2$, OH, or SH; lysyl; carboxyl—including one or more chemical group described in Table 1 and 2 below. $R^2$, $R^3$ and $R^5$ are independently selected from the group consisting of $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl.

TABLE 1

Side chain modifications for peptoids

| Replacement Amine Position | Amine Side Chain, $NH_2R$ (Ref. No.) |
|---|---|
| D, E | n-Bu[1] (Heine, Tetrahedron 59 (2003) 9919-9930) |
| D, E | s-Bu |
| I | —Cy |
| A, B, G | —CH$_2$CH$_2$—CH(Ph)$_2$ |
| A, B, G | —CH$_2$Ph |
| C, F, H | —CH$_2$CH$_2$OH |
| C, F, H | —OH |
| A, B, G | (4-OPh-phenyl-methyl) |
| A, B, G | (4-OH-phenyl-methyl) |
| A, B, G | (4-OH-phenylethyl, branched) |
| C, F, H | (neopentyl diol, CH$_2$OH, CH$_2$OH) |
| C, F, H | (alkyl chain with NHBoc, n = 0-4) |
| I | (alkyl chain with C(O)Ot-Bu, n) |
| H, I | (alkyl chain with C(O)NH$_2$, n) |
| A, B, G | (indol-3-yl-ethyl) |
| A, B, G | (imidazol-4-yl-ethyl) |
| A, B, G | (thiazol-2-yl) |
| A, B, G | (thiophen-2-yl-methyl) |
| C, F, H | —i-Bu |
| I | —CH$_2$Cy |
| C, F, H | (tetrahydrofuran-2-yl-methyl) |

TABLE 1-continued

Side chain modifications for peptoids

| Replacement Amine Position | Amine Side Chain, NH₂R (Ref. No.) |
|---|---|
| A, B, G | —CH2OClPh |
| A, B, G | —CH₂pOCH₃Ph |
| A, B, G | —CHCH₃Ph |
| C, F, H | —CH₂CH₂CH₂NHBoc |
| A, B, G | 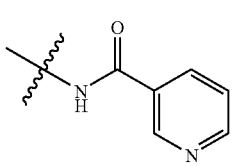 [SMILES: *NC(=O)c1cccnc1] |
| C, F, H | —CH₂CH₂OMe |
| C, F, H | —CH₂CH₂CH₂OH |
| C, F, H | —CH(CH₃)CH₂OH |
| C, F, H | —CH₂CHOHCH₂OH |
| A, B, G | —CH₂CH(OH)Ph |
| A, B, G | 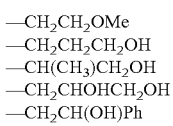 |

(Kirshenbaum etal JACS Nov. 17, 2008)

| | |
|---|---|
| A, B, G | 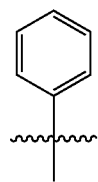 |
| A, B, G | 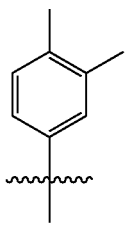 [SMILES: *c1ccc(C)c(C)c1] |
| A, B, G | 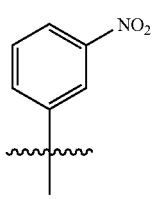 [SMILES: *c1cccc([N+](=O)[O-])c1] |
| A, B, G | 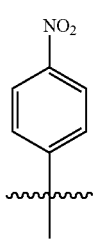 [SMILES: *c1ccc([N+](=O)[O-])cc1] |
| A, B, G | 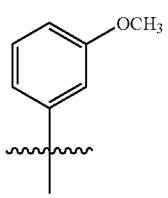 [SMILES: *c1cccc(OC)c1] |

TABLE 1-continued

Side chain modifications for peptoids

| Replacement Amine Position | Amine Side Chain, NH₂R (Ref. No.) |
|---|---|
| A, B, G | 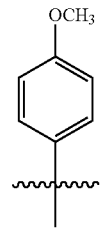 |
| A, B, G | 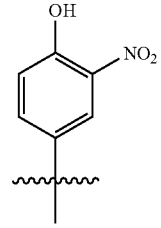 [SMILES: *c1ccc(O)c([N+](=O)[O-])c1] |
| A, B, G | 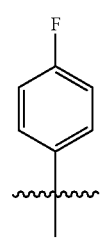 [SMILES: *c1ccc(F)cc1] |
| A, B, G | 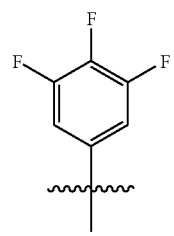 [SMILES: *c1cc(F)c(F)c(F)c1] |
| A, B, G | 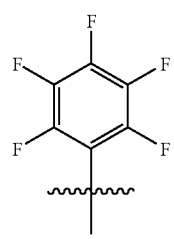 [SMILES: *c1c(F)c(F)c(F)c(F)c1F] |
| A, B, G | 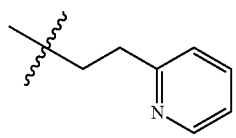 |

(Disney et. al. Acs Chem. Biol. Mar. 11, 2009)

| | |
|---|---|
| A, B, G, C, F, G | 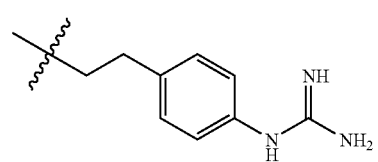 [SMILES: *CCc1ccc(NC(=N)N)cc1] |

TABLE 1-continued

Side chain modifications for peptoids

| Replacement Amine Position | Amine Side Chain, NH$_2$R (Ref. No.) |
|---|---|
| A, B, G | 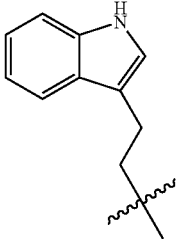 [SMILES: *CCc1c[nH]c2ccccc12] |
| C, F, G | 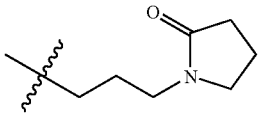 [SMILES: *CCCN1CCCC1=O] |
| A, B, G | 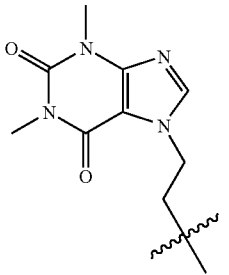 [SMILES: *CCn1cnc2c1c(=O)n(C)c(=O)n2C] |
| C, F, H | 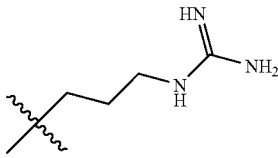 [SMILES: *CCCNC(=N)N] |
| A, B, D, E, G | 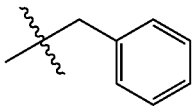 [SMILES: *Cc1ccccc1] |
| A, B, G, C, F, H | 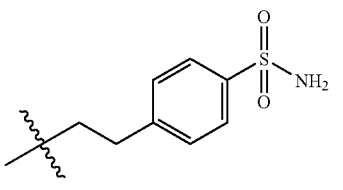 [SMILES: *CCc1ccc(S(N)(=O)=O)cc1] |
| C, F, H | —nPr |
| C, F, H | 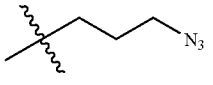 [SMILES: *CCCN=[N+]=[N-]] |
| A, B, G | 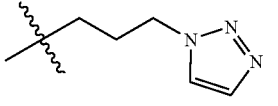 [SMILES: *CCCn1ccnn1] |
| C, F, H | —CH$_2$CH$_2$CH$_2$OMe (Blackwell et al. Organic Letters 2005 vol 7 (8) 1521-24) |

TABLE 1-continued

Side chain modifications for peptoids

| Replacement Amine Position | Amine Side Chain, NH$_2$R (Ref. No.) |
|---|---|
| A, B, C, D, E, F, G, H | 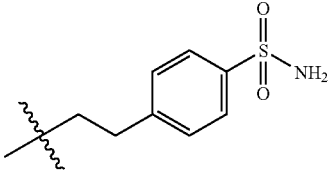 [SMILES: *CCc1ccc(S(N)(=O)=O)cc1] |
| C, F, H | 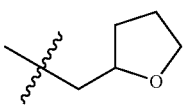 [SMILES: *CC1CCCO1] |
| A, B, G | 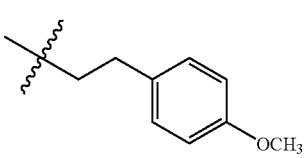 [SMILES: *CCc1ccc(OC)cc1] |
| A, B, G | 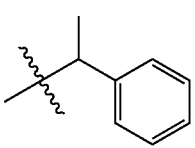 [SMILES: *C(C)c1ccccc1] |
| A, B, G | 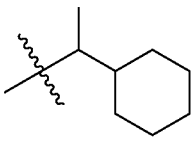 [SMILES: *C(C)C1CCCCC1] |
| A, B, G | 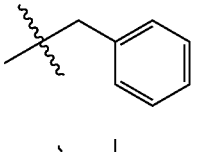 |
| A, B, G | 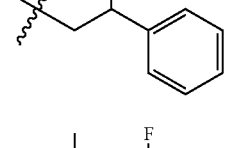 |
| A, B, G | 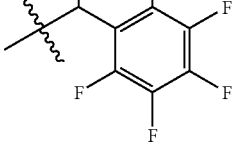 |
| A, B, G | 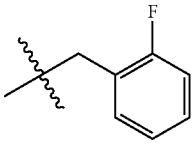 [SMILES: *Cc1ccccc1F] |
| A, B, G | 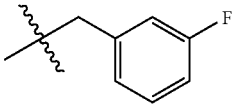 |

TABLE 1-continued
Side chain modifications for peptoids
| Replacement Amine Position | Amine Side Chain, NH$_2$R (Ref. No.) |
|---|---|
| A, B, G | 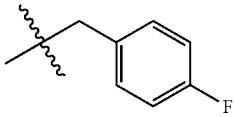 [SMILES: *Cc1ccc(F)cc1] |
| A, B, G | 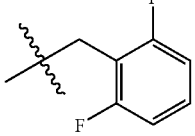 |
| A, B, G | 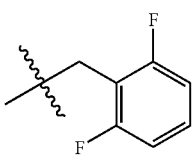 [SMILES: *Cc1c(F)cccc1F] |
| A, B, G | 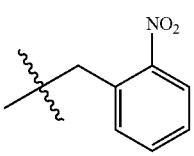 [SMILES: *Cc1ccccc1[N+](=O)[O-]] |
| A, B, G | 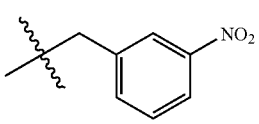 [SMILES: *Cc1cccc([N+](=O)[O-])c1] |
| A, B, G | 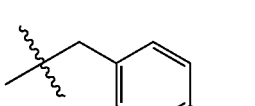 |
| A, B, G | 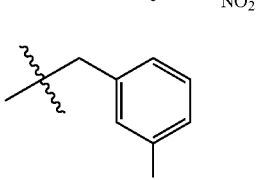 |
| A, B, G | 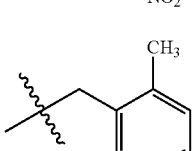 |
| A, B, G | 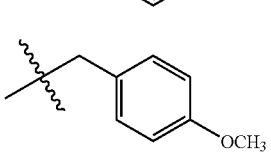 |
| A, B, G | 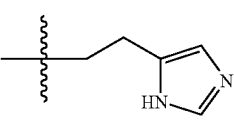 |
(Burkoth et al. JACS 2003, 125, 8841-8845)
TABLE 1-continued
Side chain modifications for peptoids
| Replacement Amine Position | Amine Side Chain, NH$_2$R (Ref. No.) |
|---|---|
| A, B, G | 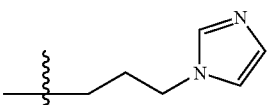 |
| A, B, G | 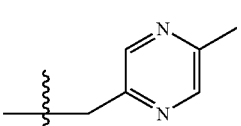 |
| A, B, G | 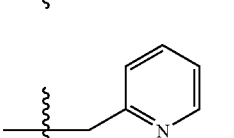 |
| A, B, G | 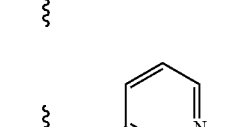 |
| A, B, G | 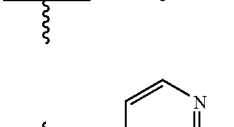 |
| A, B, G | 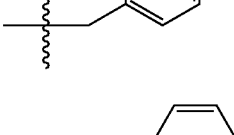 |
| A, B, G | 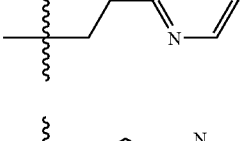 |
| A, B, G | 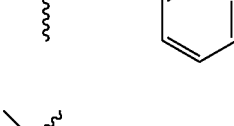 |
| A, B, C, F, G, H | 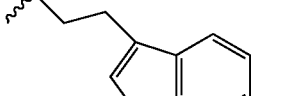 |

TABLE 1-continued

Side chain modifications for peptoids

| Replacement Amine Position | Amine Side Chain, NH$_2$R (Ref. No.) |
|---|---|
| A, B, G | 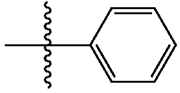 |
| C, F, G | 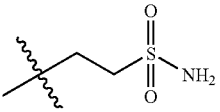 (Appella et al. JACS, 2006, 128(6), 1995-2004) |
| C, F, H, I | 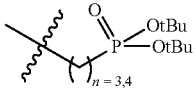 |
| C, F, H | 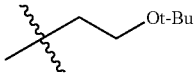 [SMILES: *CCOC(C)(C)C] |
| A, B, G | 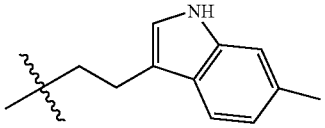 [SMILES: *CCc1c[nH]c2cc(C)ccc12] |
| G, A, B | 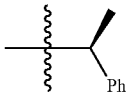 |
| A, B, G | 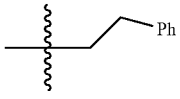 [SMILES: *CCc1ccccc1] |
| C, F, H, I | 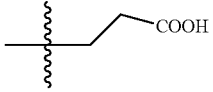 [SMILES: *CCC(=O)O] |
| A, B, G | 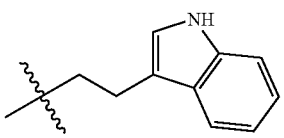 [SMILES: *CCc1c[nH]c2ccccc12] |
| C, F, H | 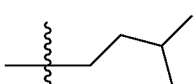 |
| C, F, H, I | 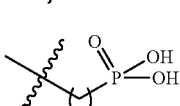 |
| A, B, G | 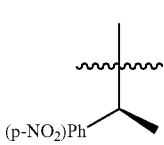 |
| NA | —CH$_3$ |

TABLE 1-continued

Side chain modifications for peptoids

| Replacement Amine Position | Amine Side Chain, NH$_2$R (Ref. No.) |
|---|---|
| A, B, C, F, G, H | 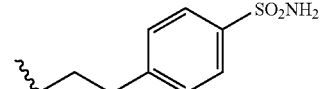 |
| Is C, F or H | 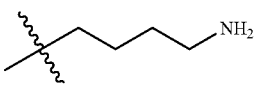 [SMILES: *CCCCN] |
| A, B, G | 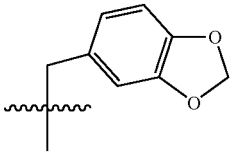 [SMILES: *Cc1ccc2c(c1)OCO2] |
| C, F, H | —CH$_2$CH$_2$OH |

TABLE 2

A listing of amines that can be used in synthesizing peptoids described herein.

| Replacement Amine Position | Amine Side Chain, NH$_2$R (Ref. No.) |
|---|---|
| A, B, G | 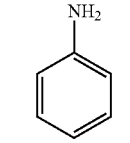 |
| A, B, G | 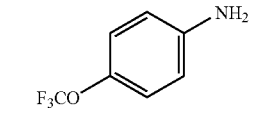 [SMILES: Nc1ccc(OC(F)(F)F)cc1] |
| A, B, G | 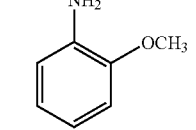 |
| A, B, G | 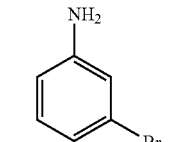 |
| A, B, G | 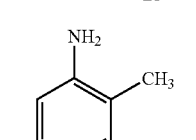 |
| A, B, G | 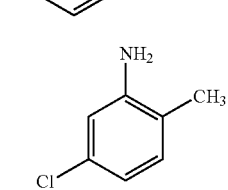 |

TABLE 2-continued
A listing of amines that can be used in synthesizing peptoids described herein.
| | |
|---|---|
| A, B, G | 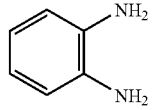 |
| A, B, G | 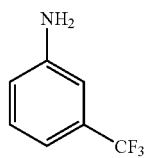 |
| A, B, G | 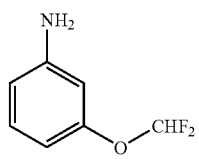 [SMILES: Nc1cccc(OC(F)F)c1] |
| A, B, G | 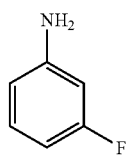 |
| A, B, G | 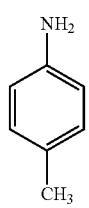 |
| A, B, G | 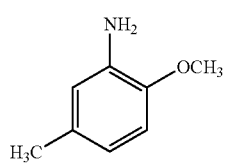 |
| A, B, G | 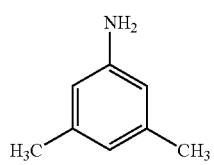 |
| A, B, G | 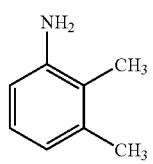 |
| A, B, G | 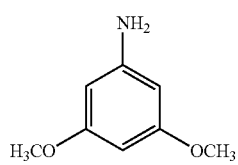 [SMILES: COc1cc(N)cc(OC)c1] |
| A, B, G | 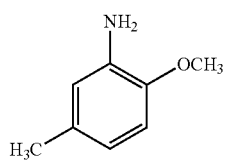 |
| A, B, G | 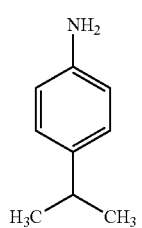 |
| A, B, G | 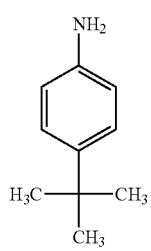 |
| A, B, G | 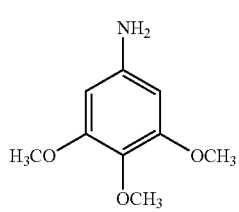 |
| A, B, G, C, F, H | 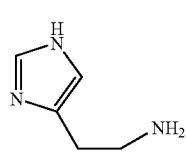 |
| A, B, G | 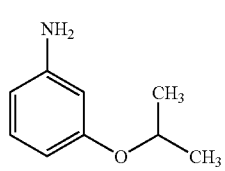 |
| A, B, G | 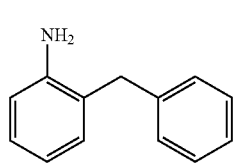 [SMILES: Nc1ccccc1Cc1ccccc1] |
| A, B, G | 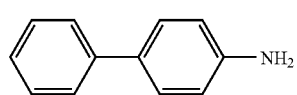 |

TABLE 2-continued
A listing of amines that can be used in synthesizing peptoids described herein.
| | |
|---|---|
| A, B, G |  |
| A, B, G | 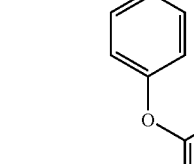 |
| A, B, G | 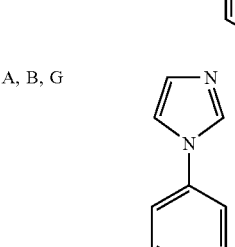 |
| A, B, G | 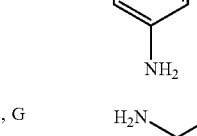 |
| A, B, G | 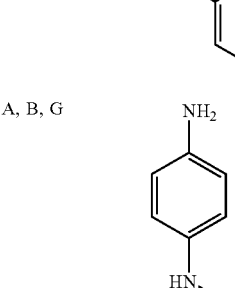 |
| A, B, G | 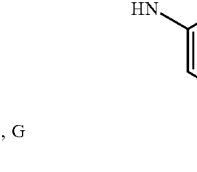 |
| A, B, G | 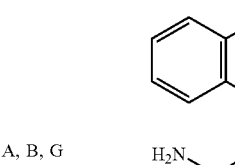 |
| A, B, G |  |
| A, B, G |  |
| A, B, G |  |
| A, B, G |  |
| A, B, G |  |
| A, B, G |  |
| A, B, G |  |
| A, B, D, E, G |  |
| A, B, D, E, G |  |
| D, E |  |
| A, B, G |  |

TABLE 2-continued
A listing of amines that can be used in synthesizing peptoids described herein.
| | |
|---|---|
| A, B, G | 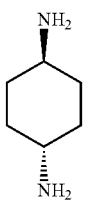 |
| A, B, G | 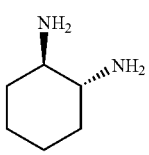 |
| A, B, G | 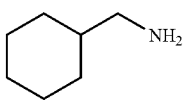 |
| A, B, G | 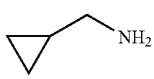 |
| C, F, H | 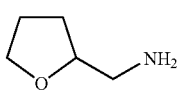 |
| A, B, G | 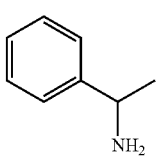 |
| A, B, G | 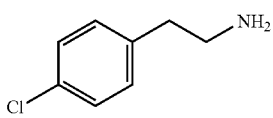 |
| A, B, G | 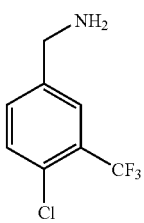 [SMILES: NCc1ccc(Cl)c(C(F)(F)F)c1] |
| A, B, G | 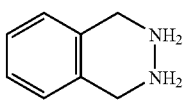 |
| A, B, G | 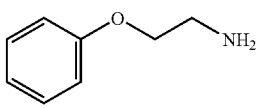 |
| A, B, G | 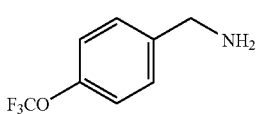 |
| A, B, G | 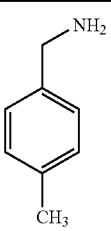 |
| A, B, G | 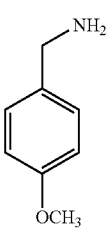 |
| A, B, G | 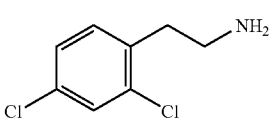 [SMILES: NCCc1ccc(Cl)cc1Cl] |
| A, B, G | 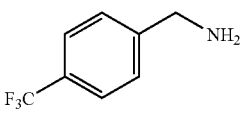 |
| A, B, G | 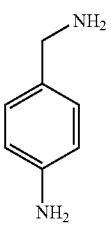 |
| A, B, G | 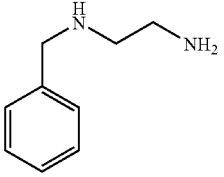 [SMILES: NCCNCc1ccccc1] |
| A, B, G | 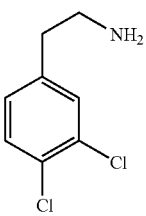 [SMILES: NCCc1ccc(Cl)c(Cl)c1] |
| A, B, G | 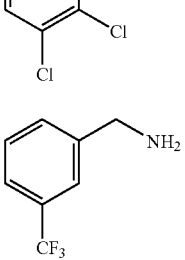 |

TABLE 2-continued
A listing of amines that can be used in synthesizing peptoids described herein.
| | |
|---|---|
| A, B, G | 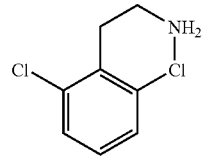 |
| A, B, G | 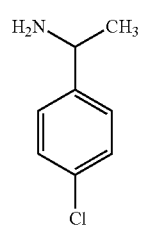 |
| A, B, D, E, G | 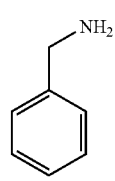 |
| A, B, G | 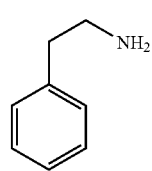 |
| A, B, G | 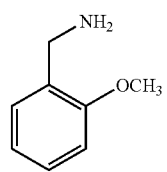 |
| A, B, G | 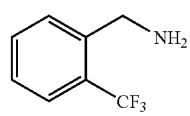 |
| A, B, G, C, F, G | 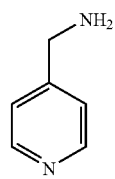 |
| A, B, G | 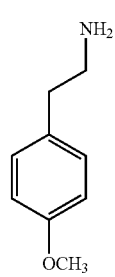 [SMILES: COc1ccc(CCN)cc1] |
| A, B, G | 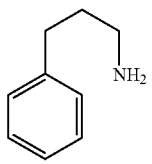 |
| A, B, G | 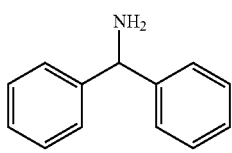 [SMILES: NC(c1ccccc1)c1ccccc1] |
| A, B, G | 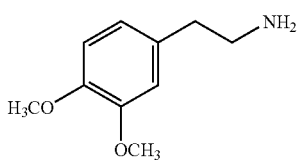 [SMILES: COc1ccc(CCN)cc1OC] |
| A, B, G | 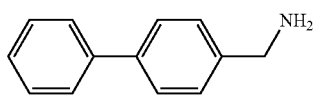 [SMILES: NCc1ccc(-c2ccccc2)cc1] |
| A, B, G | 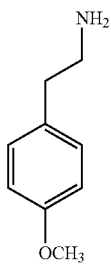 |
| A, B, G | 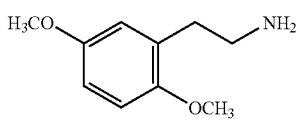 [SMILES: COc1ccc(OC)c(CCN)c1] |
| A, B, G | 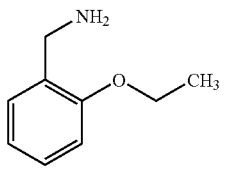 |
| A, B, G | 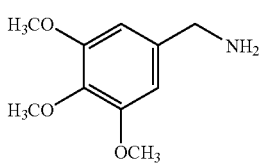 [SMILES: COc1cc(CN)cc(OC)c1OC] |
| A, B, G | 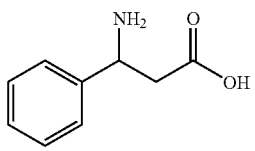 [SMILES: NC(CC(=O)O)c1ccccc1] |

TABLE 2-continued
A listing of amines that can be used in synthesizing peptoids described herein.
| | |
|---|---|
| A, B, G | 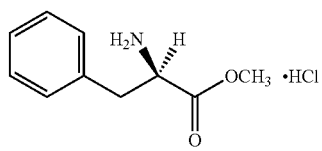 [SMILES: COC(=O)[C@H](N)Cc1ccccc1 ; Cl] |
| A, B, G | 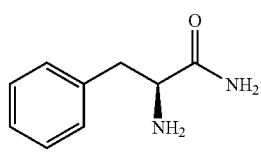 [SMILES: NC(=O)[C@@H](N)Cc1ccccc1] |
| A, B, G | 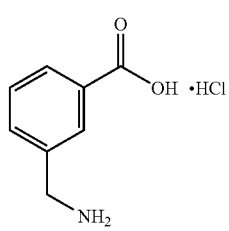 [SMILES: NCc1cccc(C(=O)O)c1 ; Cl] |
| A, B, G | 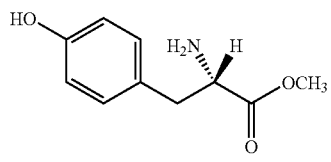 [SMILES: COC(=O)[C@@H](N)Cc1ccc(O)cc1] |
| A, B, G | 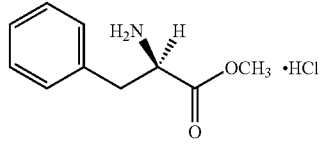 [SMILES: COC(=O)[C@H](N)Cc1ccccc1 ; Cl] |
| A, B, G | 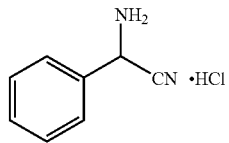 |
| A, B, G | 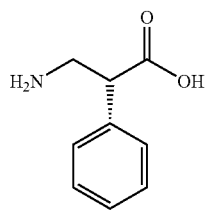 |
| A, B, G | 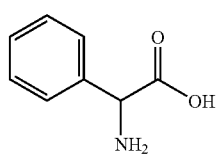 |
| A, B, G | 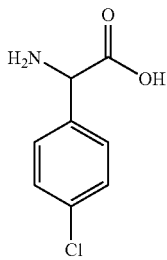 [SMILES: NC(C(=O)O)c1ccc(Cl)cc1] |
| A, B, G | 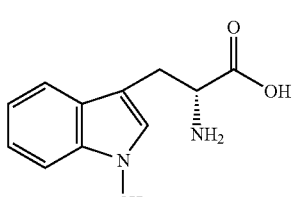 |
| A, B, G | 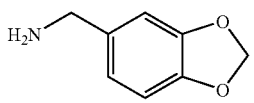 |
| A, B, G | 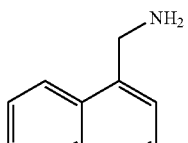 |
| A, B, G | 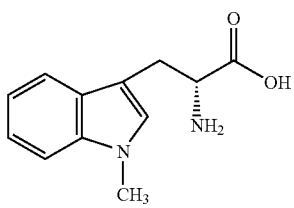 [SMILES: Cn1cc(C[C@@H](N)C(=O)O)c2ccccc21] |
| C, F, H | 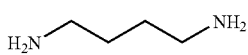 |
| C, F, H | 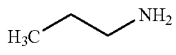 |
| C, F, H | $CH_3OOCH_2CH_2NH_2$ |
| C, F, H |  |
| C, F, H | 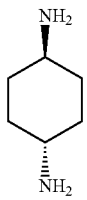 |

TABLE 2-continued
A listing of amines that can be used in synthesizing peptoids described herein.
| | |
|---|---|
| C, F, H | 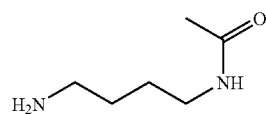 |
| C, F, H | 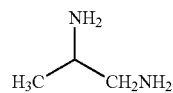 |
| C, F, H | H$_2$N-CH$_2$CH$_2$-NH$_2$ |
| C, F, H | CH$_3$(CH$_2$)$_4$CH$_2$NH$_2$ |
| C, F, H | 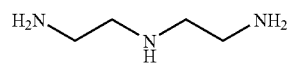 |
| C, F, H | NH$_2$CH$_2$CH$_2$CH$_2$NHCH$_3$ |
| C, F, H |  |
| C, F, H | 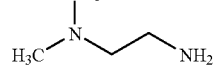 |
| C, F, H | 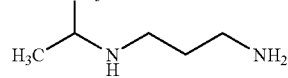 |
| C, F, H | 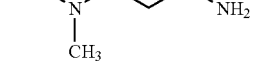 |
| C, F, H | 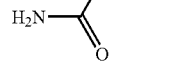 |
| C, F, H | 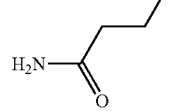 |
| C, F, H | 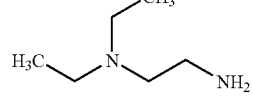 |
| C, F, H |  |
| C, F, H | 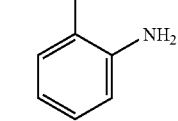 |
| C, F, H | 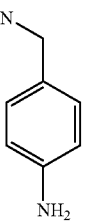 |
| C, F, H | 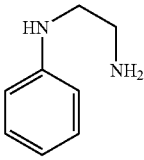 |
| D, E | 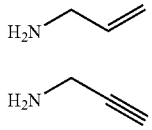 |
| D, E |  |
| D, E | 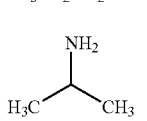 |
| D, E | CF$_3$CH$_2$NH$_2$ |
| D, E | 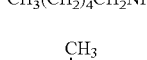 |
| D, E | CH$_3$(CH$_2$)$_4$CH$_2$NH$_2$ |
| D, E |  |
| D, E | 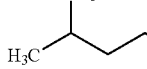 |
| D, E | 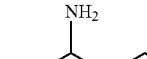 |
| I | 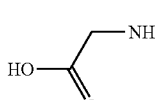 |
| I | 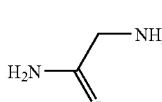 |
| I | 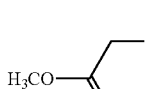 |
| I | Any amino acid |

TABLE 2-continued
A listing of amines that can be used in synthesizing peptoids described herein.
| | | | | |
|---|---|---|---|---|
| A, B, G | 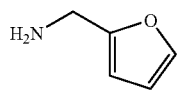 | | D, E | 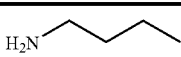 |
| A, B, G | 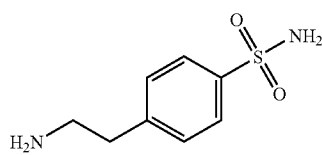 | | A, B, G, D, E | 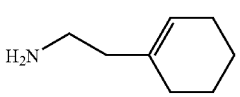 |
| C, F, H | 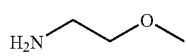 | | A, B, G | 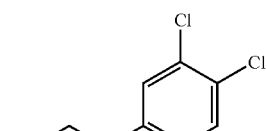 |
| C, F, H | 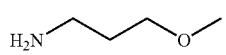 | | | |
| C, F, H | 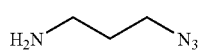 | | A, B, G | 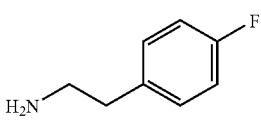 |
| C, F, H | 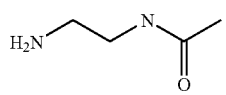 | | | |
| C, F, H | 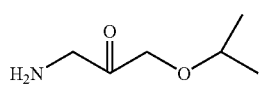 | | A, B, G | 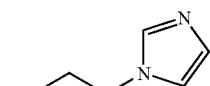 |
| C, F, H | 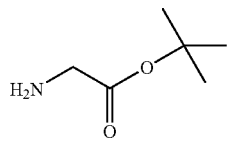 | | I | 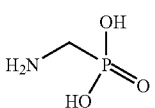 |
| C, F, H | 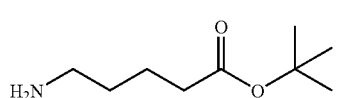 | | C, F, H | 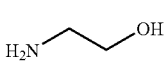 |
| A, B, G | 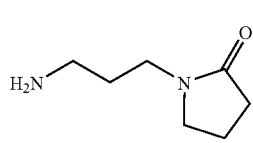 | | A, B, G | 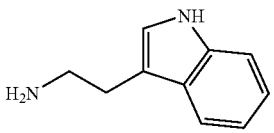 |
| A, B, G | 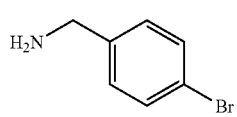 | | A, B, G | 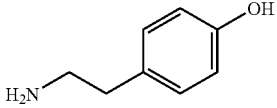 |
| A, B, G | 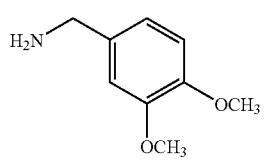 | | A, B, G | 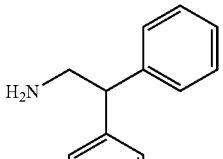 |
| A, B, G | 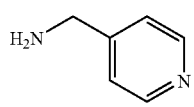 | | A, B, G | 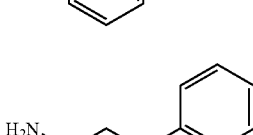 |
| A, B, G | 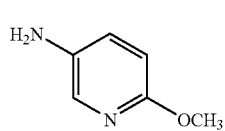 | | | 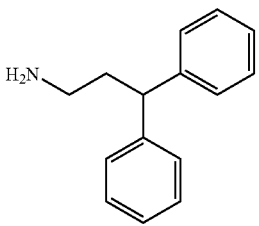 [SMILES: NCCC(c1ccccc1)c1ccccc1] |

TABLE 2-continued

A listing of amines that can be used in synthesizing peptoids described herein.

| | |
|---|---|
| A, B, G | 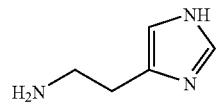 |
| A, B, G | 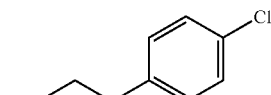 |
| A, B, G | 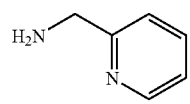 |
| A, B, G | 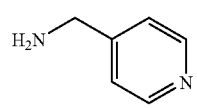 |
| C, F, H | 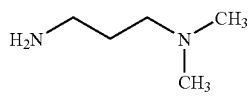 |
| A, B, G | 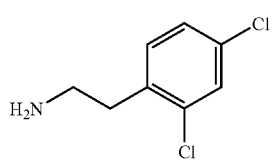 [SMILES: NCCc1ccc(Cl)cc1Cl] |
| l | 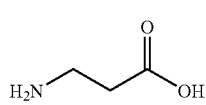 |

TABLE 3

Alzheimer's disease compounds

| | Position 1 | Position 2 | Position 3 | Position 4 | Position 5 | Position 6 | Position 7 | Position 8 |
|---|---|---|---|---|---|---|---|---|
| 1 | Isobutyl | Ethanol | N-butyl amine | Isobutyl | Methylbenzyl | Methylbenzyl | N-butyl amine | N-butyl amine |
| 2 | Allyl | Ethanol | Piperonyl | Allyl | Allyl | Allyl | N-butyl amine | N-butyl amine |
| 3 | N-butyl amine | Piperonyl | Isobutyl | N-butyl amine | N-butyl amine | Methylbenzyl | N-butyl amine | Glycine |
| 4 | Methyl | Ethanol | N-butyl amine | Isobutyl | Methylbenzyl | Methylbenzyl | N-butyl amine | N-butyl amine |
| 5 | Methyl | Ethanol | Piperonyl | Allyl | Allyl | Allyl | N-butyl amine | N-butyl amine |
| 6 | Methyl | Piperonyl | Isobutyl | N-butyl amine | N-butyl amine | Methylbenzyl | N-butyl amine | Glycine |
| 7 | Isobutyl | Methyl | N-butyl amine | Isobutyl | Methylbenzyl | Methylbenzyl | N-butyl amine | N-butyl amine |
| 8 | Allyl | Methyl | Piperonyl | Allyl | Allyl | Allyl | N-butyl amine | N-butyl amine |
| 9 | Isobutyl | Ethanol | Methyl | Isobutyl | Methylbenzyl | Methylbenzyl | N-butyl amine | N-butyl amine |
| 10 | Allyl | Ethanol | Methyl | Allyl | Allyl | Allyl | N-butyl amine | N-butyl amine |
| 11 | N-butyl amine | Piperonyl | Methyl | N-butyl amine | N-butyl amine | Methylbenzyl | N-butyl amine | Glycine |
| 12 | Isobutyl | Ethanol | N-butyl amine | Methyl | Methylbenzyl | Methylbenzyl | N-butyl amine | N-butyl amine |
| 13 | Allyl | Ethanol | Piperonyl | Methyl | Allyl | Allyl | N-butyl amine | N-butyl amine |
| 14 | N-butyl amine | Piperonyl | Isobutyl | Methyl | N-butyl amine | Methylbenzyl | N-butyl amine | Glycine |
| 15 | Allyl | Ethanol | Piperonyl | Allyl | Methyl | Allyl | N-butyl amine | N-butyl amine |
| 16 | N-butyl amine | Piperonyl | Isobutyl | N-butyl amine | Methyl | Methylbenzyl | N-butyl amine | Glycine |
| 17 | Allyl | Ethanol | Piperonyl | Allyl | Allyl | Methyl | N-butyl amine | N-butyl amine |
| 18 | N-butyl amine | Piperonyl | Isobutyl | N-butyl amine | N-butyl amine | Methyl | N-butyl amine | Glycine |
| 19 | Isobutyl | Ethanol | N-butyl amine | Isobutyl | Methylbenzyl | Methylbenzyl | Methyl | N-butyl amine |
| 20 | Allyl | Ethanol | Piperonyl | Allyl | Allyl | Allyl | Methyl | N-butyl amine |
| 21 | N-butyl amine | Piperonyl | Isobutyl | N-butyl amine | N-butyl amine | Methylbenzyl | Methyl | Glycine |
| 22 | Allyl | Ethanol | Piperonyl | Allyl | Allyl | Allyl | N-butyl amine | Methyl |

TABLE 4

Parkinson's disease compounds.

| | Position 1 | Position 2 | Position 3 | Position 4 | Position 5 | Position 6 | Position 7 | Position 8 |
|---|---|---|---|---|---|---|---|---|
| 1 | N-butyl amine | N-butyl amine | Allyl | N-butyl amine | Methylbenzyl | Methylbenzyl | N-butyl amine | Isobutyl |
| 2 | Allyl | N-butyl amine | Ethanol | Isobutyl | Ethanol | Allyl | N-butyl amine | N-butyl amine |
| 3 | Piperonyl | Allyl | Ethanol | Allyl | N-butyl amine | Allyl | N-butyl amine | Allyl |

In another embodiment, there is provided peptoids that bind antibodies indicative of Parkinson's disease and methods of detecting antibodies in an antibody-containing sample comprising (a) contacting an antibody-containing sample with a support having affixed thereto a peptoid having the formula:

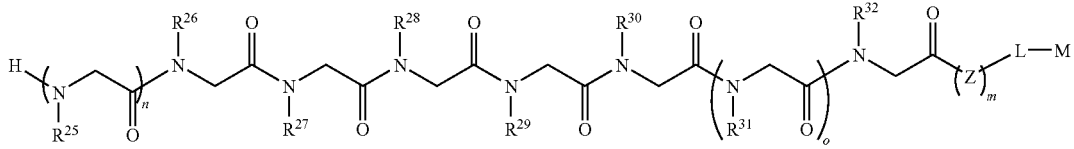

In one embodiment, $R^{27}$ is an alkylaryl group. In certain aspects, $R^{27}$ is methylbenzyl group. $R^{25}$, $R^{26}$, $R^{28}$-$R^{32}$ of formula 2A are independently selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2. In certain aspects, $R^{26}$, $R^{29}$, $R^{31}$ and/or $R^{32}$ is/are an alkylamine, for example N-butylamine. In still a further aspect, $R^{30}$ is an alkenyl, such as an allyl group.

2B are independently selected from the group consisting of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Table 1 and 2.

In the formulas described herein Z is coupling group that can include one or more amino acids or functional groups; L is an optional linker moiety, M is a substrate or support or label; and m, n, o, and/or p is 0-6.

In certain aspects the methods can also include (b) detecting antibodies bound to said peptoid.

The method may further comprise obtaining said sample from a subject. The method may also further comprise making a diagnosis of Parkinson's Disease for a subject from which said sample was obtained if antibody binding to said peptoid is greater than that observed for control non-diseased patients. In still a further aspect, the methods can include prescribing a drug or therapy to a subject.

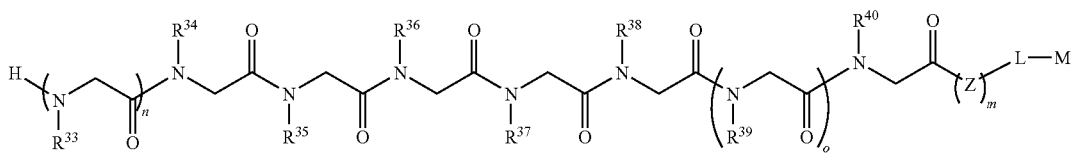

In another embodiment, a peptoid may have formula 2B, wherein, $R^{34}$ is an alkylamine, for example N-butylamine. In still another embodiment $R^{35}$ is an alkenyl, such as an allyl group. In certain embodiments, $R^{37}$ an alkoxy group such ethanol. In certain aspects, $R^{33}$, $R^{36}$ and $R^{38}$-$R^{40}$ of formula In certain embodiments, a peptoid may be selected from the group consisting of PD1, PD2 and PD3. The sample may be contacted with one or more peptoids of formulas 2A-2B, such as three structurally distinct peptoids (e.g., PD1, PD2 and PD3).

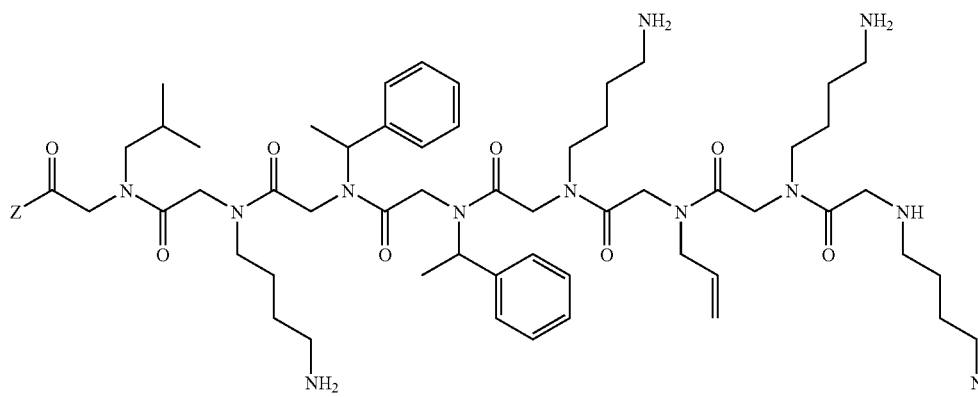

PD1

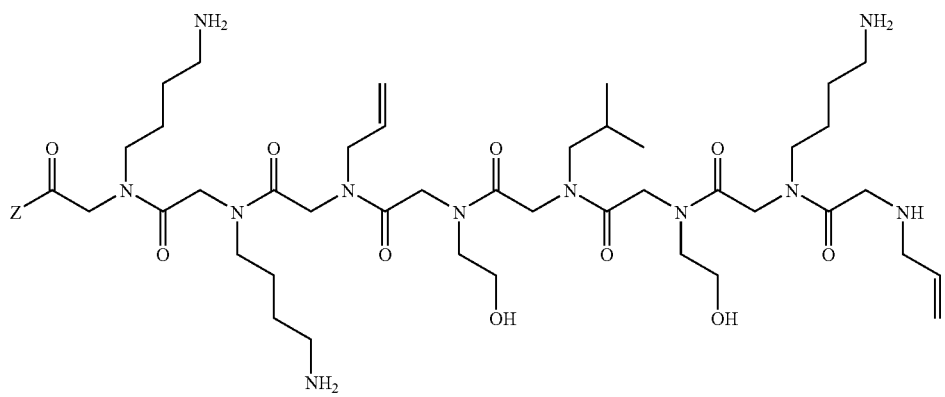

PD2

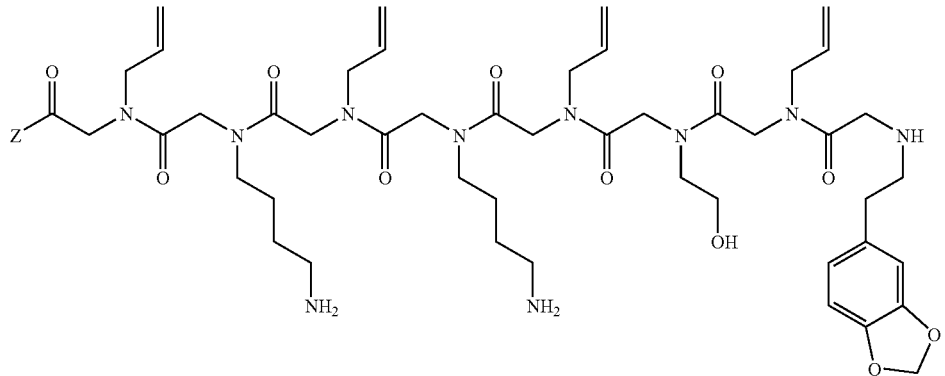

PD3

In certain aspects, the support may be a bead, a plate, a dipstick, a filter, a membrane a pin, or a well. The sample may be blood, serum, saliva or CSF. Detecting may comprise RIA, FIA, ELISA, Western blot, flow cytometry, FRET, or surface plasmon resonance.

In yet another embodiment, there is provided a method of treating a subject suspected of having a neurodegenerative disease (ND) comprising (a) contacting an antibody-containing sample from said subject with one or more supports having affixed thereto a peptoid comprising a dipeptoid unit having the formula (1A), formula (1B), formula (1C), formula (1D), formula (2A) and/or formula (2B), (b) detecting antibodies bound to said peptoids; and (c) making a treatment decision based on the result of step (b). The method may further comprise obtaining said sample from a subject. The method may also further comprise making a diagnosis of Parkinson's Disease for a subject from which said sample was obtained if antibody binding to the PD peptoid is greater than that observed for control non-diseased patients, or making a diagnosis of Alzheimers's Disease for a subject from which said sample was obtained if antibody binding to the AD peptoid is greater than that observed for control non-diseased patients. The method may also further comprise making a treatment decision for said subject. The sample may be contacted with more than one peptoid of formulas 1A-1D and/or 2A-2B. The sample may be contacted with three structurally distinct peptoids that react with antibodies for each of PD and AD. The support may be a bead, a plate, a dipstick, a filter, a membrane a pin, or a well. The sample may be blood, serum, saliva or CSF. Detecting may comprise RIA, FIA, ELISA, Western blot, flow cytometry, FRET, or surface plasmon resonance.

In further embodiments, neurodegenerative diseases include, but are not limited to Alzheimer's disease; Parkinson's disease; multiple sclerosis (MS); amyotrophic lateral sclerosis (ALS or Lou Gehrig's disease); dementia; motor neuron disease; prion disease; Huntington's disease; Tauopathies; Chromosome 17 dementias; hereditary neuropathies; and diseases involving cerebellar degeneration.

A further embodiment is directed to an antibody composition isolated from a biological fluid that is indicative of a neurodegenerative disease. In certain embodiments the antibody are isolated by contacting a sample having such antibodies with a peptoid composition that specifically binds antibodies indicative or associated with a neurdenerative disease. The antibodies can be removed, isolated, or purified from other non-antibody and non-ND specific components. The antibodies can then be washed and/or disassociated from the peptoid capture agent(s).

In certain embodiments, a peptoid array is hybridized with a biological sample that has been supplemented with a bacterial lysate, e.g., an E. coli lysate. The biological sample includes a control sample and a sample having a marker for a central nervous system disorder. For example, microarray slides are covered with a hybridization chamber and equilibrated with 1×TBST (50 mM Tris, pH 8.0, 150 mM NaCl, 0.1% Tween20) for about 15 minutes. The slides are then blocked with a bacterial lysate at a concentration at least, at most, or about 0.5, 1, 1.5, 2 mg/ml of lysate. The lysate is removed and the slides are incubated with about a milliliter of biological sample (having a an approximate protein concentration of 5, 10, 15, 20 or 25 µg/ml including all ranges and values there between) in bacterial lysate with gentle shaking. Microarrays are then washed with 1×TBST and hybridized with labeled Anti-IgG antibodies (e.g., at 1:400 dilution). The slides are then washed with an appropriate buffer. The slides are dried using a centrifuge (e.g., 5 min spin at 1500 rpm) and scanned on a microarray scanner, for example, using a 635-nm laser at 100% power and a 600 or 650 photomultiplier tube gain. The present invention thus also relates to a method of reducing background antisera noise in a diagnostic assay comprising treating the control plasma sample and the diseased sample with an E. coli lysate and contacting said samples with a peptoid or ligand array. It is believed that this process can be used to support treatment of any array used to detect and distinguish antibodies in sera in the context of comparing a control sample to a diseased sample.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Peptoids AD1-AD3 identify Alzheimer's Disease antibodies. (FIG. 1B) Peptoids PD1-PD3 identify Parkinson's Disease antibodies. Z represents a functional group that can be further coupled to a substrate, linker, or second molecular entity.

(FIG. 2A) Serum antibody-binding profiles for peptoids AD1-AD3. (FIG. 2B) Serum antibody-binding profiles for peptoids PD1-PD3. (FIG. 2C) Serum antibody binding profiles for ADPD1-ADPD3.

FIG. 7 Validation of an intermediate subject AD12 after 5 years.

FIG. 8 The Luminex® Titration of Alzheimer's Disease Vs Normal Control. (FIG. 8A) Autopsy confirmed AD sample vs normal control. (FIG. 8B) AD5 vs NC9. (FIG. 8C) AD8 vs NC11. (FIG. 8D) Autopsy confirmed AD sample vs normal control pool.

(FIG. 9A) Two different normal controls vs normal control pool. (FIG. 9B) AD8 vs NC11. (FIG. 9C) Autopsy confirmed AD sample vs normal control pool.

DESCRIPTION OF ILLUSTRATIVE EMBODIMENTS

I. Neurodegenerative Diseases

Figure 1A:
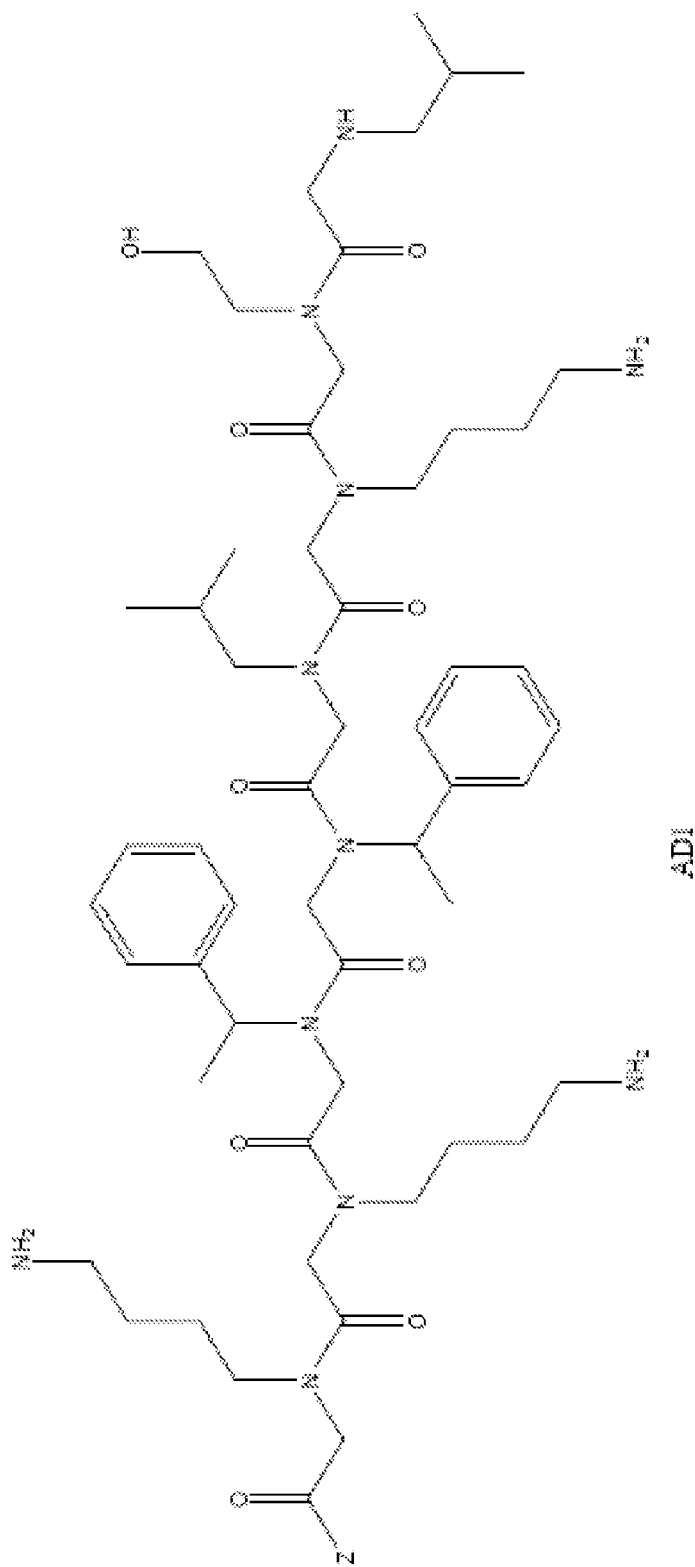
FIGS. 1A-B—Structures of Peptoids Found to Capture Disease Specific Antibodies.
Figure 1A:
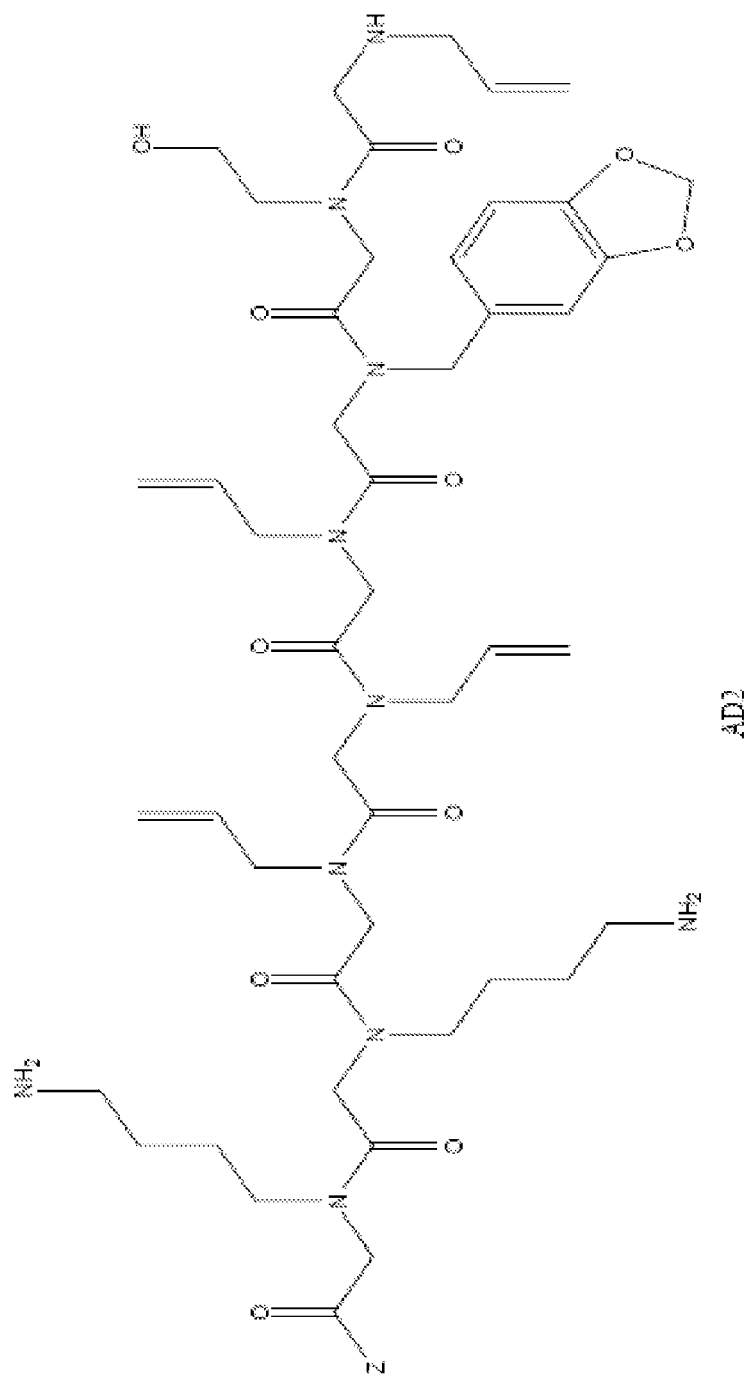
Figure 1A:
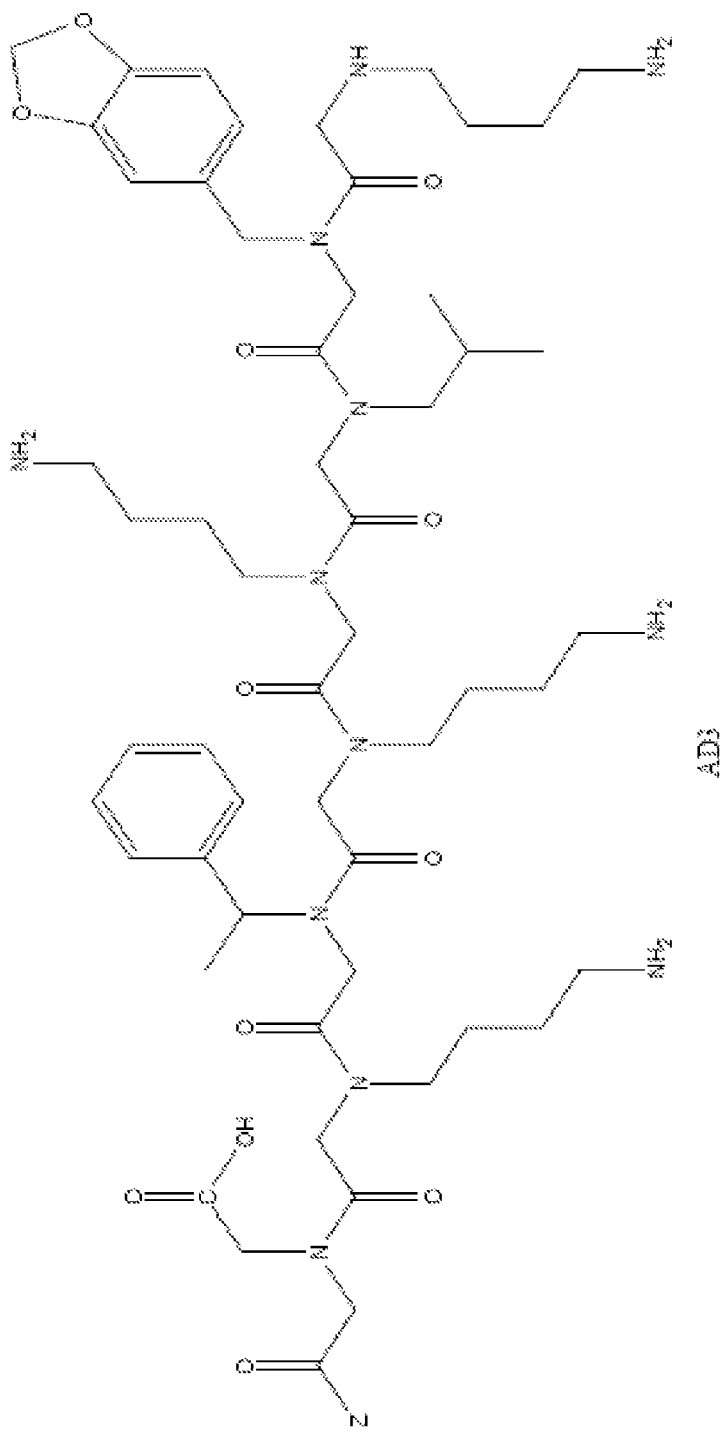
Figure 1B:
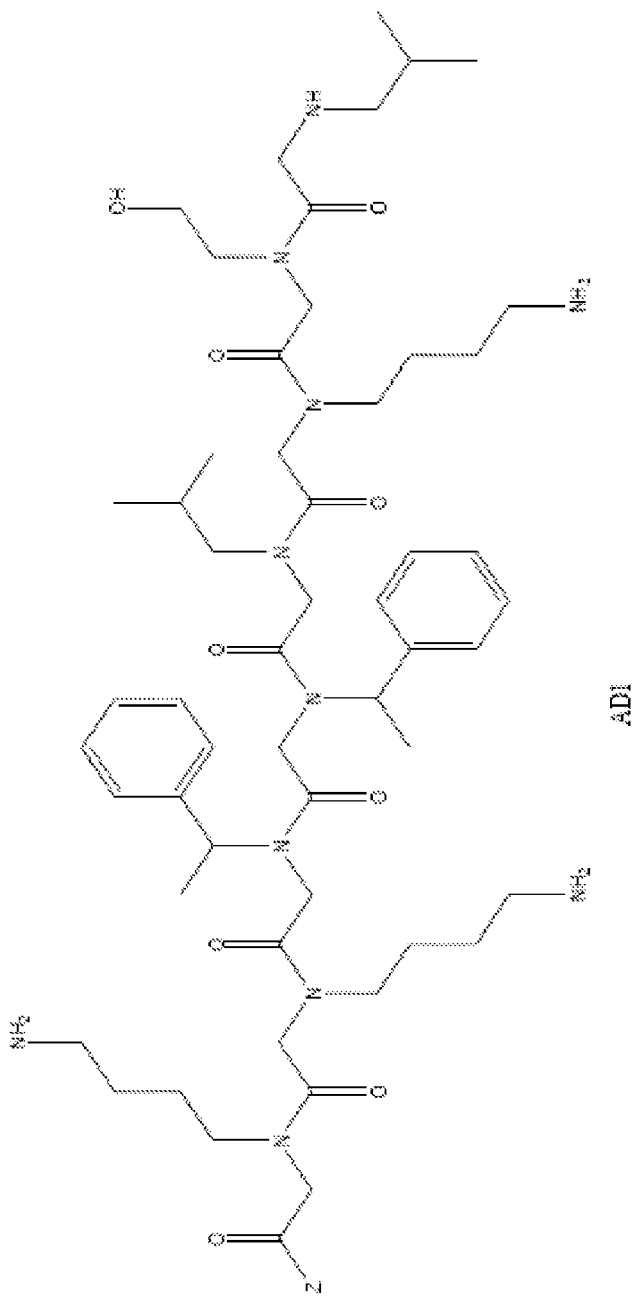
Figure 1B:
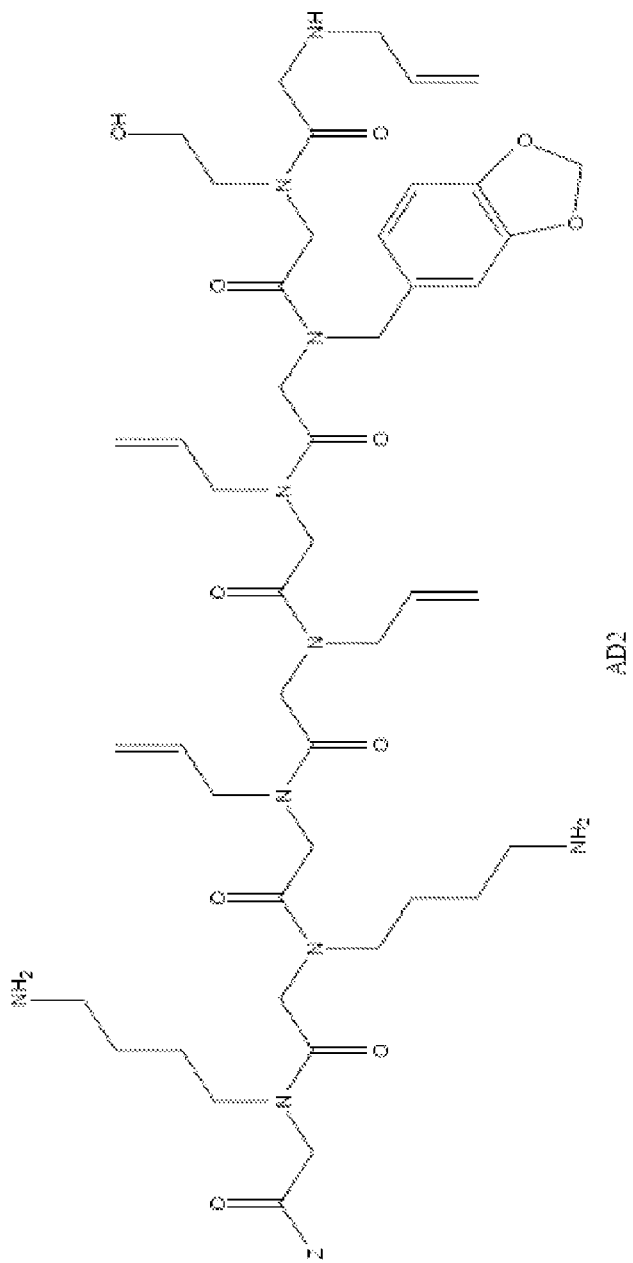
Figure 1B:
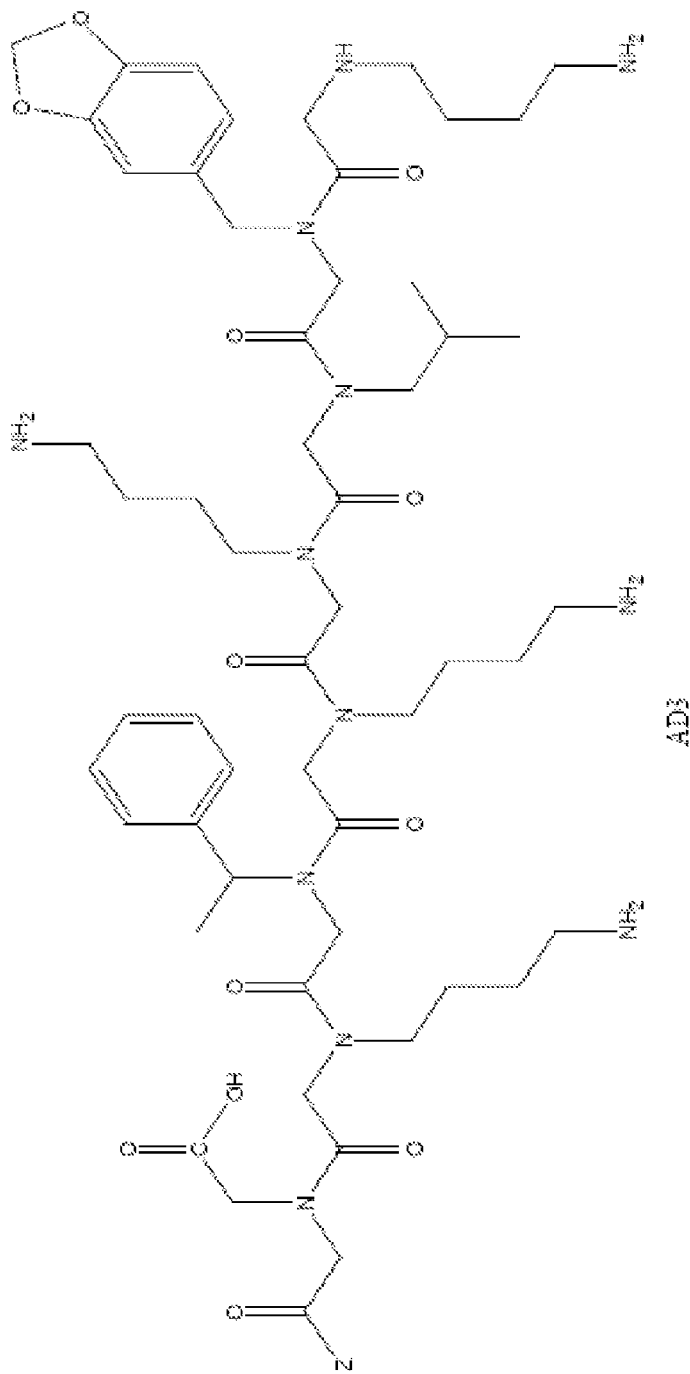

Neurodegenerative Diseases (NDs) include a wide variety of debilitating afflictions of the central and peripheral nervous systems. Most, however, affect the CNS. Such diseases include Alzheimer's Disease, Pick's Disease, senile dementia, Parkinson's Disease, multiple sclerosis, multiple system atrophy, dementia with Lewy bodies, Huntingon's Disease, Progressive Supranuclear Palsy, Creutzfeldt-Jakob Disease, amyotrophic lateral sclerosis, dementia, motor neuron disease, prion disease, Huntington's disease, Tauopathies, Chromosome 17 dementias, hereditary neuropathies, and diseases involving cerebellar degeneration.

Because there usually is no single definitive test for these disease, and because of the overlapping symptoms that many of these disease exhibit, doctors waste weeks and millions of dollars running tests for "rule out" purposes that ultimately provide little or no diagnostic benefit. As such a simple and accurate test is greatly needed.

The inventors have identified a number of small molecule "peptoids" that are specific ligands for antibodies produced uniquely in subjects having either Parkinson's Disease or Alzheimer's Disease. Peptoids, or N-substituted oligo-glycines, are a specific subclass of Peptidomimetic. They are closely related to their natural Peptide counterparts, but differ chemically in that their side chains are appended to Nitrogen atoms along the molecule's backbone, rather than to the α-carbons (as they are in amino acids). Because of the exquisite selectivity these peptoids exhibit for disease-specific antibodies, it is now possible to provide a definitive diagnosis for at least some PD and AD subjects using a simple immuno-based assay that is both inexpensive and simple to use. These and other aspects of the invention are set forth in detail below.

A. Parkinson's Disease

Parkinson's Disease (PD) is one of a group of conditions classified as movement disorders. It is both chronic and progressive. Parkinson's disease occurs when cells of the substantia nigra begin to malfunction and eventually die. This results in the loss of dopamine production, a chemical messenger that transports signals to the parts of the brain that control movement initiation and coordination. The primary symptoms are tremors, rigidity or stiffness of the limbs and trunk, bradykinesia or slowness of movement, and postural instability or impaired balance and coordination. Secondary symptoms included speech changes, loss of facial expression, difficulty swallowing, drooling, pain, dementia or confusion, sleep disturbances, depression, fear or anxiety, memory difficulties, urinary problems, fatigue and aching, and loss of energy. However, symptoms vary, and the disease progression may be rapid or not.

Upwards of one million Americans suffer from PD. While approximately 15% of patients are diagnosed before the age of 40, incidence increases with age. The cause is unknown, and although there is presently no cure, there are many treatment options such as medication and surgery to manage the symptoms. The degree of success of each treatment varies among individuals, as does the length of time the treatment option remains effective.

Levodopa is a dopamine precursor, which was considered a breakthrough in the treatment of PD. Unfortunately, patients experienced debilitating side effects, including severe nausea and vomiting, and with increased dosing and prolonged use, patients experienced other side effects including dyskinesias. Sinemet (Levodopa+Carbidopa) represented a significant improvement in that the addition of carbidopa prevents levodopa from being metabolized in the gut, liver and other tissues, allowing more of it to get to the brain. Thus, a smaller dose of levodopa is needed, and the severe nausea and vomiting was greatly reduced.

Stalevo (carbidopa+levodopa+entacapone) is combination tablet for patients who experience signs and symptoms of end-of-dose "wearing-off." The tablet combines carbidopa/levodopa with entacapone. While carbidopa reduces the side effects of levodopa, entacapone extends the time levodopa is active in the brain (up to 10% longer).

Symmetrel (amantadine hydrochloride) activates both the release of dopamine from storage sites, and possibly blocks the re-uptake of dopamine into nerve terminals. It also has a glutamate receptor blocking activity. Its dopaminergic actions result in its usefulness in reducing dyskinesia induced by levodopa and is thus called an indirect-acting dopamine agonist, and is widely used as an early monotherapy, and with the more powerful Sinemet added when needed.

Anticholinergics (trihexyphenidyl, benztropine mesylate, procyclidine, etc.) do not act directly on the dopaminergic system. Instead they act to decrease the activity of another neurotransmitter, acetylcholine. There is a complex interaction between levels of acetylcholine in the brain and levels of dopamine. Many clinicians find that if an agonist or levodopa does not relieve tremor, then the addition of an anticholinergic drug is often effective. Adverse effects include blurred vision, dry mouth and urinary retention. These drugs may be contraindicated in older patients since they can cause confusion and hallucination.

Other drugs include Selegiline or deprenyl (Eldepryl), which have has been shown to delay the need for Sinemet when prescribed in the earliest stage of PD. Dopamine agonists are drugs that activate dopamine receptors directly, and can be taken alone or in combination with Sinemet. Such agonists include bromocriptine (Parlodel), pergolide (Permax), pramipexole (Mirapex) and ropinirole (Requip). COMT inhibitors such as tolcapone (Tasmar) and entacapone (Comtan) prolong the duration of symptom relief by blocking the action of an enzyme which breaks down levodopa.

Surgery is an option for some patients after medications are no longer satisfactory. A patient should discuss surgery thoroughly with his or her neurologist before making any decision. Two older lesioning procedures are pallidotomy and thalamotomy. Pallidotomy can alleviate rigidity and bradykinesia symptoms, and thalamotomy helps to control tremors. Doctors rarely perform either procedure because both permanently destroy parts of the brain and have serious side effects. The damage could make it impossible to perform surgeries that may become available in the future, such as brain tissue transplants.

Deep brain stimulation (DBS) is safer and more effective, and thus has replaced these methods. It is a preferred surgical option because it has the same, if not better, results than pallidotomy and thalamotomy. DBS also leaves open the possibility of other therapies, should they become available in the future. As with any surgical procedure, there are risks and side effects. The main benefit of DBS surgery is to reduce motor fluctuations, i.e., the ups and downs caused by a decreasing effectiveness of Sinemet. The electrode is usually placed on one side of the brain. The DBS electrode implanted in the left side of the brain will control the symptoms on the right side of the body and vice versa. In some cases, patients will need to have stimulators on both sides of the brain.

B. Alzheimer's Disease

Dementia is a brain disorder that seriously affects a person's ability to carry out daily activities. Alzheimer's disease (AD) is the most common form of dementia among older people. Scientists believe that up to 4 million Americans suffer from AD. The disease usually begins after age 60, and risk goes up with age. While younger people also may get AD, it is much less common. About 3 percent of men and women ages 65 to 74 have AD, and nearly half of those age 85 and older may have the disease. While the subject of intensive research, the precise causes of AD are still unknown, and there is no cure.

AD attacks parts of the brain that control thought, memory and language. It was named after Dr. Alois Alzheimer, a German doctor. In 1906, Dr. Alzheimer noticed changes in the brain tissue of a woman who had died of an unusual mental illness. He found abnormal clumps (now called amyloid plaques) and tangled bundles of fibers (now called neurofibrillary tangles). Today, these plaques and tangles in the brain are considered hallmarks of AD.

Scientists also have found other brain changes in people with AD. There is a loss of nerve cells in areas of the brain that are vital to memory and other mental abilities. There also are lower levels of chemicals in the brain that carry complex messages back and forth between nerve cells. Thus, AD may disrupt normal thinking and memory by inhibiting, both physically and chemically, the transfer of message between nerve cells.

AD is progressive, characterized by memory loss, language deterioration, impaired visuospatial skills, poor judgment, indifferent attitude, but preserved motor function. As mentioned, AD usually begins after age 65, but its onset may occur as early as age 40, appearing first as memory decline and, over several years, destroying cognition, personality, and ability to function. Confusion and restlessness may also occur. The type, severity, sequence, and progression of mental changes vary widely. The early symptoms of AD, which include forgetfulness and loss of concentration, can be missed easily because they resemble natural signs of aging. Similar symptoms can also result from fatigue, grief, depression, illness, vision or hearing loss, the use of alcohol or certain medications, or simply the burden of too many details to remember at once.

There is no cure for AD and no way to slow the progression of the disease. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. Also, some medications may help control behavioral symptoms such as sleeplessness, agitation, wandering, anxiety, and depression. These treatments are aimed at making the patient more comfortable.

The course of the disease varies from person to person. Some people have the disease only for the last 5 years of life, while others may have it for as many as 20 years. The most common cause of death in AD patients is infection.

The molecular aspect of AD is complicated and not yet fully defined. As stated above, AD is characterized by the formation of amyloid plaques and neurofibrillary tangles in the brain, particularly in the hippocampus which is the center for memory processing. Several molecules contribute to these structures: amyloid β protein (Aβ), presenilin (PS), cholesterol, apolipoprotein E (ApoE), and Tau protein. Of these, Aβ appears to play the central role.

Aβ contains approximately 40 amino acid residues. The 42 and 43 residue forms are much more toxic than the 40 residue form. Aβ is generated from an amyloid precursor protein (APP) by sequential proteolysis. One of the enzymes lacks sequence specificity and thus can generate Aβ of varying (39-43) lengths. The toxic forms of Aβ cause abnormal events such as apoptosis, free radical formation, aggregation and inflammation.

Presenilin encodes the protease responsible for cleaving APP into Aβ. There are two forms—PS1 and PS2. Mutations in PS1, causing production of $A\beta_{42}$, are the typical cause of early onset AD.

Cholesterol-reducing agents have been alleged to have AD-preventative capabilities, although no definitive evidence has linked elevated cholesterol to increased risk of AD. However, the discovery that Aβ contains a sphingolipid binding domain lends further credence to this theory.

Similarly, ApoE, which is involved in the redistribution of cholesterol, is now believed to contribute to AD development. Individuals having the ϵ4 allele, which exhibits the least degree of cholesterol efflux from neurons, are more likely to develop AD.

Tau protein, associated with microtubules in normal brain, forms paired helical filaments (PHFs) in AD-affected brains which are the primary constituent of neurofibrillary tangles. Recent evidence suggests that Aβ proteins may cause hyperphosphorylation of Tau proteins, leading to disassociation from microtubules and aggregation into PHFs.

For AD, drugs have been used to limit the progression of the disease and to alleviate or improve certain of the associated symptoms. These drug generally fit into the broad categories of cholinesterase inhibitors, muscarinic agonists, anti-oxidants or anti-inflammatories. Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, memric, quetiapine, neurestrol and neuromidal are just some of the drugs proposed as therapeutic agents for AD.

II. Diagnostic/Prognostic/Therapeutic Determinations in Neurodegenerative Diseases The present invention, for the first time, provides a definitive diagnosis for disease like Alzheimer's Disease and Parkison's Disease. This permits doctors the confidence of knowing that they have correctly identified the underlying physiologic basis for a patient's symptoms, thereby opening up early intervention and disease management.

Because treatments for AD primarily slow but do not prevent disease, and some treatments for PD act in the same fashion, the ability to provide an early diagnosis for these diseases is critical to delaying the onset of more severe symptoms. This will also preserve the quality of life and extend the survival of these patients. In addition, being able to provide patients with the correct drugs to address their symptoms without "trial and error" that sometimes results from incorrect diagnosis, will significantly reduce the cost of care, and avoid patient discomfort and possible harm.

These assays will all rely on the use of an antibody-containing patient sample. The most commonly utilized biological sample will be blood or serum due to the prevalence of antibodies therein. However, other samples such as tear, saliva, sputum, cerebrospinal fluid, semen or urine may prove useful as well.

In assessing the levels of antibodies in the subject, the observed levels will be compared to a standard. The standard may rely on known values established for both disease and normal subjects, and may therefore obviate the need for the user to provide anything but a reaction control, i.e., a control showing that the reagents and conditions necessary for a positive reaction are present. Alternatively, one may choose to run an actual control which comprises a similar sample from an actual person of known healthy or diseased status. In addition, one may run a series of samples from the same subject over time looking for a trend of increasing PD or AD antibody levels as an indication of disease progression.

III. Antibody-Based Diagnostic Assays

As discussed above, applications of this assay are to (a) identify patients whose serum antibody profile puts them at risk of developing or having ND; (b) identify patients whose symptoms are such that they may or may not be suffering from ND (i.e., provide a definitive diagnosis of ND); (c) assess the impact of an ND therapy; and (d) monitor ND progression.

The detection methods for the present invention will be similar to those for antibody-based detection, and thus include formats like enzyme linked immunosorbent assay (ELISA), radioimmunoassay (RIA), immunoradiometric assay, fluoroimmunoassay, chemiluminescent assay, bioluminescent assay, FACS, FRET and Western blot to mention a few. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining an antibody-containing sample, contacting the sample with a peptoid in accordance with the present invention under conditions effective to allow the formation of peptoid-antibody complexes, and detecting antibody bound to the peptoid.

The peptoid will typically be linked to a solid support, such as in the form of a column matrix, bead, filter, membrane, stick, plate, or well and the sample will be applied to the immobilized peptoid. The unwanted components will be washed from the support, leaving antibodies complexed with the peptoid, which are then detected using various means, such as subsequent addition of anti-Fc antibodies that are linked to a detectable moiety.

Contacting the chosen biological sample with the peptoid under effective conditions and for a period of time sufficient to allow the formation of peptoid-antibody complexes is generally a matter of simply contacting the sample with the peptoid and incubating the mixture for a period of time long enough for the antibodies to bind peptoids. After this time, the sample-peptoid composition, such as a an ELISA plate, dot blot or Western blot, will generally be washed to remove any non-specifically bound antibody species, allowing only those antibodies specifically bound to the immobilized antibody-peptoid complexes to be detected.

In general, the detection of peptoid-antibody complex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

Various other formats are contemplated and are well known to those of skill in the art. Discussed below are three particular assays envisioned to have ready applicability to the present invention.

A. ELISAs

Immunoassays, in their most simple and direct sense, are binding assays. Certain immunoassays finding particular use in the present invention are various types of enzyme linked immunosorbent assays (ELISAs) and radioimmunoassays (RIA) known in the art.

In one exemplary ELISA, the peptoids of the invention are immobilized onto a selected surface, such as a well in a polystyrene microtiter plate. Then, a test composition suspected of containing the antibody is added to the wells. After binding and washing to remove non-specifically bound complexes, the bound antibody may be detected. Detection may be achieved by the addition of another peptoid linked to a detectable label. This type of assay is analogous to a simple "sandwich ELISA" except that binding of the labeled agent is direct at the Fab portion of the bound antibody. Detection may also be achieved by the addition of a labeled antibody that binds any bound antibody, e.g., that recognizes the Fc portion of the bound antibody. Optionally, this antibody is not labeled, and is followed by the addition of a second antibody that has binding affinity for the first antibody, with the second antibody being linked to a detectable label.

In another exemplary ELISA, the samples suspected of containing the antibodies are immobilized onto a well surface and then contacted with labeled peptoids of the present invention. After binding and washing to remove non-specifically bound immune complexes, the bound labeled peptoids are detected. Alternatively, the peptoids are not labeled and can be detected against an artificial antibody (non-sample) that is selected for specific binding the peptoid of choice, this second would be linked to a detectable label, thereby permitting detection.

Irrespective of the format employed, ELISAs have certain features in common, such as coating, incubating and binding, washing to remove non-specifically bound species, and detecting the bound immune complexes. These are described below.

In coating a plate with either peptoid or antibody, one will generally incubate the wells of the plate with a solution of the peptoid or antibody, either overnight or for a specified period of hours. In certain aspects, the plate can be blocked using a bacterial lysate, such as an *E. coli* lysate (See Example 1). The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface. Alternatively, because of the simple and predictable chemistry of the peptoids, they can be attached to the support by means of a specific chemical reaction.

In ELISAs, it is probably more customary to use a secondary or tertiary detection means rather than a direct procedure. Thus, after binding of a peptoid or antibody to the well, coating with a non-reactive material to reduce background, and washing to remove unbound material, the immobilizing surface is contacted with the biological sample or peptoid to be tested under conditions effective to allow immune complex formation. Detection of the immune complex then requires a labeled secondary binding peptoid or antibody, or a secondary binding peptoid or antibody in conjunction with a labeled tertiary antibody (with specificity either for the Fc region of the antibody or the peptoid).

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

Detection may utilize an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody or peptoid for a period of time and under conditions that favor the development of further immune complex formation (e.g., incubation for 2 hours at room temperature in a PBS-containing solution such as PBS-Tween).

After incubation with the labeled antibody or peptoid, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Förster Resonance Energy Transfer (FRET)

FRET is a phenomenon in which the excited-state energy in one molecule (called the donor) is transferred to another molecule by a radiationless coupling. This mechanism was first correctly described by Förster, and differs from other types of energy transfer, such as electron sharing (Dexter) or trivial transfer (emission of a photon from the donor and reabsorption by the acceptor). The Dexter mechanism requires the two molecules to be in physical contact, while trivial transfer is a very low probability. In contrast, the Förster mechanism exhibits a high probability when the two molecules are within the Förster radius, which is defined for any given pair of fluorophores.

The overall FRET efficiency depends on the Förster radius, and is determined by several factors and is directly related to the amount of overlap between the absorption spectra of the acceptor molecule and the emission spectra of the donor molecule. The amount of FRET also depends on the alignment of the donor and acceptor molecules, although most biological systems are not rigidly aligned. The FRET efficiency is also affected by the ability of the acceptor molecule to absorb light, as indicated by its molar extinction coefficient, and the overall stability of the excited state of the donor molecule, as indicated by the probability that absorption will lead to fluorescence (quantum yield) and the lifetime of the excited state.

FRET between two different fluorophores can be assayed by several methods: looking at the change in color of the fluorescence, measuring the fluorescence lifetime of the donor, examining the changes upon photobleaching either the donor or acceptor, or as we show in this new invention: by measuring the fluorescence polarization of the acceptor. Regardless of the approach, most of these assays share common features of the instrumentation.

The types of the microscope used to measure FRET can be suitably selected depending on the purpose. If frequent observations are necessary for monitoring a time course of the changing, conventional incident-light fluorescent microscope is preferred. If resolution is to be increased as in the case where detailed intercellular localization is to be monitored, confocal laser microscope is preferred. As a microscope system, an inverted microscope is preferred for most live cell measurements in view of keeping the physiological state of cell and preventing contamination. When an upright microscope is used, a water immersion lens can be used in the case of using lens of high power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 490-510 nm and fluorescent light of about 520-550 nm. For the observation of CFP, it is preferred to use a filter with excitation light of about 425 nm and fluorescent light of about 460-500 nm. For the purposes of the present invention, there are no specific requirements in terms of microscopes and filters, except that it would be useful to minimize the use of depolarizing elements in the light path. Microscope manufacturers all market strain-free optics for polarized light measurements in transmission and reflection microscopy, and such optics would be helpful for these polarized fluorescence measurements as well.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly acquired by exposure of short period. Confocal microscopes can also be used for live cell imaging, as long as care is taken to minimize the exposure times.

C. Luminex Beads

Luminex's xMAP® technology relies on existing technology platforms, including flow cytometry, microspheres, lasers, digital signal processing and traditional chemistry. Featuring a flexible, open-architecture design, xMAP® technology can be configured to perform a wide variety of bioassays quickly, cost-effectively and accurately.

Luminex color-codes microspheres into 100 distinct sets. Each bead set can be coated with a peptoid according to the present invention, thereby allowing the capture and detection of specific antibodies from samples. Within the Luminex compact analyzer, lasers excite the internal dyes that identify each microsphere particle, and also any reporter dye captured during the assay. Many readings are made on each bead set, further validating the results. In this way, xMAP technology allows multiplexing of up to 100 unique assays within a single sample, both rapidly and precisely.

xMAP technology has been adopted across many segments of the life sciences, including protein expression profiling, molecular and immunodiagnostics, HLA testing, and biodefense/environmental.

D. Tentagel Beads

In certain aspects, tentagel beads or resin can be used in compositions and methods for detecting antibodies related to a particular ND. One of the most common microsphere formations is tentagel, a styrene-polyethylene glycol co-polymer. These microspheres are unswollen in nonpolar solvents such as hexane and swell approximately 20-40% in volume upon exposure to a more polar or aqueous media.

Peptoids may be attached to or synthesized on a solid support such as tentagel beads. Tentagel beadshave a polystyrene core and attached to the core is a plurality of polyoxyethylene arms, each arm having a primary amine at its free end. Peptoids can be synthesized by sequential conjugation of each residue added to the peptoid, using peptoid synthesis chemistry. The split synthesis method yields beads each of which comprises multiple copies of a single peptoid sequence.

Because the polyoxyethylene arms of the tentagel beads are water soluble, the conformations of the peptoids are determined primarily by thermodynamics and by their primary sequence.

E. Immunodetection Kits

In still further embodiments, the present invention concerns detection kits for use with the methods described above. Peptoids according to the present invention will be included in the kit. The immunodetection kits will thus comprise, in a suitable container, one or more peptoids that bind antibodies for Alzheimer's Disease, Parkinson's Disease, or both, optionally linked to a detection reagent and/or a support.

In certain embodiments where the peptoid is pre-bound to a solid support, the support is provided and includes a column matrix, bead, stick or well of a microtitre plate. The immunodetection reagents of the kit may take any one of a variety of forms, including those detectable labels that are associated with or linked to the given peptoid or secondary antibody. Exemplary secondary antibodies are those having binding affinity for the sample antibodies.

The container will generally include at least one vial, test tube, flask, bottle, syringe or other container, into which the peptoid may be placed, or preferably, suitably aliquoted. The kits of the present invention will also typically include a means for containing the peptoid, antibody, and any other reagent containers in close confinement for commercial sale. Such containers may include injection or blow-molded plastic containers into which the desired vials are retained.

Certain embodiments are directed to kits comprising and methods for employing peptoids described herein. A kit and/or method for detecting, evidencing, and/or categorizing at least one disease state is disclosed. The steps taken include obtaining a sample from a subject, e.g., a human, and conducting a peptoid binding analysis on the sample using reagents or array substrate supplied in a kit format. As a result, at least one antibody indicative of a disease state is isolated from or identified in a sample. Antibodies binding the peptoids described here are related to at least a risk of disease development or to the existence of a particular disease state.

In addition, various kits are contemplated for use by the present invention. One such kit provides for determining the presence of the disease specific antibody, including one or more antibodies related to Alzheimer's disease and/or Parkinson's disease. At least one peptoid is incorporated into the kit that is capable of specifically binding with a disease specific antibody. In certain aspects reagents for determining binding between the peptoid and an antibody can also be included. The peptoids described herein may be immobilized on a solid support or substrate, and include at least one detection reagent to determine if an antibody is bound to the peptoid. The sample utilized for any of the kits may be a fractionated or unfractionated body fluid or a tissue sample. Non-limiting examples of such fluids are blood, blood products, urine, saliva, cerebrospinal fluid, and lymph.

Further contemplated is a kit for diagnosing, determining risk-assessment, and identifying therapeutic avenues related to a neurodegenarative disease state. This kit includes at least one peptoid capable of specifically binding an antibody indicative of a disease state. Reagents for determining binding between the peptoid and the antibody can also be included.

The disease specific antibodies that are analyzed according to the method of the invention are released into the circulation and may be present in the blood or in any blood product, for example plasma, or serum, and dilutions and preparations thereof, as well as other body fluids, e.g. cerebrospinal fluid (CSF), saliva, urine, lymph, and the like. Any suitable direct or indirect assay method may be used to determine the level of antibodies measured. The assays may be competitive assays, sandwich assays, and the labels may be selected from the group of well-known labels such as radioimmunoassay, fluorescent, or chemiluminescence immunoassay or immunoPCR technology.

IV. Antibody Compositions

Certain embodiments include methods and compositions for characterizing antibodies and the antigenic determinants recognized by the antibodies characteristic of a particular ND. For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or non-contiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen.

T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

The antibody can be bound to a solid support substrate or conjugated with a detectable moiety or be both bound and conjugated as is well known in the art. For a general discussion of conjugation of fluorescent or enzymatic moieties see Johnstone et al. (1982). The binding of antibodies to a solid support substrate is also well known in the art (Harlow et al., 1988; Borrebaeck, 1992).

Once an antigen or antibody indicative of a ND is identified, recombinant techniques can be used to produce both the antigen and/or variants of the identified antibody, including monoclonal antibodies. For instance, single chain antibodies (SCAs) are genetically engineered proteins designed to expand on the therapeutic and diagnostic applications possible with monoclonal antibodies. SCAs have the binding specificity and affinity of monoclonal antibodies and, in their native form, are about one-fifth to one-sixth of the size of a monoclonal antibody, typically giving them very short half-lives. SCAs offer some benefits compared to most monoclonal antibodies, including their ability to be directly fused with a polypeptide that may be used for detection (e.g., luciferase or fluorescent proteins). In addition to these benefits, fully-human SCAs can be isolated directly from human SCA libraries without the need for costly and time consuming "humanization" procedures.

Single-chain recombinant antibodies (scFvs) consist of the antibody VL and VH domains linked by a designed flexible peptide tether (Atwell et al., 1999). Compared to intact IgGs, scFvs have the advantages of smaller size and structural simplicity with comparable antigen-binding affinities, and they can be more stable than the analogous 2-chain Fab fragments (Colcher et al., 1998; Adams and Schier, 1999). The variable regions from the heavy and light chains (VH and VL) are both approximately 110 amino acids long. They can be linked by a 15 amino acid linker or longer with a sequence, for example, which has sufficient flexibility to allow the two domains to assemble a functional antigen binding pocket. In specific embodiments, addition of various signal sequences allows the scFv to be targeted to different organelles within the cell, or to be secreted. Addition of the light chain constant region (Ck) allows dimerization via disulfide bonds, giving increased stability and avidity. Thus, for a single chain Fv (scFv) SCA, although the two domains of the Fv fragment are coded for by separate genes, it has been proven possible to make a synthetic linker that enables them to be made as a single protein chain scFv (Bird et al., 1988; Huston et al., 1988) by recombinant methods. Furthermore, they are frequently used due to their ease of isolation from phage display libraries and their ability to recognize conserved antigens (for review, see Adams and Schier, 1999). Thus, in some aspects of the invention, an antibody may be an SCA that is isolated from a phage display library rather than that generated by the more traditional antibody production techniques described above.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure.

Methods of producing or isolating polyclonal antibodies are known to those of skill in the art. Typically, polyclonal antibodies are prepared by taking a source containing antibodies of interest and fractionating the source to enrich for antibodies with a reactivity of interest, e.g., peptoid binding. See, e.g., Harlow and Lane (1988) Antibodies: A Laboratory Manual, CSH press, NY.

Briefly, an example of isolating antibodies that bind particular peptoids can include, but is not limited to obtaining a sample comprising such antibodies; ammonium sulfate precipitating the antibodies from the sample; and isolating the antibodies by immunoaffinity purification using standard techniques and one or more peptoids as an affinity reagent. The affinity resin used can be an activated CH-Sepharose coupled to peptoid(s) having a structure described herein. The antibody precipitate can be loaded onto the column and washed with PBS or another appropriate buffer or washing solution. The precipitate can then be eluted and collected. The concentration of the antibody obtained can be determined using a total protein colorimetric determination (Bio-Rad).

It is not intended that the present invention be limited to the use of this particular protocol for the production and purification of antibodies, as numerous protocols are available and known to those in the art (See, e.g., Sambrook et al. (eds.), Molecular Cloning, Cold Spring Harbor Laboratory Press [1989]; Harlow and Lane (eds.), Antibodies: A Laboratory Manual, Cold Spring Harbor Laboratory Press [1988]; and Ausubel et al. (eds.), Current Protocols in Molecular Biology, Ch. 11, John Wiley & Sons, Inc., New York [1994]). The only criterion for antibody production methods finding use with the invention is that sufficiently purified antibody preparations be produced.

V. Chemical Group Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "azido" means —N$_3$; "mercapto" means —SH; "thio" means =S; "thioether" means —S—; "sulfonamido" means —NHS(O)$_2$; "sulfonyl" means —S(O)$_2$—; "sulfinyl" means —S(O)—; and "silyl" means —SiH$_3$.

For the structures provided herein, the following parenthetical subscripts further define the groups as follows: "(Cn)" defines the exact number (n) of carbon atoms in the group. For example, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH₂CH₂OH, —CH₂CF₃, —CH₂CH₂OC(O)CH₃, —CH₂CH₂NHCO₂C(CH₃)₃, and —CH₂Si(CH₃)₃.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH₂ (vinyl), —CH═CHCH₃, —CH═CHCH₂CH₃, —CH₂CH═CH₂ (allyl), —CH₂CH═CHCH₃, and —CH═CH—C₆H₅. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH₃, —C≡CC₆H₅ and —CH₂C≡CCH₃, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH₃)₃, is a non-limiting example of a substituted alkynyl group.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C₆H₄CH₂CH₃ (ethylphenyl), —C₆H₄CH₂CH₂CH₃ (propylphenyl), —C₆H₄CH(CH₃)₂, —C₆H₄CH(CH₂)₂, —C₆H₃(CH₃)CH₂CH₃ (methylethylphenyl), —C₆H₄CH═CH₂ (vinylphenyl), —C₆H₄CH═CHCH₃, —C₆H₄C≡CH, —C₆H₄C≡CCH₃, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C₆H₄F, —C₆H₄Cl, —C₆H₄Br, —C₆H₄I, —C₆H₄OH, —C₆H₄OCH₃, —C₆H₄OCH₂CH₃, —C₆H₄OC(O)CH₃, —C₆H₄NH₂, —C₆H₄NHCH₃, —C₆H₄N(CH₃)₂, —C₆H₄CH₂OH, —C₆H₄CH₂OC(O)CH₃, —C₆H₄CH₂NH₂, —C₆H₄CF₃, —C₆H₄CN, —C₆H₄CHO, —C₆H₄CHO, —C₆H₄C(O)CH₃, —C₆H₄C(O)C₆H₅, —C₆H₄CO₂H, —C₆H₄CO₂CH₃, —C₆H₄CONH₂, —C₆H₄CONHCH₃, and —C₆H₄CON(CH₃)₂.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)C₆H₄CH₂CH₃, —COC₆H₃(CH₃)₂, and —C(O)CH₂C₆H₅, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH₂CF₃, —CO₂H (carboxyl), —CO₂CH₃ (methylcarboxyl), —CO₂CH₂CH₃, —CO₂CH₂CH₂CH₃, —CO₂C₆H₅, —CO₂CH(CH₃)₂, —CO₂CH(CH₂)₂, —C(O)NH₂ (carbamoyl), —C(O)NHCH₃, —C(O)NHCH₂CH₃, —CONHCH(CH₃)₂, —CONHCH(CH₂)₂, —CON(CH₃)₂, —CONHCH₂CF₃, —CO-pyridyl, —CO-imidazoyl, and —C(O)N₃, are non-limiting examples of substituted acyl groups. The term "substituted acyl" encompasses, but is not limited to, "heteroaryl carbonyl" groups.

The term "alkoxy" when used without the "substituted" modifier refers to the group —OR, in which R is an alkyl, as that term is defined above. Non-limiting examples of alkoxy groups include: —OCH₃, —OCH₂CH₃, —OCH₂CH₂CH₃, —OCH(CH₃)₂, —OCH(CH₂)₂, —O-cyclopentyl, and —O-cyclohexyl. The term "substituted alkoxy" refers to the group —OR, in which R is a substituted alkyl, as that term is defined above. For example, —OCH₂CF₃ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "saturated" when referring to an atom means that the atom is connected to other atoms only by means of single bonds.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Validation of Peptoids as Selective Markers for Alzheimer's Disease and Parkinson's Disease The inventors employed microarrays comprised of two copies of an array of 4680 octameric peptoids along with various markers and control spots. Serum (blood) collected from 6 Alzheimer's patients and 6 Normal controls were hybridized with the microarrays. The serum samples were diluted greatly to provide a final total serum protein concentration of 20 μg/ml and this solution was hybridized to the peptoid microarray. After incubation and washing, the IgG binding pattern was visualized by subsequent incubation with an Alexa-647-labeled secondary antibody. As a control, the secondary antibody alone was exposed to the array and any features that bound significant amounts of the labeled secondary antibody were ignored in subsequent analysis.

Figures 2A, 2B, 2C:
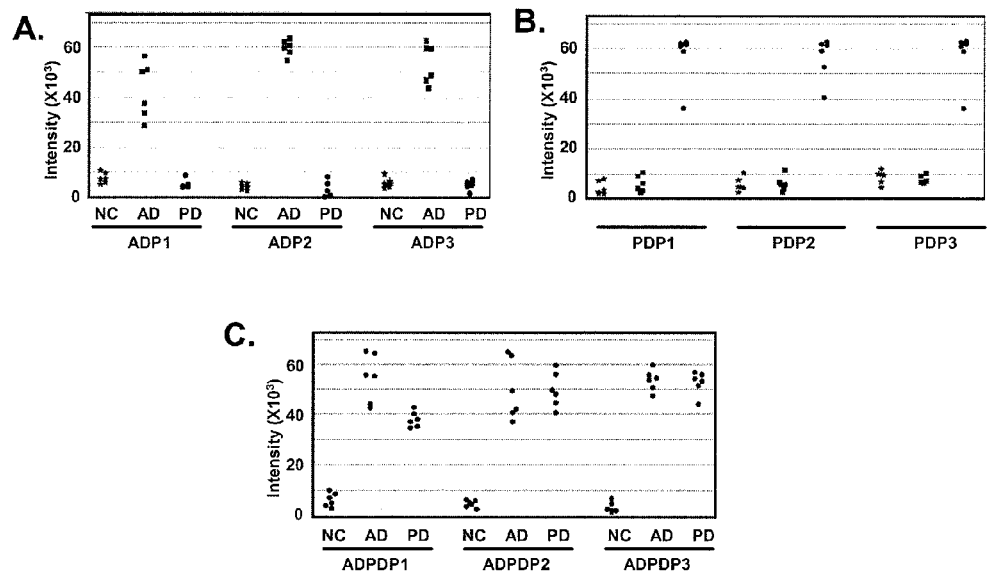
FIGS. 2A-C—Antibody Profiles That Distinguish Alzheimer's Disease and Parkison's Disease Subjects from Controls.

GenePix analysis of all of the features on the array revealed several peptoids (FIG. 1A) that reproducibly were much brighter when exposed to the AD serum than the Normal serum (an intensity of >30,000 vs. <10,000 at this particular protein concentration) (FIG. 2A). Three of the peptoids of interest behaved in this fashion. To test the specificity of the peptoids, serum collected from Parkinson's patients was hybridized with these peptoids. However, only background levels of IgG antibody were captured by peptoids from these serum samples, arguing that these peptoids are specific capture agents for antibodies produced in Alzheimer's disease (FIG. 2A).

Having completed this training set, the inventors then tested the ability of these three peptoids to distinguish AD by analyzing serum samples collected from patients that were not included in the training set (FIG. 4-13). Peptoids were also validated in a microarray assay and a Luminex bead assay (FIG. 7). All the three peptoids identified in the training performed perfectly in blinded experiments. These three peptoids were sequenced by mass spectrometry, resynthesized and purified by HPLC.

In summary, the inventors have demonstrated that synthetic molecules capable of capturing particular IgGs from Alzheimer's disease with specificity can be isolated by peptoid combinatorial library screening.

TABLE 3

Summary of Microarray Analysis

| Score | Prediction | Clinical Diagnosis |
|---|---|---|
| Positive | 16 | All correct |
| Negative | 16 | All correct |
| Intermediate | 4 | AD(2) NC(2) |

Total samples tested = 36

TABLE 4

Evaluation of assay using Luminex platform

| Score | Prediction | Clinical Diagnosis |
|---|---|---|
| Positive | 47 | All correct |
| Negative | 54 | All correct |
| Intermediate | 9 | AD(3) NC(2) PD(4) |

Total samples tested = 110

Figure 3:
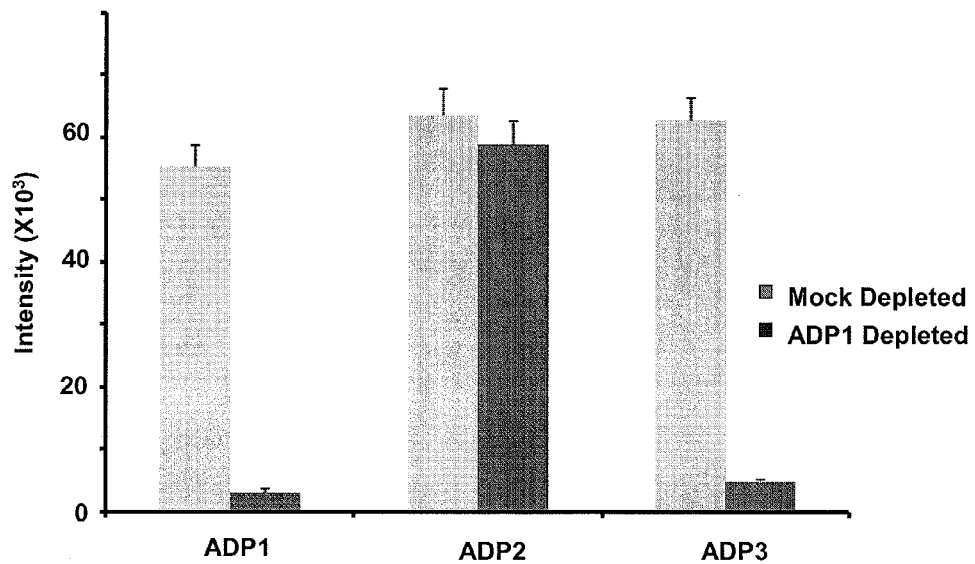
FIG. 3 Depletion of AD (Autopsy-confirmed) serum sample. The serum samples were depleted of antibodies that bind to the ADP1 by passage over a column displaying an excess of immobilize ADP1. The depleted serum was then assessed for binding to ADP1-3. The graph indicates that peptoids ADP1 and ADP3 bind to the same antibodies, whereas peptoid ADP2 binds different antibodies.
Figure 4:
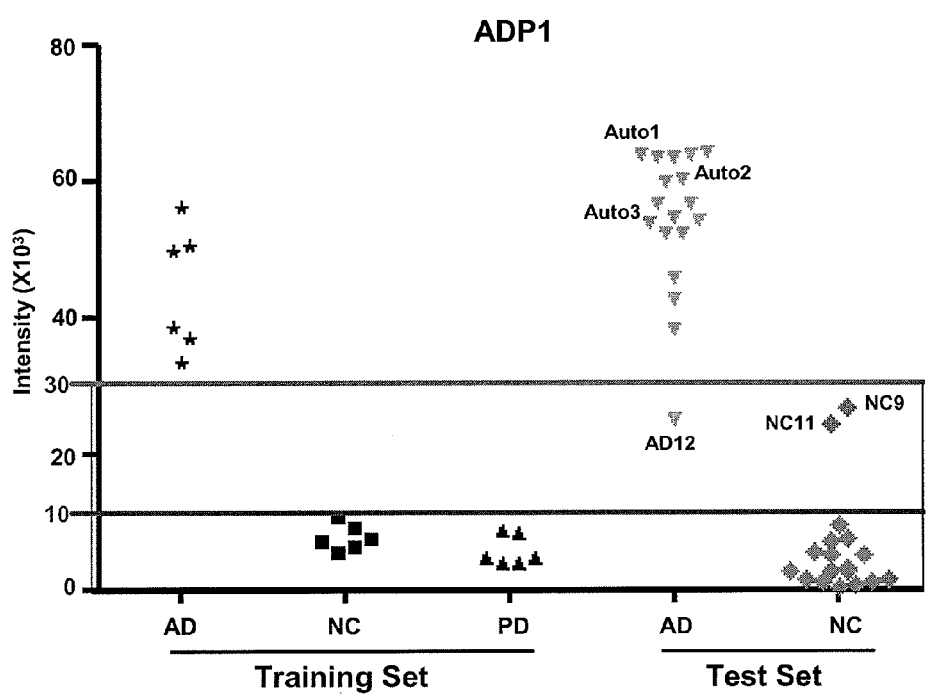
FIG. 4 Validation of ADP1 peptoid as a selective marker for Alzheimer's disease on Microarrays.
Figure 5:
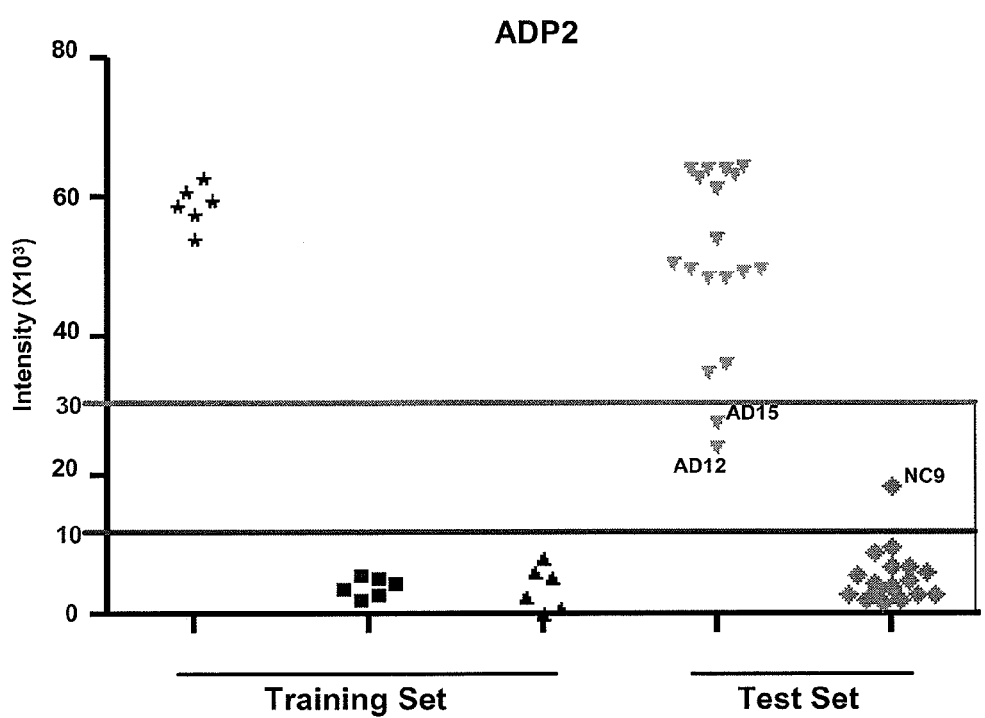
FIG. 5 Validation of ADP2 peptoid as a selective marker for Alzheimer's disease on Microarrays.
Figure 6:
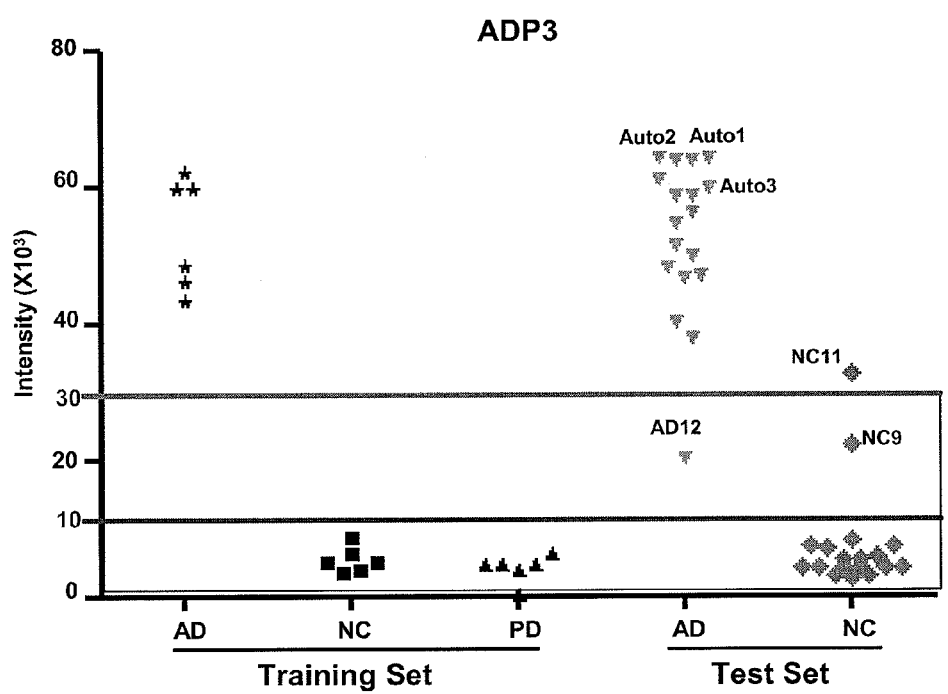
FIG. 6 Validation of ADP3 peptoid as a selective marker for Alzheimer's disease on Microarrays.
Figure 9:
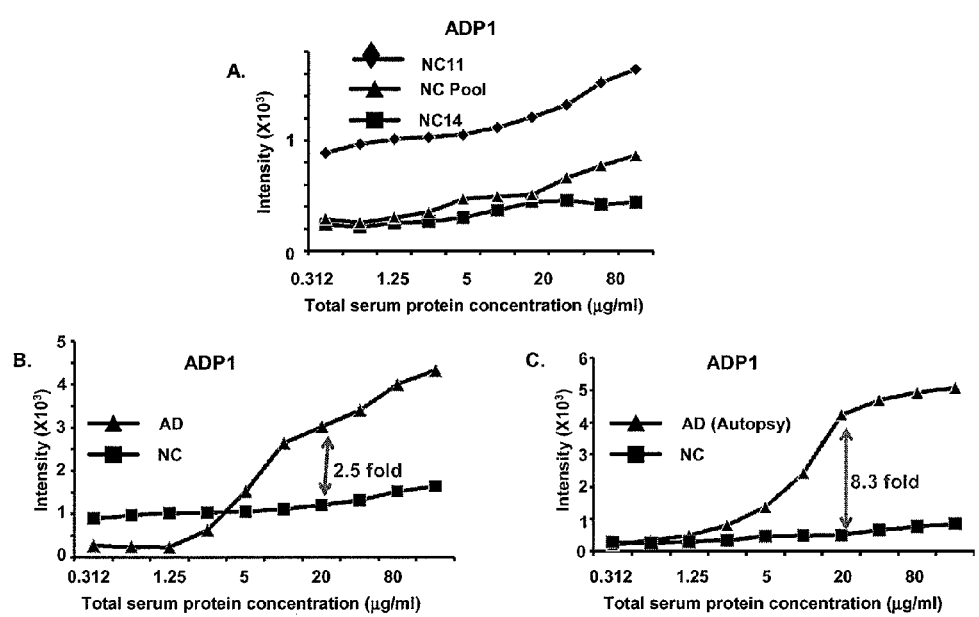
FIG. 9 The Luminex® titration of different Normal Control samples.
Figure 10:
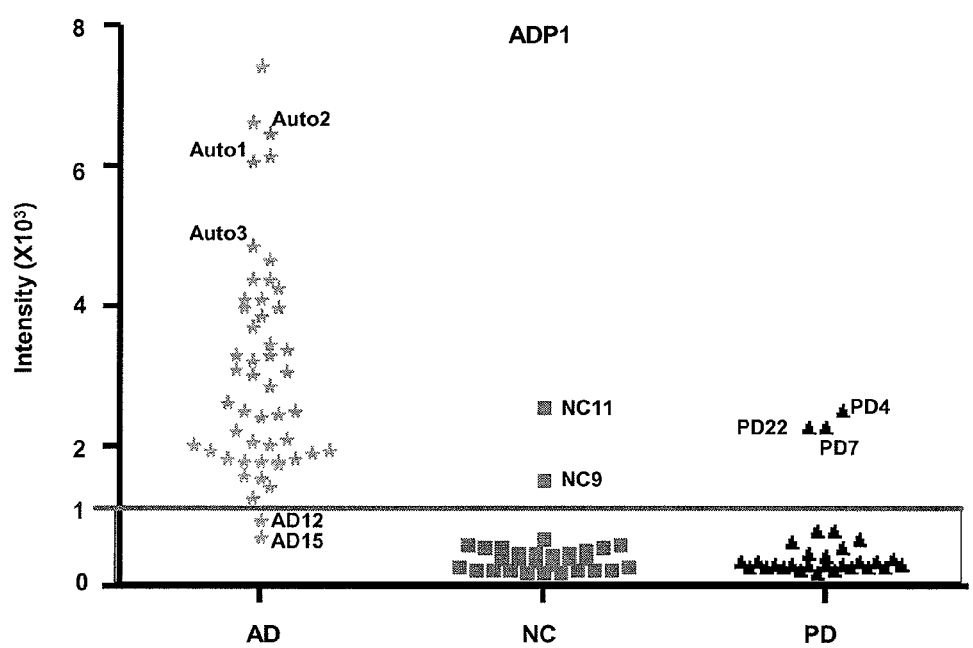
FIG. 10 Validation of ADP1 peptoid as a selective marker for Alzheimer's disease on Luminex® beads.
Figure 11:
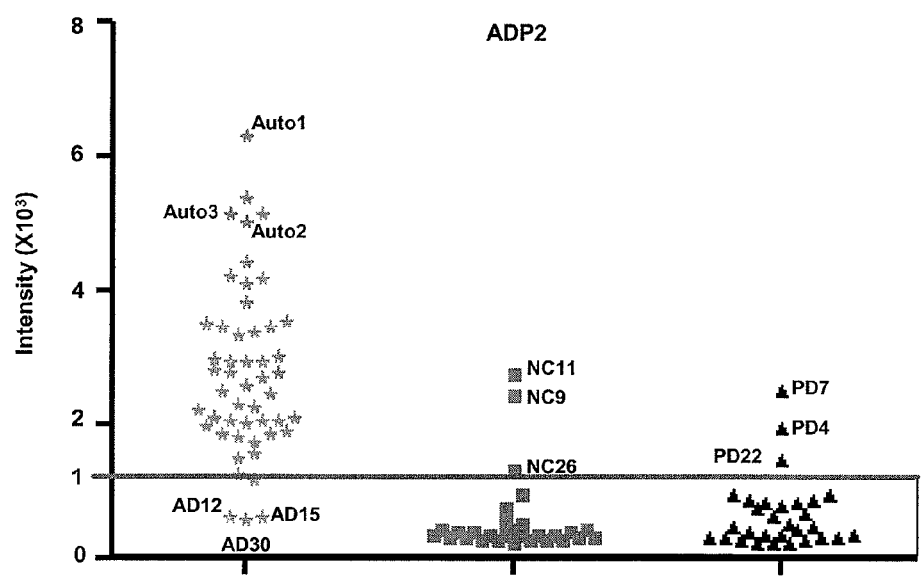
FIG. 11 Validation of ADP2 peptoid as a selective marker for Alzheimer's disease on Luminex® beads.
Figure 12:
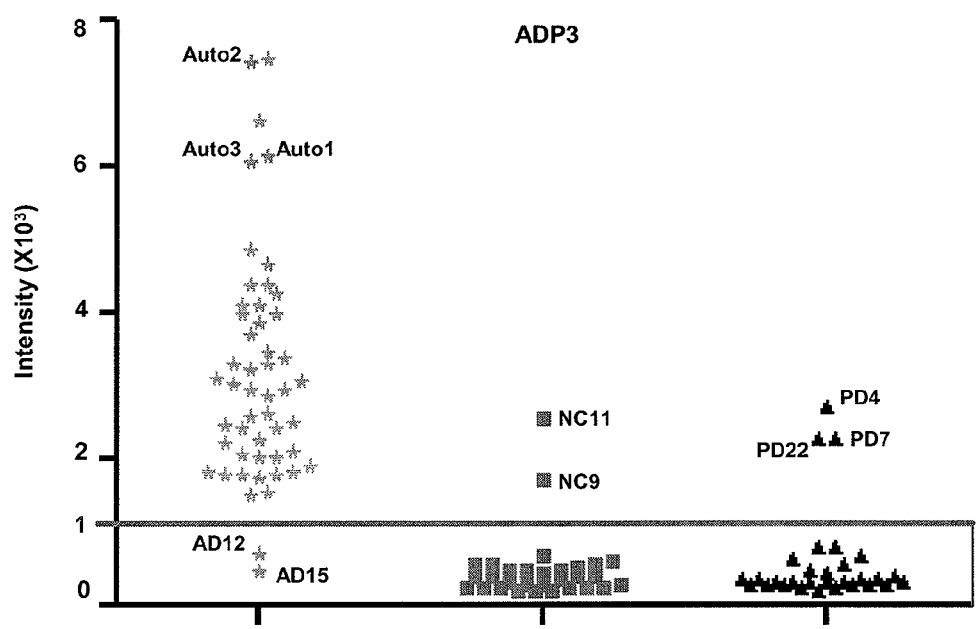
FIG. 12 Validation of ADP3 peptoid as a selective marker for Alzheimer's disease on Luminex® beads.
Figure 13:
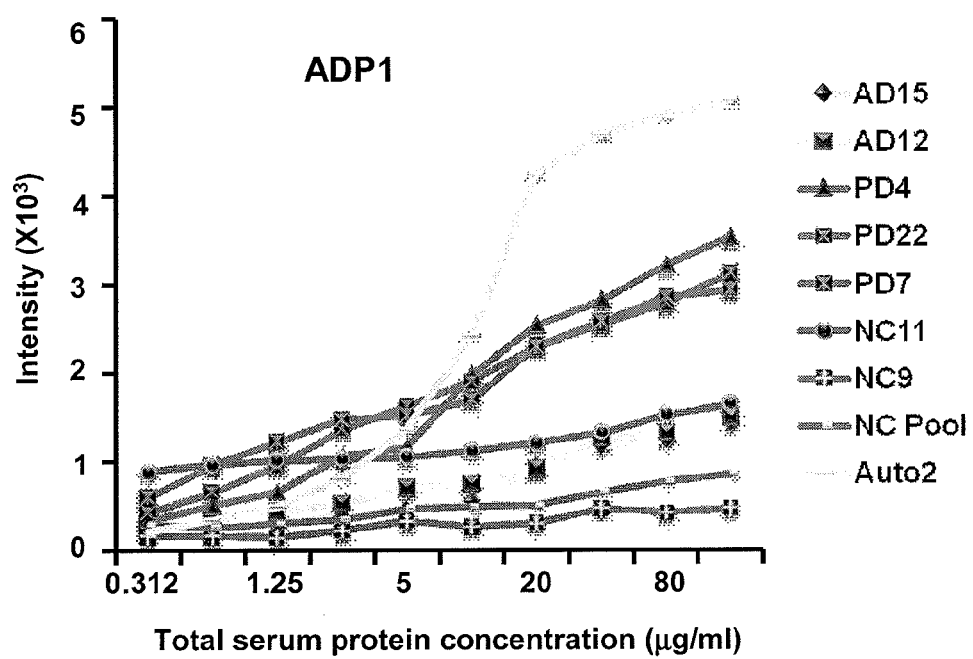
FIG. 13 The Luminex® titration of Intermediate samples.

Additional studies were performed by examining the binding characteristics of serum that had been depleted using the APD1 peptoid prior to analysis on peptoid array comprising ADP1-3 (FIG. 3). The antibody depletion experiments indicate that APD1 and ADP3 bind a similar antibody population. Whereas ADP2 seems to bind a second population of antibodies.

Library Synthesis and printing protocol: An 8 mer peptoid library with one constant residue (Cysteine on the C-terminal) was synthesized using the conventional split-and-pool method on 500 μm polystyrene macrobeads. The beads are then placed in a 96 well plate with one bead in each well. The peptoids are then cleaved from the beads using a cleavage cocktail of 95% Trifluoroacetic acid, 2.5% water and 2.5% triisopropylsilane. Fifty (50 μl) of this cocktail was put into each well and the beads were left in this cocktail for two hours. The cocktail solution was allowed to evaporate. After the cocktail have evaporated, 40 μl of a 50% Acetonitrile and 50% water was added to each well.

The liquid contents of four 96 well plates (40 μl per well) are then transferred to a 384 well plate using a Tecan Genesis Workstation 200. Thirty-four (34 μl) of each plate is transferred to a new 384 well plate. The plates containing 6 μl in each well are marked as 'Residual' plates and set aside so that the Acetonitrile/water mixture would evaporate. These plates are then sealed with adhesive sheet and stored in a −80 degree freezer until needed for sequencing purposes. The Plates with 34 µl liquid are marked as 'Master' and also set aside for the Acetonitrile/water mixture to evaporate.

When the liquid had evaporated from the Master plates, 20 µl of DMSO (Dimethylsulfoxide) is added to each well using the Tecan Genisis Workstation. Five (5 µl) is then removed from each well and placed into another 384 well plate. This plate has 5 µl of DMSO added to each well and becomes the 'Copy' plate. The Master plates are then sealed with an adhesive sheet and stored in a −80 degree freezer. The Copy plates are stored in a 4 degree refrigerator and used for printing microarrays as needed.

Contents of the Copy plates are then printed onto maleimide coated glass slides using a NanoPrint with MP946 Micro Spotting Pins. A 10% Ethanol and water mixture was used to wash the pins before printing and between each spot cycle. Multiple wash/sonicate/dry cycles were used between each sample pick-up and print cycle. Complex arrays were printed with a full head of 48 pins and using a spot spacing of 410 um in a 10 by 10 grid. Sub-arrays were printed with a single MP946 pin in a Whatman Fast Frame format, 16 arrays on a slide in a 2 by 8 format and a 480 µm spot spacing in a 10 by 10 grid. Slides are allowed to set in 50% humidity for 12 hours before printing. After printing, the humidifier is turned off and the slides are allowed to set for 12 hours before being scanned using a GenePix Autoloader 4200AL Scanner. Slides are scanned with a PMT of 500 to verify spot placement and morphology.

Protocol for making Glass Slides: The slides are marked on one corner using a diamond pencil. Then the slides are placed in glass slide racks and the racks placed into glass staining jars.

Glass beakers (2 L) are placed into ice buckets and ice packed around them. A solution of 70/30 Concentrated $H_2SO_4$ and $H_2O_2$ (Piranha) is made in this beaker and let cool to room temperature. The Piranha solution is decanted into the glass staining jars so that the liquid covered the slides. This is covered and left set for 12 hours at room temperature. They are then removed and rinsed thoroughly with de-ionized water. The slides are placed in the centrifuge to dry.

A water-bath is heated to 80° C. The glass slides are immersed in 3-glycidoxypropyltrimethoxysilane and placed in water-bath for 5-6 hours while gently shaking. The slides are allowed to cool and then rinsed two times with DMF. The slides are again placed in the centrifuge to dry and stored in Argon until needed for the next step.

The water-bath temperature is maintained at 80°. The slides are immersed in a mixture of 2 L Poly(ethylene glycol) with 8 mL $H_2SO_4$ and placed in the water-bath. The water-bath is agitated at medium to low speed for 6 hours. The slides are allowed to cool and rinsed with DI water while agitating for about one hour. The slides are again placed in the centrifuge to dry and stored in Argon until needed for the next step.

PMPI is measured and dissolved in Anhydrous DMSO to make a 50 mM solution. The slides are then placed with the scratch side up and to the top of the PMPI reaction vessel. PMPI is injected below the slides so that it completely filled the vessel and some excess in the reservoirs. All air bubbles are removed from the underside of the slides. The reaction vessel is agitated overnight under argon on a shaker. The slides are removed from the reaction vessel and washed in DMSO for an hour. This step is repeated once. The next wash is with DMF for one hour. The slides are again placed in the centrifuge to dry and stored in Argon until needed.

Hybridization Protocol: Microarray slides are covered with hybridization chamber and equilibrated with 1×TBST (50 mM Tris, pH 8.0, 150 mM NaCl, 0.1% Tween20) for 15 minutes. The slides are then blocked with 1 ml of blocking buffer for 1 hour at 4° C. The blocking buffer is removed and the slides are incubated with 1 ml of serum (20 µg/ml) for 16 hours at 4° C. with gentle shaking. In an alternative method, the slides are blocked with 1 ml of *E. coli* lysate (1.5 mg/ml) for 1 hour at 4° C. The *E. coli* lysate is removed and the slides are incubated with 1 ml of serum (15 µg/ml) in *E. coli* lysate (1.5 mg/ml) for 18 hours at 4° C. with gentle shaking. Microarrays are then washed three times with 1×TBST and hybridized with Alexa-647 labeled Anti IgG antibody (5 µg/ml) for 2 hours on orbital shaker at 4° C. The chamber cassettes were removed from microarray slides and washed with 1×TBST (3×15 min) followed by 0.1×TBST (1×10). The slides are then dried on centrifuge (5 min at 1500 RPM) and scanned on microarray scanner (Gene Pix Autoloader 4200) by using 635-nm laser at 100% power and 600 or 650 photomultiplier tube gain. All the scanned images were analyzed by the Gene Pix Pro 6.0 software and Genespring software.

Example 2

Sarcosine Scan of ADP1-3

Figure 14:
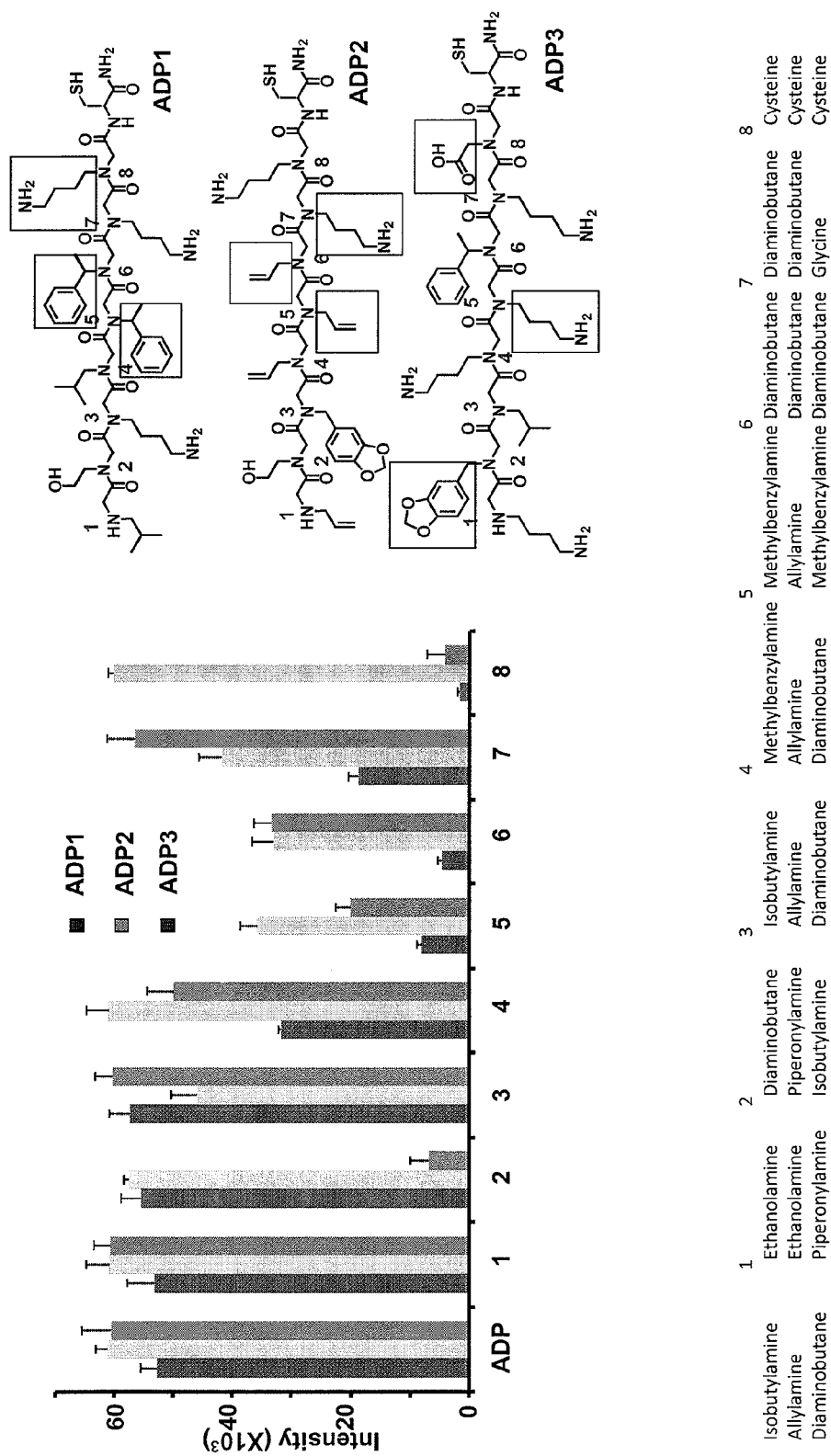
FIG. 14 The Sarcosine Scan results of ADP1-3.
Figure 15:
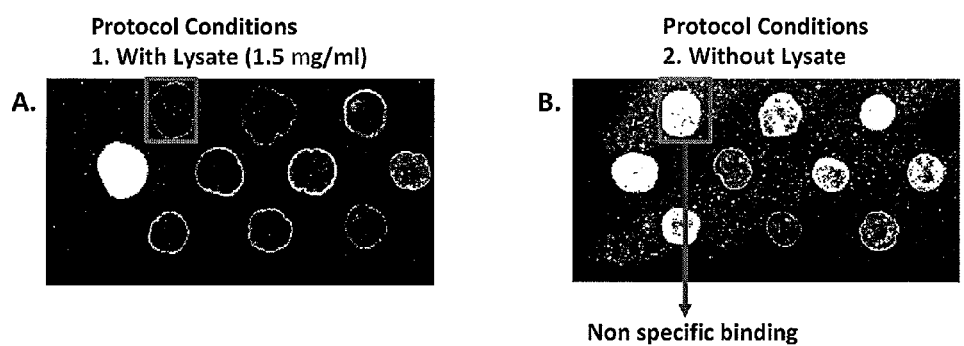
FIG. 15 A comparison of a peptoid array incubated with or without a bacterial lysate blocking agent.

A sarcosine scan has the effect of replacing each of the side chains in turn with a methyl group rather than a hydrogen, preserving the tertiary amide bond, but removing the bulk of the side chain. Peptoids ADP1-3 each contain eight positions that were varied in the original library synthesis (FIG. 14). To determine which of the side chains at these eight positions might be important for binding the AD-specific antibodies, twenty four derivatives were synthesized in which each of the side chains, in turn, was substituted by a methyl group. Each compound was made by solid phase "sub-monomer" chemistry where methylamine was employed to displace the bromide at the position where substitution was desired. To test the antibody-binding characteristics of each methyl side chain-containing derivative, all 24 compounds, as well as the ADP1-3 peptoids were printed onto a microarray. Serum for autopsy-confirmed AD patients was hybridized to the se arrays. After washing, fluorescently-labeled secondary antibody was applied to the array. Following further washing, the intensity of fluorescence at each position was determined using a fluorescence scanner. The intensities are shown in the FIG. 14. When significant dimunition in fluorescence was observed at a given spot relative to the parent compound (indicating capture of less antibody), this was interpreted as indicating that the side chain present at this position in the parent compound was important for binding to the AD-specific antibodies.

Example 3

Materials and Methods

Examples of the material methods used in these studies include the following.

Synthesis and purification of peptoids. Peptoids can synthesized bt using an ABI 433A peptide synthesizer or a parallel synthesis robot on Rink amide resin according to the submonomer method. (See, e.g., Zuckermann, R. N., Kerr, J. M., Kent, S. B. H., & Moos, W. H. (1992) J. Am. Chem. Soc., 114, 10646-10647.) Briefly, the amide on the nascent chain is bromoacetylated, followed by $S_{N2}$ displacement of bromide by a primary amine to form the side chain. Following synthesis, peptoids can be cleaved and deprotected in trifluoroacetic acid (TFA):triisopropylsilane:water (95:2.5: 2.5 by vol.). Compounds can be purified by RP-HPLC on a C18 column with a linear acetonitrile/water gradient. Mass spectrometry can be used to confirm the molecular weight of the purified product.

A monomer of the growing peptoid polymer can be assembled in two steps, using two readily available submonomeric units. Rink amide resin is bromoacetylated, using diisopropylcarbodiimide-activated bromoacetic acid. Next, the bromoacetylated resin undergoes $S_{N2}$ displacement of bromide by a primary amine, which introduces the desired side chain. Hundreds of potential amine submonomers and corresponding side chains are commercially or synthetically available. Synthesis of peptoids by the submonomer protocol provides facile access to sequences of greater chemical diversity than readily obtained via the monomer approach and are limited only by sequence order, length and/or N-pendant side chain structure sufficient to provide desired activity.

More specifically, Rink Amide resin (4-(2',4'-Dimethoxyphenyl-(9-fluorenylmethyloxycarbonyl)-aminomethyl)-phe-noxy resin, 0.25 mmol; Novabiochem) can be initially swelled for 30 min in $CH_2Cl_2$. Following the resin swelling, the 9-fluorenylmethyloxycarbonyl (Fmoc) protecting group is removed by treatment with 20% piperidine solution in 1-methyl-2-pyrrolidone (NMP). The resin-bound deprotected amine is then bromoacetylated by reaction with 4.2 ml of 1.2 M bromoacetic acid (50 mmol) in N,N-dimethylformamide (DMF) and 1.0 ml (11 mmol) neat N,N'-diisopropylcarbodiimide (DIC) for 60 minutes at room temperature with constant mixing. Next, the resin is rinsed with DMF (3×10 ml), followed by NMP rinses (3×10 ml). 6 ml of a 1 M solution (6 mmol) of a primary amine "submonomer" in either NMP or $CH_2Cl_2$ reacted with the resin-bound bromoacetyl moiety, displacing bromide. A protected submonomer is synthesized in order to create the N-(4-aminobutyl) glycine residue (Nlys). The resin is then rinsed again with NMP (3×10 ml) followed by DMF (3.times.10 ml). The product of these two reactions generates a peptoid "residue", the identity of which depended upon the submonomer amine employed. Peptoids are elongated by this submonomer method until the desired chain-length is attained.

Following synthesis, peptoid oligomers can be cleaved from the resin, simultaneously removing the tert-butoxycarbonyl (Boc) protecting group from Nlys residues, by treatment with 2,2,2-trifluoroacetic acid (TFA)/triisopropylsilane/$H_2O$ (95:2.5:2.5 by volume). Subsequent to cleavage, peptoids can be purified to >97% homogeneity by preparative scale reversed-phase HPLC. The precise gradient employed for HPLC depends on the identity and hydrophobicity of the peptoid.

Such synthesis and characterization are also described in U.S. Pat. No. 6,887,845, the entirety of which is incorporated herein by reference. As illustrated therein and as would be understood by those skilled in the art made aware of this invention, the present N-substituted glycine residues and resulting peptoid compounds are limited only by synthetic or commercial availability of the corresponding amine reagents.

Printing Microarrays. An 8-mer peptoid library with one constant residue (cysteine on the C-terminal) was synthesized using the conventional split-and-pool method on 500 µm polystyrene macrobeads. Seven different amines were used using the conventional split-and-pool method and a microwave-assisted protocol. The beads were then placed in a 96-well plate with one bead in each well. The peptoids were then cleaved from the beads using a cleavage cocktail of 95% TFA, 2.5% water and 2.5% triisopropylsilane. The liquid contents of four 96-well plates were then transferred to a 384-well Plate using a Tecan Genesis Workstation. When the liquid had evaporated from the Master plates, DMSO (Dimethylsulfoxide) is added to each well using the Tecan Genisis Workstation. The plates are stored in a 4 degree refrigerator and used for printing microarrays as needed. Contents of the 384-well plates are then printed onto maleimide coated glass slides using a NanoPrint LM 360. Complex arrays were printed with a full head of 48 pins and using a spot spacing of 410 µm in a 10 by 10 grid. After printing, the slides were allowed to set for 12 hours before being scanned using a GenePix Autoloader 4200AL Scanner. Slides were scanned with a PMT of 500 to verify spot placement and morphology.

Hybridization Protocol. Microarray slides were covered with hybridization chamber and equilibrated with 1×TBST (50 mM Tris, pH 8.0, 150 mM NaCl, 0.1% Tween20) for 15 minutes. The slides were then blocked with 1 ml of blocking buffer for 1 hour at 4° C. The blocking buffer was removed and the slides were incubated with 1 ml of serum for 16 hours at 4° C. with gentle shaking. Microarrays were then washed three times with 1×TBST and hybridized with Alexa-647 labeled Goat anti-mouse antibody for 2 hours on orbital shaker at 4° C. The chamber cassettes were removed from microarray slides and washed with 1×TBST. The slides were then dried on centrifuge and scanned on microarray scanner by using 635-nm laser at 100% power and 600 photomultiplier tube gain. All the scanned images were analyzed by the Gene Pix Pro 6.0 software and Genespring software.

Designing Peptoid Variants. A sarcosine scan has the effect of replacing each of the side chains of a peptoid in turn with a methyl group rather than a hydrogen, preserving the tertiary amide bond, but removing the bulk of the side chain. Peptoids of interest can be varied at one or more positions within a peptoid to determine which of the side chains positions that influence peptoid binding. Each peptoid can be made by solid phase "sub-monomer" chemistry (See above) where methylamine was employed to displace the bromide at the position where substitution is desired. To test these peptoid variants binding characteristics of each variant peptoid with the appropriate controls can be printed onto a microarray or some other screening platform. Samples containing peptoid targets are hybridized to these arrays. After washing, secondary antibody or other detection method is applied to the array and the intensity of fluorescence at each position determined. When significant diminution in fluorescence was observed at a given spot relative to the parent compound (indicating a lesser binding affinity), is interpreted as indicating that the side chain present at this position in the parent compound influenced binding.

Variant peptoids incorporating one or more amines or R groups as described herein are then incorporated and variants identified using similar synthesis and screening procedures.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
De Jager et al., *Semin. Nucl. Med.*, 23(2):165-179, 1993.
Doolittle and Ben-Zeev, *Methods Mol Biol*, 109:215-237, 1999.
Gulbis and Galand, *Hum. Pathol.*, 24(12):1271-1285, 1993.
Nakamura et al., *In: Handbook of Experimental Immunology* (4th Ed.), Weir et al. (Eds), 1:27, Blackwell Scientific Publ., Oxford, 1987.

What is claimed is:

1. A method of detecting antibodies in an antibody-containing sample from a patient suspected of or having a neurodegenerative disease comprising:
   (a) contacting an antibody-containing sample with a support having affixed thereto a peptoid having a formula selected from:
   (i) the formula (1A):

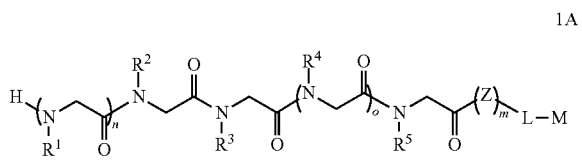

wherein,
$R^1$ is independently selected from $C_{1-6}$alkyl or $C_{2-6}$alkenyl or $C_{1-6}$alkyl substituted with —OH or $NH_2$ or —COOH; or piperonyl or $C_{1-3}$alkylphenyl;
$R^2$ is $C_{1-3}$alkylphenyl;
$R^3$ is $C_{1-3}$alkylphenyl;
$R^4$ is independently selected from $C_{1-6}$alkyl or $C_{2-6}$alkenyl or $C_{1-6}$alkyl substituted with —OH or $NH_2$ or —COOH; or piperonyl or $C_{1-3}$alkylphenyl;
$R^5$ is $C_{1-4}$alkyl substituted with —OH or $NH_2$; or
(ii) formula (1B):

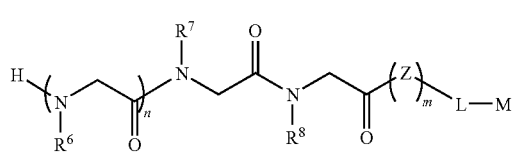

wherein
$R^6$ is independently selected from $C_{2-6}$alkenyl, $C_{1-6}$alkyl independently and optionally substituted with —OH, $NH_2$ or —COOH; piperonyl or $C_{1-6}$alkylphenyl;
$R^7$ is independently selected from $C_{2-6}$alkenyl, $C_{1-6}$alkyl independently and optionally substituted with —OH, $NH_2$ or —COOH; piperonyl;
$R^8$ is independently selected from $C_{2-6}$alkenyl, $C_{1-6}$alkyl independently and optionally substituted with —OH, $NH_2$ or —COOH; piperonyl; or
(iii) formula (1C):

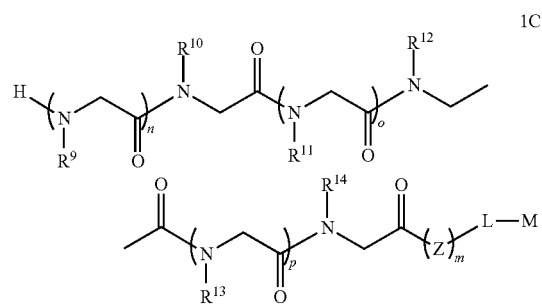

wherein
$R^9$, $R^{11}$ and $R^{13}$ are independently selected from $C_{2-6}$alkenyl, $C_{1-6}$alkyl independently and optionally substituted with —OH, $NH_2$ or —COOH; piperonyl or $C_{1-6}$alkylphenyl;
$R^{10}$ is piperonyl;
$R^{12}$ is $C_{1-6}$alkyl substituted with —OH, $NH_2$ or —COOH;
$R^{14}$ is $C_{1-6}$alkyl substituted with —OH, $NH_2$ or —COOH; or
(iv) formula (1D):

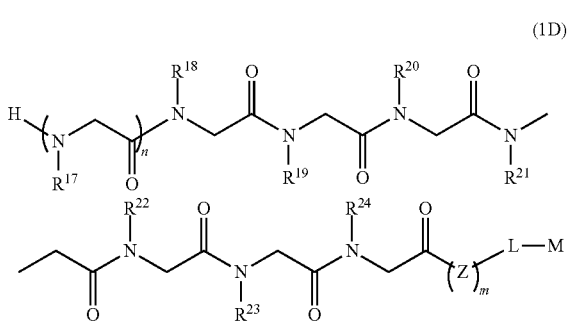

wherein,
$R^{17}$ is independently selected from the group consisting of $C_{1-6}$alkyl optionally substituted with —OH, $NH_2$ or —COOH;
$R^{18}$ is selected from $C_{1-6}$alkyl optionally substituted with —OH, $NH_2$ or —COOH;
$R^{19}$ is selected from $C_{1-6}$alkyl optionally substituted with —OH, $NH_2$ or —COOH;
$R^{20}$ is selected from $C_{1-6}$alkyl optionally substituted with —OH, $NH_2$ or —COOH;
$R^{21}$ is selected from $C_{1-6}$alkylphenyl;
$R^{22}$ is selected from $C_{1-6}$alkylphenyl;
$R^{23}$ is selected from $C_{1-6}$alkyl optionally substituted with —OH, $NH_2$ or —COOH;

$R^{24}$ is selected from $C_{1-6}$alkyl substituted with —OH, $NH_2$ or —COOH;
n is 1; or
for a compound of formula 1D,
$R^{17}$ is $C_{2-6}$alkenyl;
$R^{18}$ is $C_{1-6}$alkyl optionally substituted with —OH, $NH_2$ or —COOH;
$R^{19}$ is piperonyl;
$R^{20}$ is $C_{2-6}$alkenyl;
$R^{21}$ is $C_{2-6}$alkenyl;
$R^{22}$ is $C_{2-6}$alkenyl;
$R^{23}$ is $C_{1-6}$alkyl optionally substituted with —OH, $NH_2$ or —COOH;
$R^{24}$ is $C_{1-6}$alkyl optionally substituted with —OH, $NH_2$ or —COOH;
n is 1; or for a compound of formula 1D,
$R^{17}$ is $C_{1-6}$alkyl optionally substituted with —OH, $NH_2$ or —COOH;
$R^{18}$ is piperonyl;
$R^{19}$ is $C_{1-6}$alkyl optionally substituted with —OH, $NH_2$ or —COOH;
$R^{20}$ is $C_{1-6}$alkyl optionally substituted with —OH, $NH_2$ or —COOH;
$R^{21}$ is $C_{1-6}$alkyl optionally substituted with —OH, $NH_2$ or —COOH;
$R^{22}$ is $C_{1-6}$alkylphenyl;
$R^{23}$ is $C_{1-6}$alkyl optionally substituted with —OH, $NH_2$ or —COOH;
$R^{24}$ is $C_{1-6}$alkyl substituted with —OH, $NH_2$ or —COOH;
n is 1;
wherein L is an optional linker moiety, M is a substrate or support; and m, n, o, and/or p, unless specified, is 0-6, and wherein Z is a functional group capable of coupling to a linker, substrate, or a label; and (b) detecting antibodies bound to said peptoid, wherein antibodies bound to said peptoid are indicative of a neurodegenerative disease in said subject.

2. The method of claim 1, further comprising obtaining said sample from a subject suspected of having Parkinson's disease or Alzheimer's disease and comparing the results of said sample to the results obtained from a control sample from non-diseased patients.

3. The method of claim 2, further comprising making a diagnosis of Alzheimer's Disease for a subject from which said sample was obtained if antibody binding to said peptoid is greater than that observed for said control non-diseased patients.

4. The method of claim 1, wherein said sample is contacted with more than one peptoid of claim 1.

5. The method of claim 4, wherein said sample is contacted with a compound of formula:

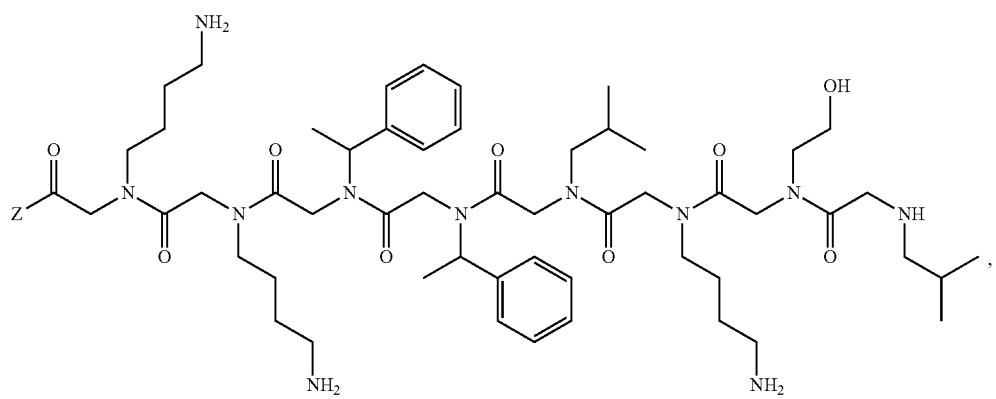

AD1

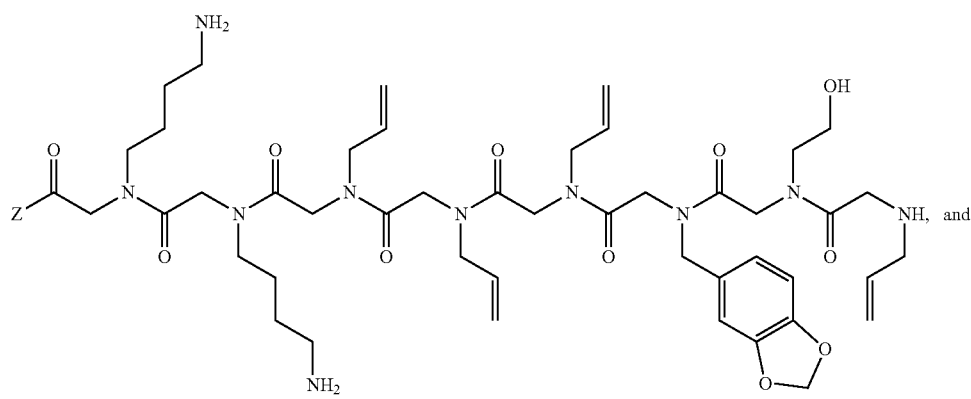

AD2

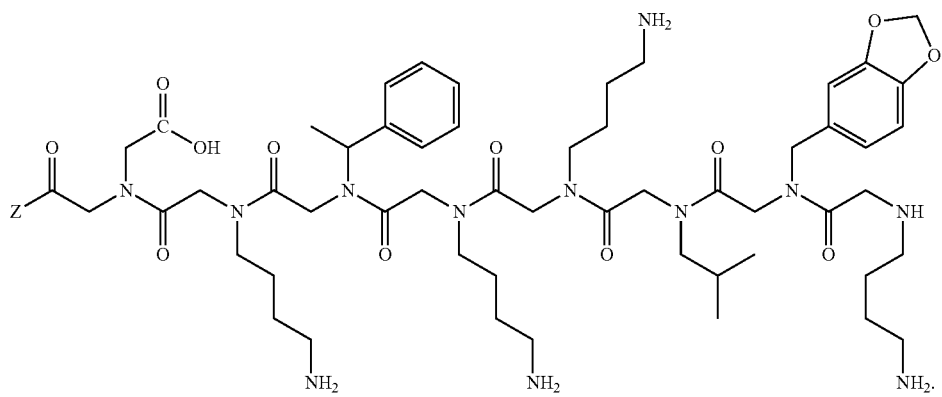

AD3

6. The method of claim 1, wherein said support is a bead, a plate, a dipstick, a filter, a membrane a pin, or a well.

7. The method of claim 1, wherein said sample is blood, serum, saliva or CSF.

8. The method of claim 1, wherein detecting comprises RIA, FIA, ELISA, Western blot, flow cytometry, FRET, or surface plasmon resonance.

9. A method of detecting antibodies in an antibody-containing sample from a patient suspected of or having a neurodegenerative disease comprising:

(a) contacting an antibody-containing sample with a support having affixed thereto a peptoid having a formula selected from, wherein the peptoid has the formula:

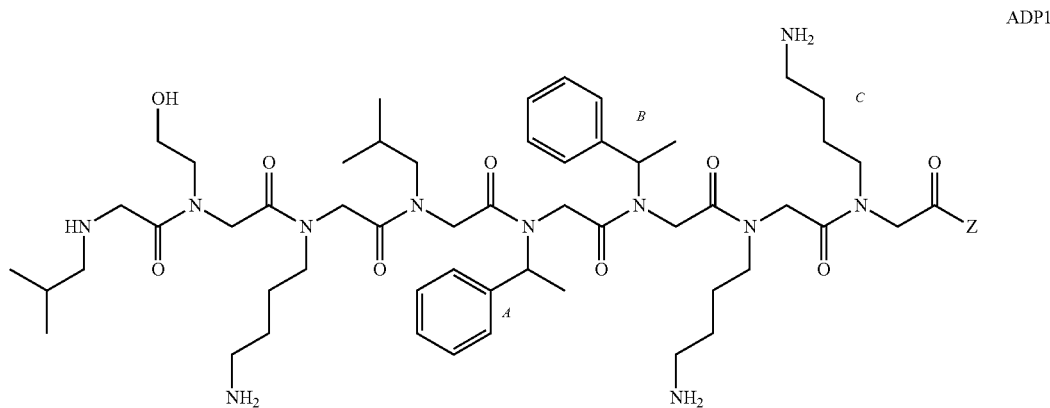

ADP1

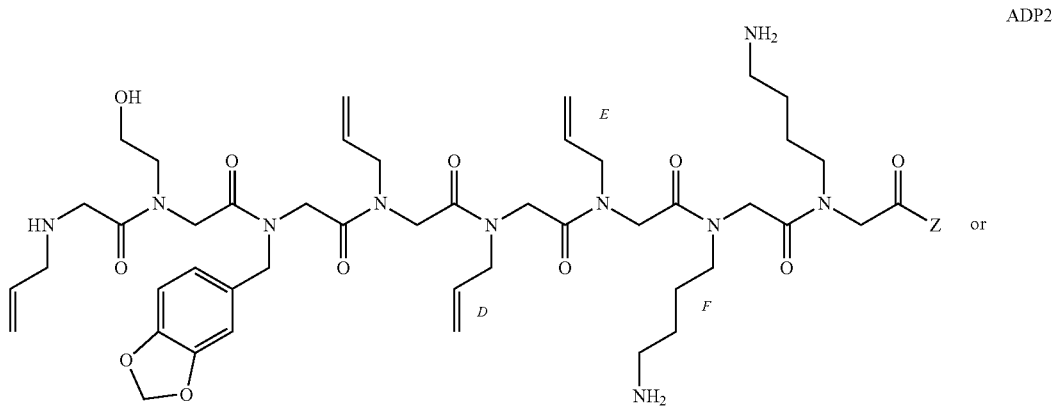

ADP2 or

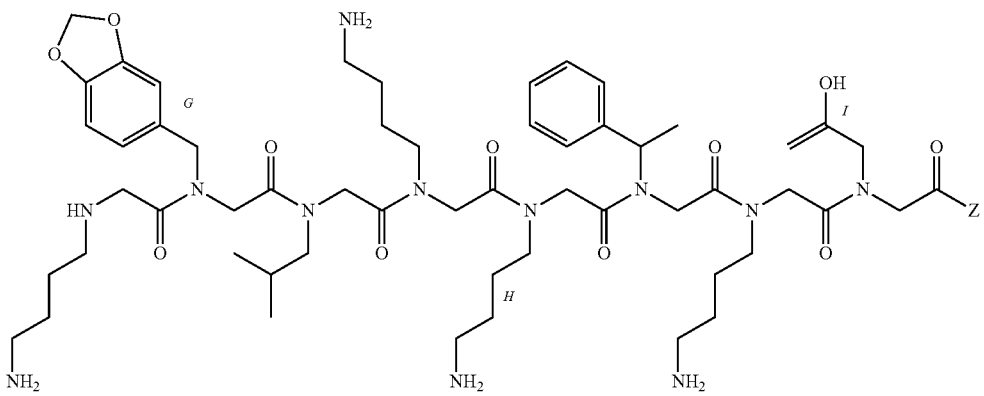

ADP3 wherein A-I indicate the structure is as shown or modified as follows:

| Replacement Amine Position | Amine Side Chain, NH$_2$R (Ref. No.) |
|---|---|
| D, E | n-Bu[1] |
| D, E | s-Bu |
| I | —Cy |
| A, B, G | —CH$_2$CH$_2$—CH(Ph)$_2$ |
| A, B, G | —CH$_2$Ph |
| C, F, H | —CH$_2$CH$_2$OH |
| C, F, H | —OH |
| A, B, G | 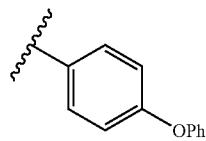 [SMILES: *c1ccc(Oc2ccccc2)cc1] |
| A, B, G | 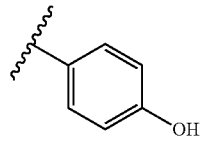 [SMILES: *c1ccc(O)cc1] |
| A, B, G | 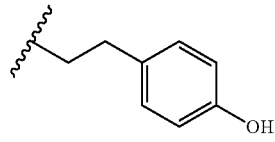 [SMILES: *CCc1ccc(O)cc1] |
| C, F, H | 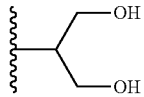 |
| C, F, H | 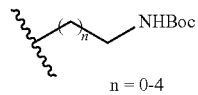 n = 0-4 |
| I | 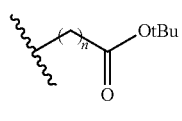 n = 0-4 |

| Replacement Amine Position | Amine Side Chain, NH$_2$R (Ref. No.) |
|---|---|
| H, I | 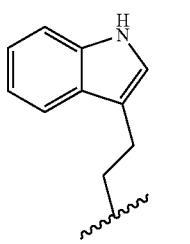 [SMILES: *CCc1c[nH]c2ccccc12] n = 0-4 |
| A, B, G | 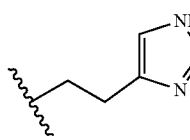 |
| A, B, G | 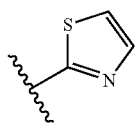 [SMILES: *c1nccs1] |
| A, B, G | 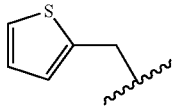 [SMILES: *Cc1cccs1] |
| A, B, G | 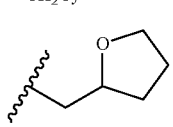 |
| C, F, H | -i-Bu |
| I | —CH$_2$Cy |
| C, F, H |  |
| A, B, G | —CH$_2$OClPh |
| A, B, G | —CH$_2$pOCH$_3$Ph |
| A, B, G | —CHCH$_3$Ph |
| C, F, H | —CH$_2$CH$_2$CH$_2$NHBoc |

-continued
| Replacement Amine Position | Amine Side Chain, NH₂R (Ref. No.) |
|---|---|
| A, B, G | 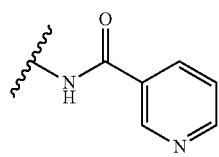 [SMILES: *NC(=O)c1cccnc1] |
| C, F, H | —CH₂CH₂OMe |
| C, F, H | —CH₂CH₂CH₂OH |
| C, F, H | —CH(CH₃)CH₂OH |
| C, F, H | —CH₂CHOHCH₂OH |
| A, B, G | —CH₂CH(OH)Ph |
| A, B, G | 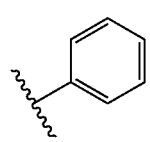 [SMILES: *c1ccccc1] |
| A, B, G | 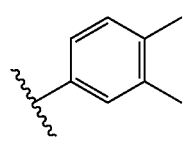 [SMILES: *c1ccc(C)c(C)c1] |
| A, B, G | 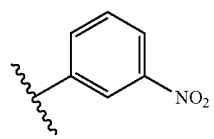 [SMILES: *c1cccc([N+](=O)[O-])c1] |
| A, B, G | 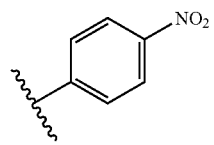 [SMILES: *c1ccc([N+](=O)[O-])cc1] |
| A, B, G | 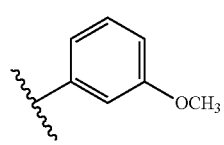 [SMILES: *c1cccc(OC)c1] |
| A, B, G | 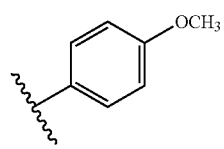 [SMILES: *c1ccc(OC)cc1] |
| A, B, G | 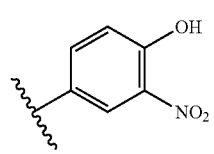 [SMILES: *c1ccc(O)c([N+](=O)[O-])c1] |
| A, B, G | 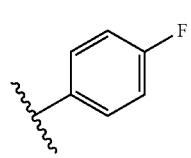 [SMILES: *c1ccc(F)cc1] |
-continued
| Replacement Amine Position | Amine Side Chain, NH₂R (Ref. No.) |
|---|---|
| A, B, G | 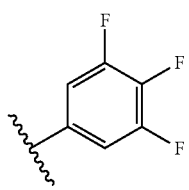 [SMILES: *c1cc(F)c(F)c(F)c1] |
| A, B, G | 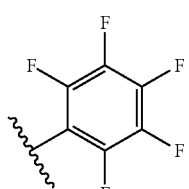 |
| A, B, G | 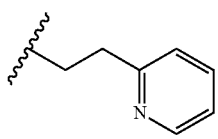 [SMILES: *CCc1ccccn1] |
| A, B, G, C, F, G | 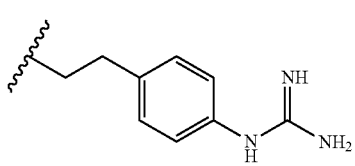 [SMILES: *CCc1ccc(NC(=N)N)cc1] |
| A, B, G | 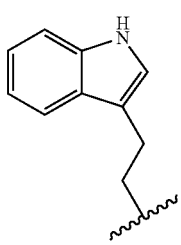 [SMILES: *CCc1c[nH]c2ccccc12] |
| C, F, G | 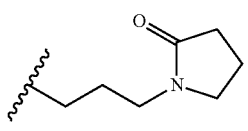 [SMILES: *CCCN1CCCC1=O] |
| A, B, G | 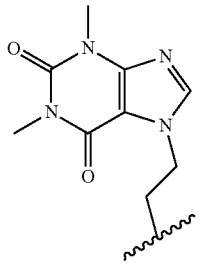 [SMILES: *CCn1cnc2c1c(=O)n(C)c(=O)n2C] |
| C, F, H | 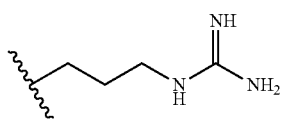 [SMILES: *CCCNC(=N)N] |

| Replacement Amine Position | Amine Side Chain, NH$_2$R (Ref. No.) |
|---|---|
| A, B, D, E, G | 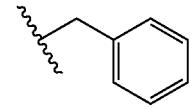 |
| A, B, G, C, F, H | 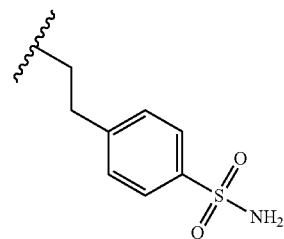 [SMILES: *CCc1ccc(S(N)(=O)=O)cc1] |
| C, F, H | -nPr |
| C, F, H | 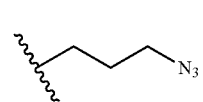 [SMILES: *CCCN=[N+]=[N-]] |
| A, B, G | 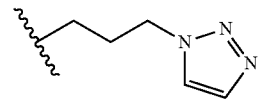 [SMILES: *CCCn1ccnn1] |
| C, F, H | —CH$_2$CH$_2$CH$_2$OMe |
| A, B, C, D, E, F, G, H | 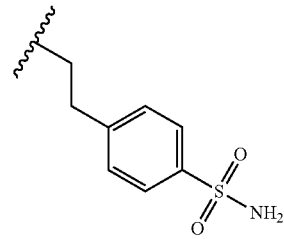 [SMILES: *CCc1ccc(S(N)(=O)=O)cc1] |
| C, F, H | 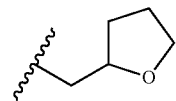 [SMILES: *CC1CCCO1] |
| A, B, G | 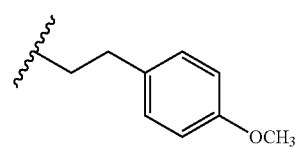 [SMILES: *CCc1ccc(OC)cc1] |
| A, B, G | 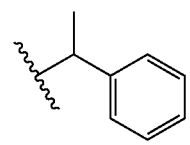 [SMILES: *C(C)c1ccccc1] |
| A, B, G | 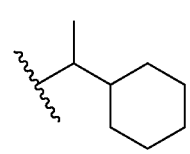 [SMILES: *C(C)C1CCCCC1] |
| Replacement Amine Position | Amine Side Chain, NH$_2$R (Ref. No.) |
|---|---|
| A, B, G | 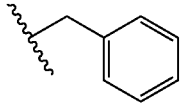 [SMILES: *Cc1ccccc1] |
| A, B, G | 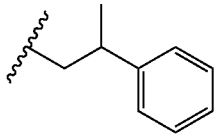 [SMILES: *CC(C)c1ccccc1] |
| A, B, G | 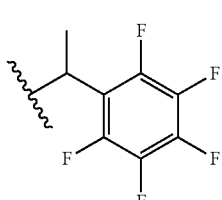 |
| A, B, G | 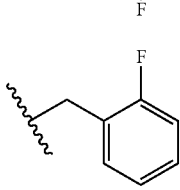 |
| A, B, G | 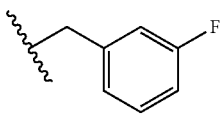 [SMILES: *Cc1cccc(F)c1] |
| A, B, G | 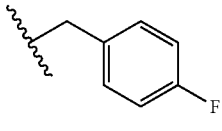 [SMILES: *Cc1ccc(F)cc1] |
| A, B, G | 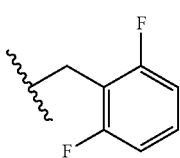 [SMILES: *Cc1c(F)cccc1F] |
| A, B, G | 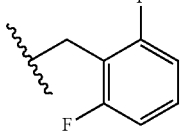 |
| A, B, G | 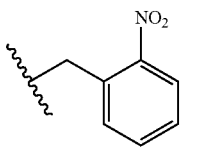 [SMILES: *Cc1ccccc1[N+](=O)[O-]] |
| A, B, G | 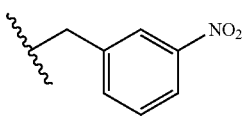 [SMILES: *Cc1cccc([N+](=O)[O-])c1] |

-continued
| Replacement Amine Position | Amine Side Chain, NH₂R (Ref. No.) |
|---|---|
| A, B, G | 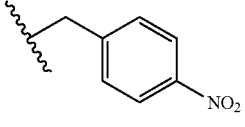 |
| A, B, G | 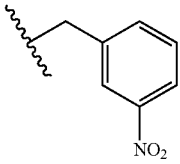 |
| A, B, G | 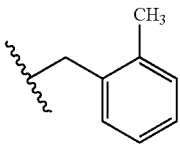 [SMILES: *Cc1ccccc1C] |
| A, B, G | 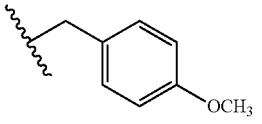 [SMILES: *Cc1ccc(OC)cc1] |
| A, B, G | 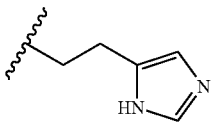 [SMILES: *CCc1cnc[nH]1] |
| A, B, G | 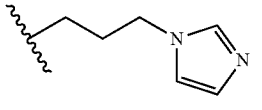 [SMILES: *CCCn1ccnc1] |
| A, B, G | 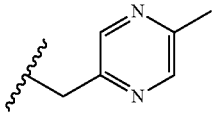 [SMILES: *Cc1cnc(C)cn1] |
| A, B, G | 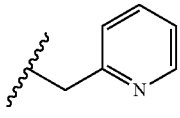 [SMILES: *Cc1ccccn1] |
| A, B, G | 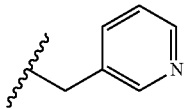 |
| A, B, G | 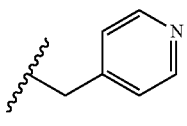 [SMILES: *Cc1ccncc1] |
| A, B, G | 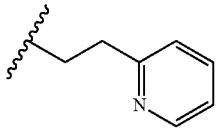 [SMILES: *CCc1ccccn1] |
-continued
| Replacement Amine Position | Amine Side Chain, NH₂R (Ref. No.) |
|---|---|
| A, B, G | 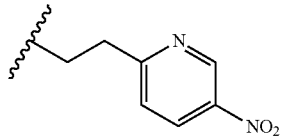 |
| A, B, G | 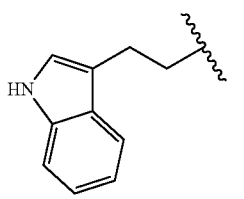 [SMILES: *CCc1c[nH]c2ccccc12] |
| A, B, C, F, G, H | 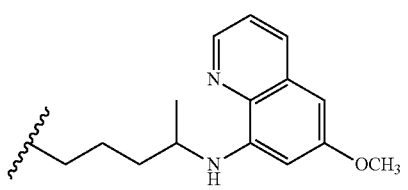 [SMILES: *CCCC(C)Nc1cc(OC)cc2cccnc12] |
| A, B, G | 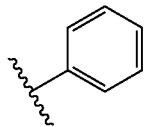 [SMILES: *c1ccccc1] |
| C, F, G | 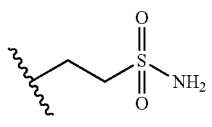 |
| C, F, H, I | 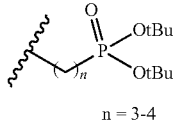 n = 3-4 |
| C, F, H | 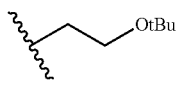 [SMILES: *CCOC(C)(C)C] |
| A, B, G | 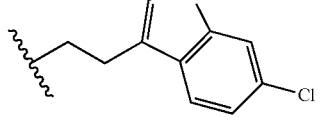 |
| G, A, B | 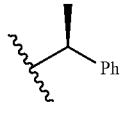 [SMILES: *[C@@H](C)c1ccccc1] |
| A, B, G | 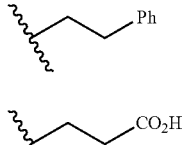 |
| C, F, H, I |  |

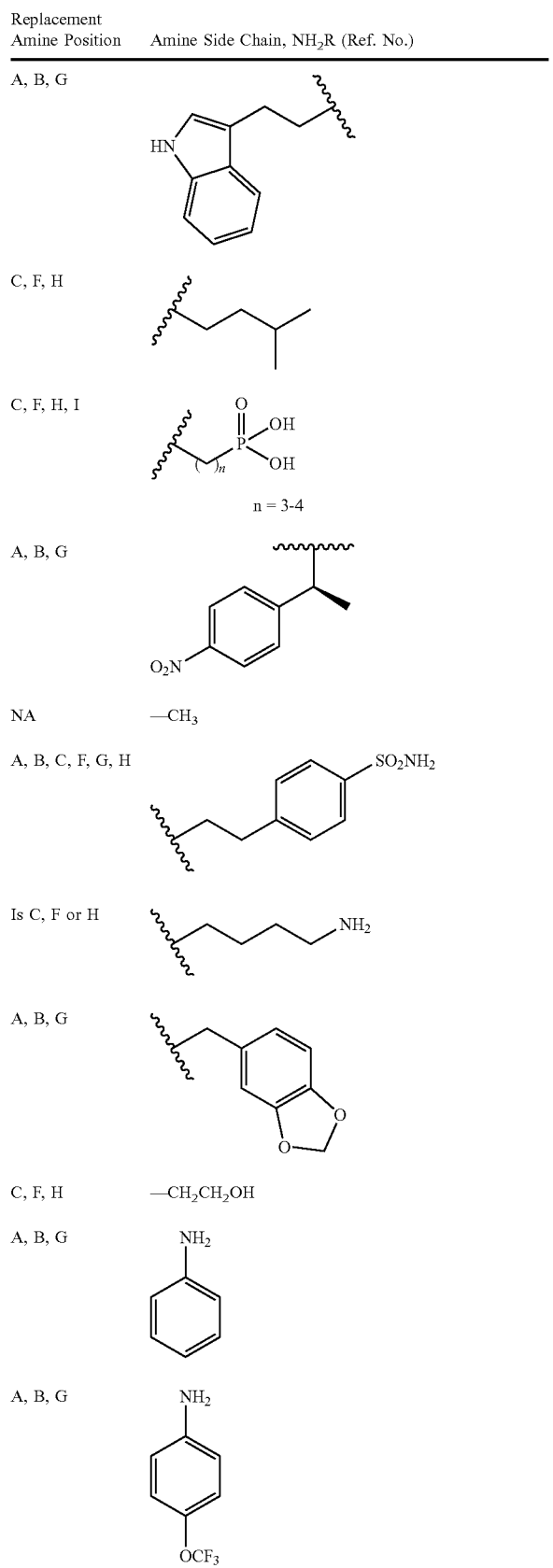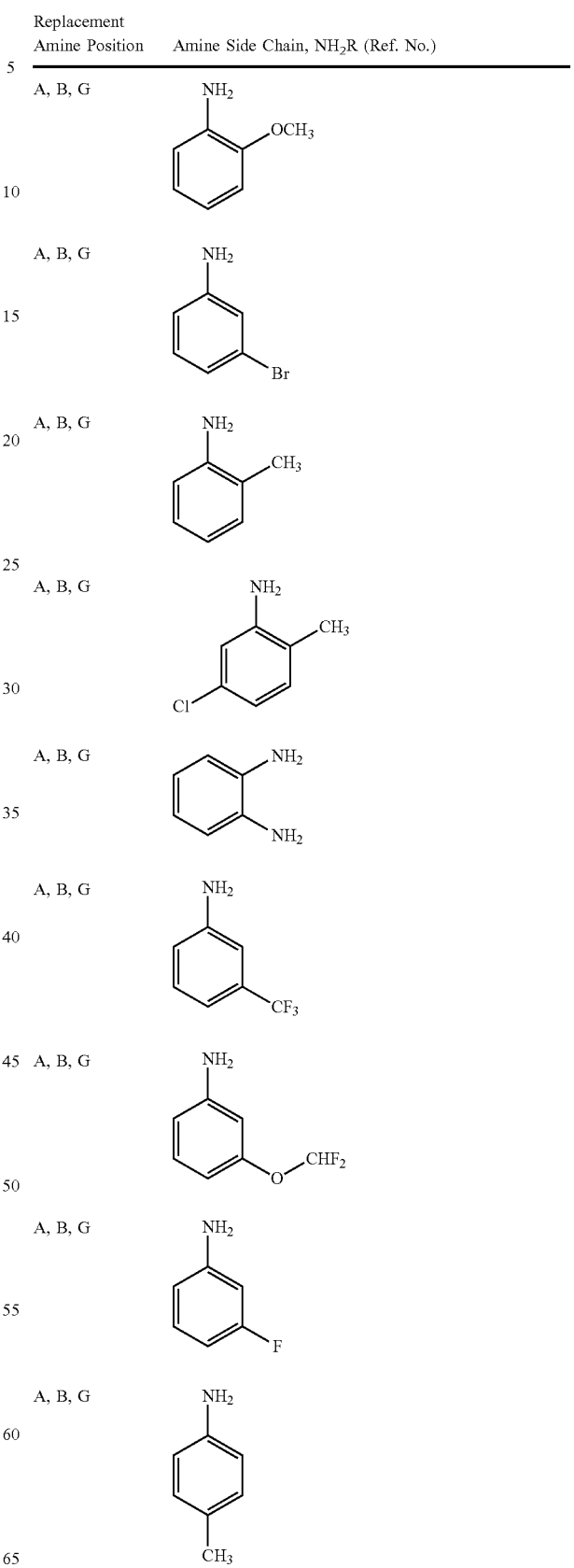

| Replacement Amine Position | Amine Side Chain, NH₂R (Ref. No.) |
|---|---|
| A, B, G | 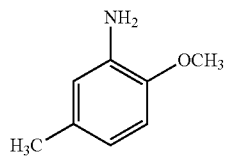 |
| A, B, G | 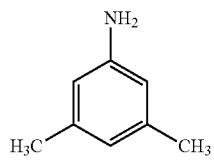 |
| A, B, G | 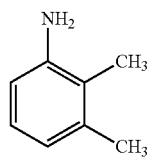 |
| A, B, G | 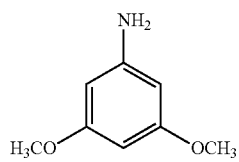 |
| A, B, G | 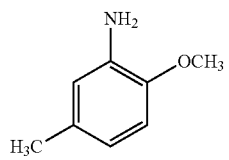 |
| A, B, G | 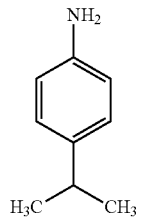 |
| A, B, G | 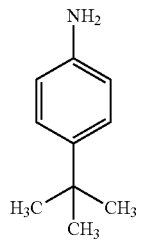 |
| A, B, G | 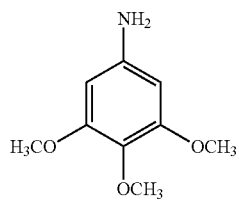 [SMILES: COc1cc(N)cc(OC)c1OC] |
| Replacement Amine Position | Amine Side Chain, NH₂R (Ref. No.) |
|---|---|
| A, B, G, C, F, H | 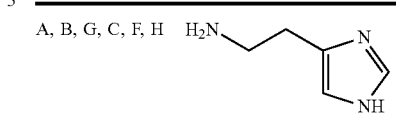 |
| A, B, G | 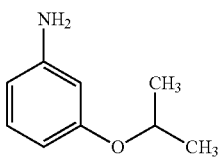 |
| A, B, G | 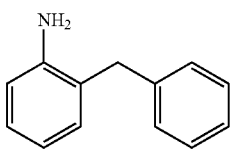 [SMILES: Nc1ccccc1Cc1ccccc1] |
| A, B, G | 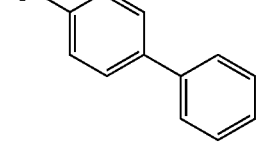 |
| A, B, G | 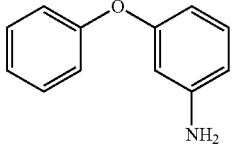 [SMILES: Nc1cccc(Oc2ccccc2)c1] |
| A, B, G | 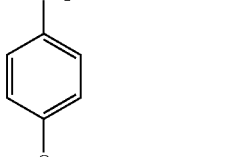 |
| A, B, G | 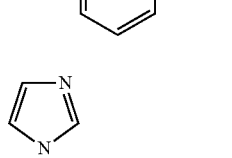 |
| A, B, G | 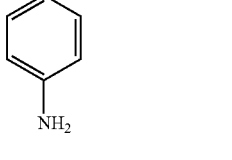 |
| A, B, G | 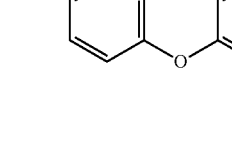 |

| Replacement Amine Position | Amine Side Chain, NH₂R (Ref. No.) |
|---|---|
| A, B, G | 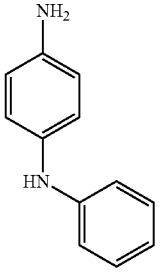 [SMILES: Nc1ccc(Nc2ccccc2)cc1] |
| A, B, G | 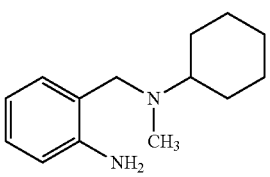 [SMILES: CN(Cc1ccccc1N)C1CCCCC1] |
| A, B, G | 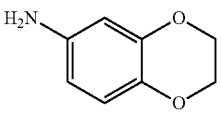 |
| A, B, G | 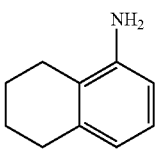 [SMILES: Nc1cccc2c1CCCC2] |
| A, B, G | 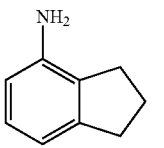 |
| A, B, G | 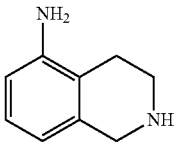 [SMILES: Nc1cccc2c1CCNC2] |
| A, B, G | 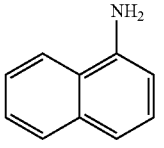 [SMILES: Nc1cccc2ccccc12] |
| A, B, G | 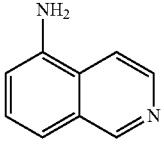 |
| A, B, G | 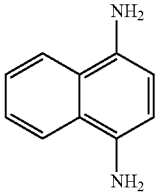 |
| Replacement Amine Position | Amine Side Chain, NH₂R (Ref. No.) |
|---|---|
| A, B, G | 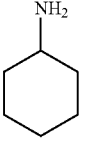 |
| A, B, D, E, G | 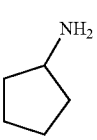 |
| A, B, D, E, G | 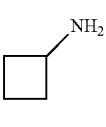 |
| D, E |  |
| A, B, G | 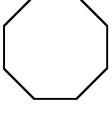 |
| A, B, G | 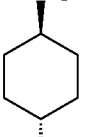 |
| A, B, G | 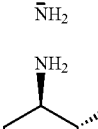 |
| A, B, G | 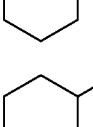 |
| A, B, G | 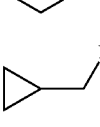 |
| C, F, H | 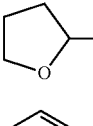 |
| A, B, G | 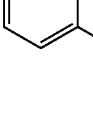 |

-continued

| Replacement Amine Position | Amine Side Chain, NH₂R (Ref. No.) |
|---|---|
| A, B, G | 4-chlorophenethylamine |
| A, B, G | 4-chloro-3-(trifluoromethyl)benzylamine |
| A, B, G | 1,2,3,4-tetrahydroisoquinoline (2,3-dihydro-1H-isoindole-like diamine) |
| A, B, G | 2-phenoxyethylamine |
| A, B, G | 4-(trifluoromethoxy)benzylamine |
| A, B, G | 4-methylbenzylamine |
| A, B, G | 4-methoxybenzylamine |
| A, B, G | 2,4-dichlorophenethylamine |
| A, B, G | 4-(trifluoromethyl)benzylamine |
| A, B, G | 4-aminobenzylamine |
| A, B, G | N-benzylethylenediamine |

-continued

| Replacement Amine Position | Amine Side Chain, NH₂R (Ref. No.) |
|---|---|
| A, B, G | 3,4-dichlorophenethylamine |
| A, B, G | 3-(trifluoromethyl)benzylamine |
| A, B, G | 2,6-dichlorophenethylamine |
| A, B, G | 1-(4-chlorophenyl)ethylamine |
| A, B, D, E, G | benzylamine |
| A, B, G | phenethylamine |
| A, B, G | 2-methoxybenzylamine |
| A, B, G | 2-(trifluoromethyl)benzylamine |

-continued
| Replacement Amine Position | Amine Side Chain, NH₂R (Ref. No.) |
|---|---|
| A, B, G, C, F, G | 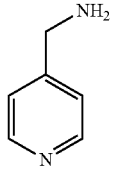 |
| A, B, G | 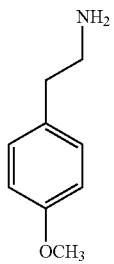 |
| A, B, G | 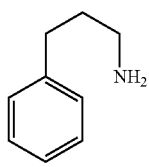 |
| A, B, G | 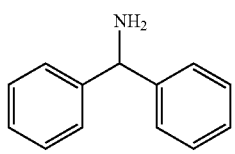 [SMILES: NC(c1ccccc1)c1ccccc1] |
| A, B, G | 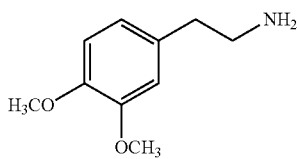 [SMILES: COc1ccc(CCN)cc1OC] |
| A, B, G | 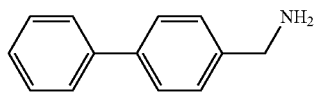 |
| A, B, G | 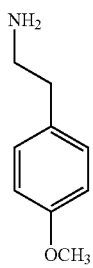 |
| A, B, G | 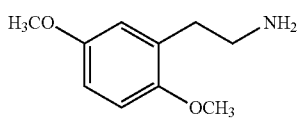 [SMILES: COc1ccc(OC)c(CCN)c1] |
-continued
| Replacement Amine Position | Amine Side Chain, NH₂R (Ref. No.) |
|---|---|
| A, B, G | 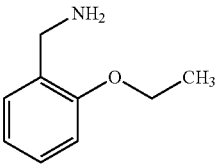 |
| A, B, G | 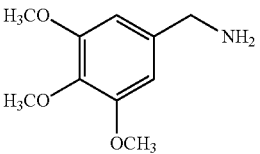 [SMILES: COc1cc(CN)cc(OC)c1OC] |
| A, B, G | 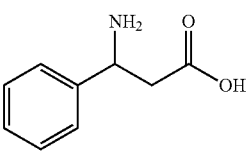 [SMILES: NC(CC(=O)O)c1ccccc1] |
| A, B, G | 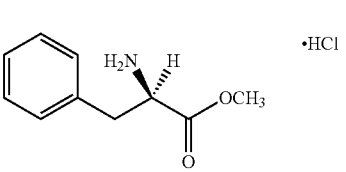 [SMILES: COC(=O)[C@H](N)Cc1ccccc1 ; Cl] |
| A, B, G | 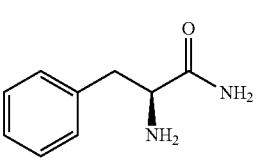 [SMILES: NC(=O)[C@@H](N)Cc1ccccc1] |
| A, B, G | 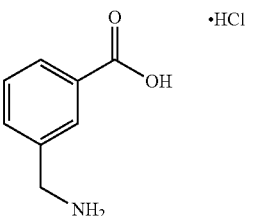 |
| A, B, G | 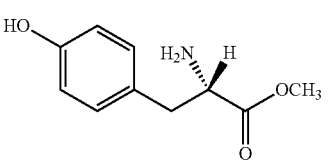 [SMILES: COC(=O)[C@@H](N)Cc1ccc(O)cc1] |
| A, B, G | 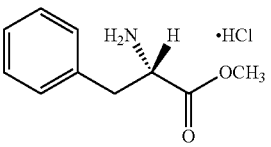 [SMILES: COC(=O)[C@@H](N)Cc1ccccc1 ; Cl] |
| A, B, G | 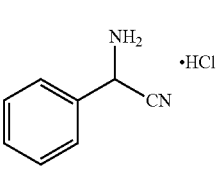 |

-continued
| Replacement Amine Position | Amine Side Chain, NH₂R (Ref. No.) |
|---|---|
| A, B, G | 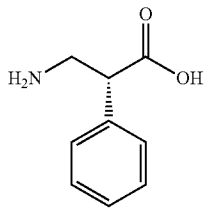 [SMILES: NC[C@H](C(=O)O)c1ccccc1] |
| A, B, G | 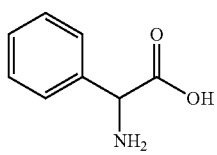 [SMILES: NC(C(=O)O)c1ccccc1] |
| A, B, G | 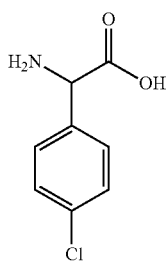 |
| A, B, G | 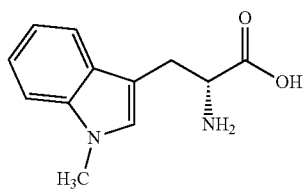 [SMILES: Cn1cc(C[C@@H](N)C(=O)O)c2ccccc21] |
| A, B, G | 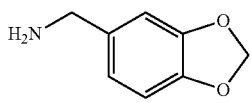 [SMILES: NCc1ccc2c(c1)OCO2] |
| A, B, G | 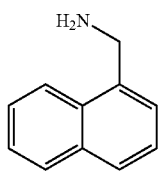 |
| A, B, G | 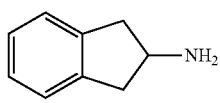 |
| A, B, G | 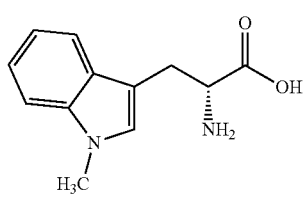 [SMILES: Cn1cc(C[C@@H](N)C(=O)O)c2ccccc21] |
| C, F, H | 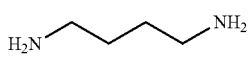 |
| C, F, H | 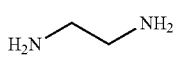 |
-continued
| Replacement Amine Position | Amine Side Chain, NH₂R (Ref. No.) |
|---|---|
| C, F, H | 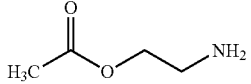 |
| C, F, H | 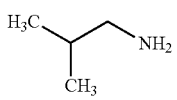 |
| C, F, H |  |
| C, F, H | 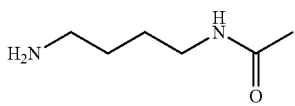 |
| C, F, H | 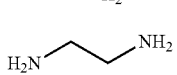 |
| C, F, H | 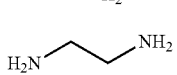 |
| C, F, H |  |
| C, F, H | 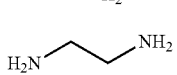 |
| C, F, H | 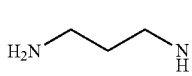 |
| C, F, H | 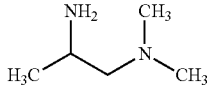 |
| C, F, H | 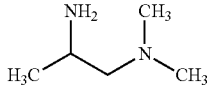 |
| C, F, H | 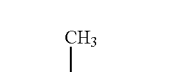 |
| C, F, H | 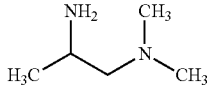 |
| C, F, H | 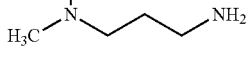 |
| C, F, H |  |
| C, F, H | 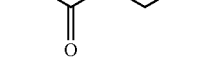 |

-continued
| Replacement Amine Position | Amine Side Chain, NH₂R (Ref. No.) |
|---|---|
| C, F, H | 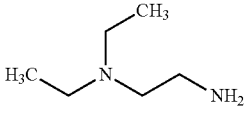 |
| C, F, H | 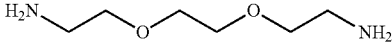 |
| C, F, H | 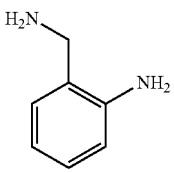 |
| C, F, H | 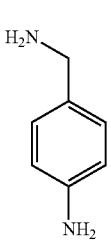 |
| C, F, H | 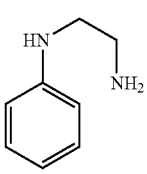 |
| D, E | 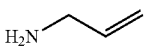 |
| D, E | 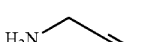 |
| D, E |  |
| D, E | 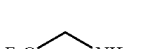 |
| D, E | 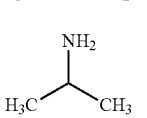 |
| D, E | 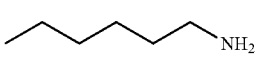 |
| D, E | 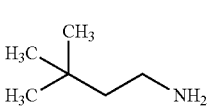 |
| D, E | 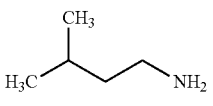 |
| D, E | 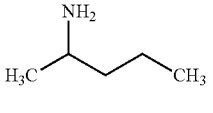 |
-continued
| Replacement Amine Position | Amine Side Chain, NH₂R (Ref. No.) |
|---|---|
| I | 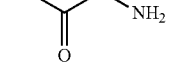 |
| I | 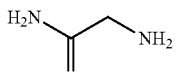 |
| I | 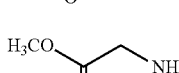 |
| A, B, G | 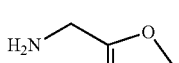 |
| A, B, G |  |
| C, F, H | 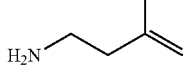 |
| C, F, H | 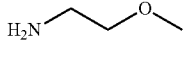 |
| C, F, H | 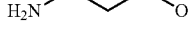 |
| C, F, H | 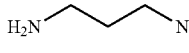 |
| C, F, H |  |
| C, F, H | 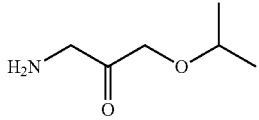 |
| C, F, H | 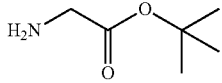 |
| A, B, G | 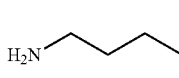 |
| A, B, G | 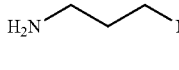 |

-continued

| Replacement Amine Position | Amine Side Chain, NH$_2$R (Ref. No.) |
|---|---|
| A, B, G | 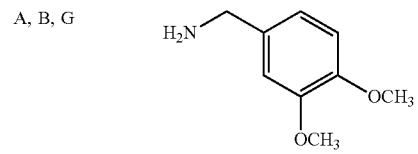 |
| A, B, G | 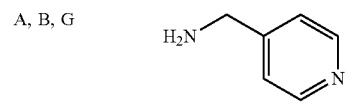 |
| A, B, G | 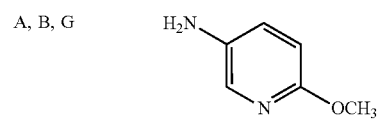 |
| D, E | 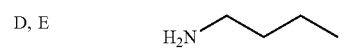 |
| A, B, G, D, E | 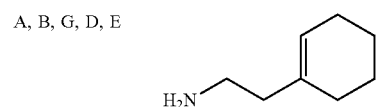 |
| A, B, G | 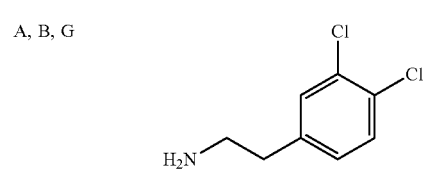 |
| A, B, G | 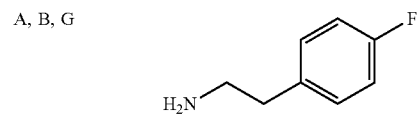 |
| A, B, G | 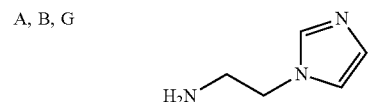 |
| I | 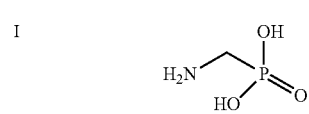 |
| C, F, H |  |
| A, B, G | 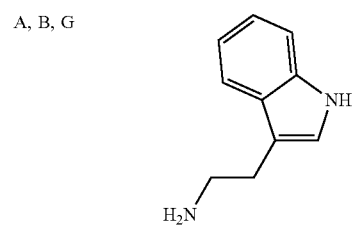 |
| A, B, G | 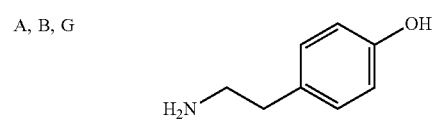 |

-continued

| Replacement Amine Position | Amine Side Chain, NH$_2$R (Ref. No.) |
|---|---|
| A, B, G | 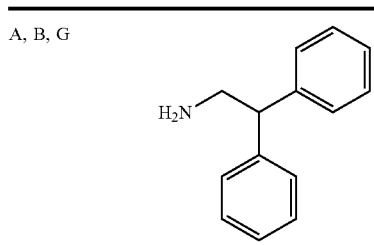 |
| A, B, G | 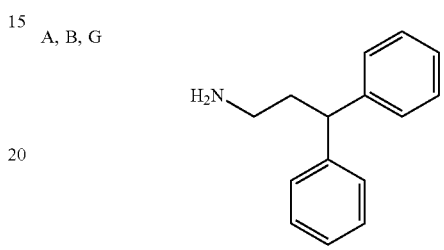 |
| A, B, G | 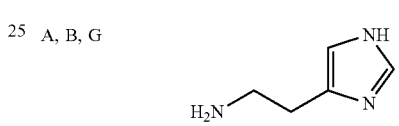 |
| A, B, G | 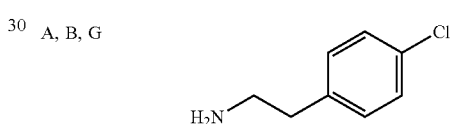 |
| A, B, G | 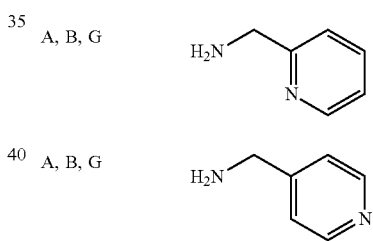 |
| A, B, G | 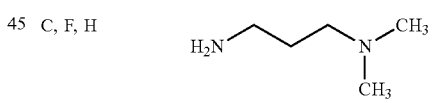 |
| A, B, G |  |
| C, F, H | 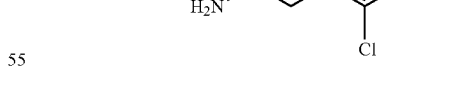 |
| A, B, G |  |
| I |  | and wherein Z is a functional group capable of coupling to a linker, substrate, or a label; and (b) detecting antibodies bound to said peptoid.

10. The method of claim 9, wherein the peptoid has the formula:

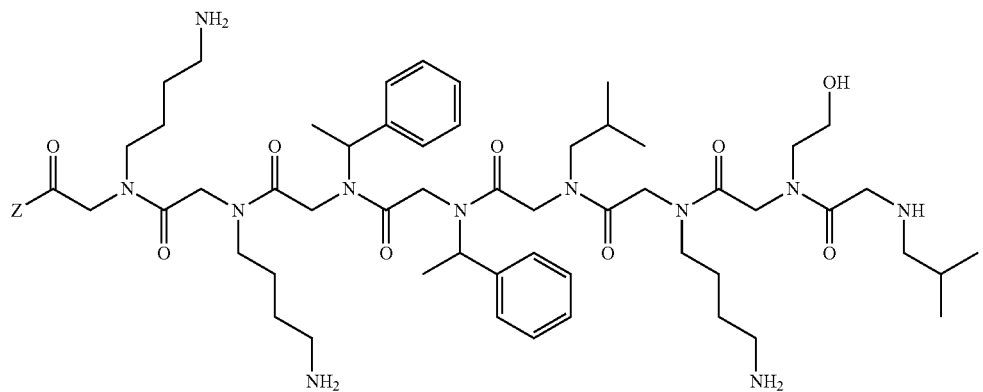
AD1
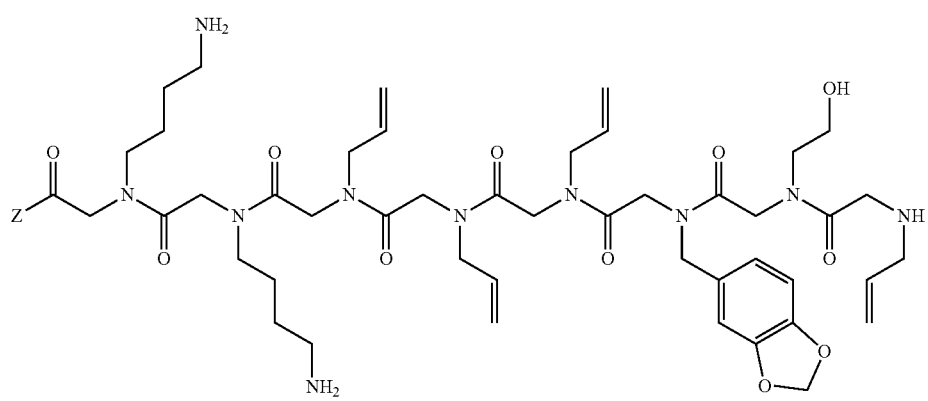
AD2
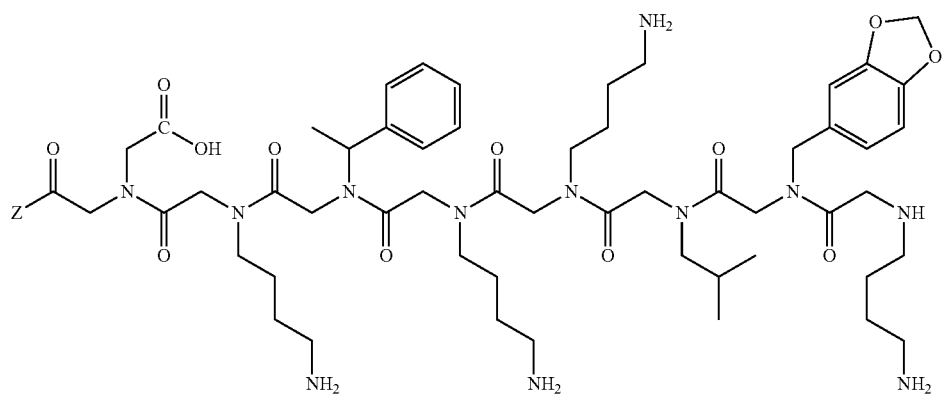
AD3
wherein Z is a functional group capable of coupling to a linker, substrate, or a label.
* * * * *

UNITED STATES PATENT AND TRADEMARK OFFICE
CERTIFICATE OF CORRECTION

PATENT NO. : 9,551,721 B2
APPLICATION NO. : 12/791389
DATED : January 24, 2017
INVENTOR(S) : Muralidhar Reddy Moola et al.

Page 1 of 1

It is certified that error appears in the above-identified patent and that said Letters Patent is hereby corrected as shown below:

In the Claims

In Claim 1, Column 62, Lines 15-26, delete the two chemical drawings and insert

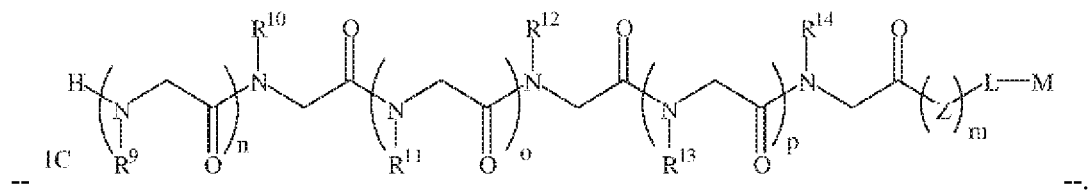

--.

In Claim 1, Column 62, Lines 40-53, delete the two chemical drawings and insert

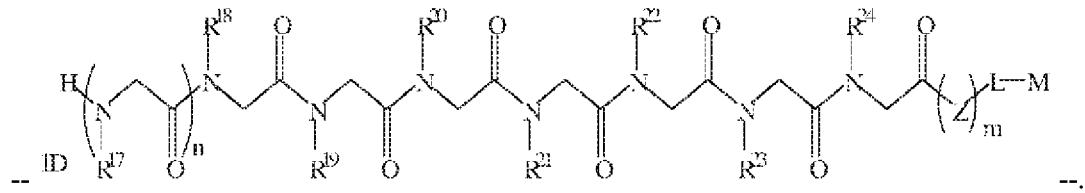

--.

In Claim 9, Column 84, Lines 54-59, delete chemical drawing and insert

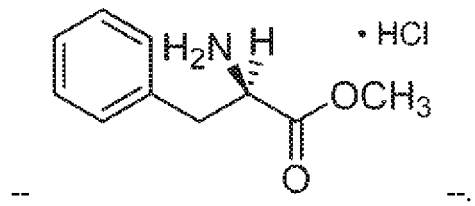

--.

Signed and Sealed this
Second Day of May, 2017

Michelle K. Lee
*Director of the United States Patent and Trademark Office*

UNITED STATES PATENT AND TRADEMARK OFFICE
CERTIFICATE OF CORRECTION

PATENT NO.       : 9,551,721 B2
APPLICATION NO. : 12/791389
DATED            : January 24, 2017
INVENTOR(S)      : Moola et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1001 days.

Signed and Sealed this
Twenty-fifth Day of September, 2018

Andrei Iancu
*Director of the United States Patent and Trademark Office*

UNITED STATES PATENT AND TRADEMARK OFFICE
CERTIFICATE OF CORRECTION

PATENT NO. : 9,551,721 B2
APPLICATION NO. : 12/791389
DATED : January 24, 2017
INVENTOR(S) : Muralidhar Reddy Moola et al.

Page 1 of 1

It is certified that error appears in the above-identified patent and that said Letters Patent is hereby corrected as shown below:

In the Specification

In Column 1, Lines 10-14 delete paragraph and insert:
--This invention was made with government support under grant numbers OD000663 and HV028185 awarded by The National Institutes of Health. The government has certain rights in the invention.--
therefor.

Signed and Sealed this
Seventh Day of July, 2020

Andrei Iancu
*Director of the United States Patent and Trademark Office*